United States Patent
Palani et al.

(10) Patent No.: US 10,793,615 B2
(45) Date of Patent: Oct. 6, 2020

(54) LONG-ACTING CO-AGONISTS OF THE GLUCAGON AND GLP-1 RECEPTORS

(71) Applicants: Merck Sharp & Dohme Corp., Rahway, NJ (US); Anandan Palani, Bridgewater, NJ (US); Ravi Nargund, East Brunswick, NJ (US); Paul E. Carrington, South San Francisco, CA (US); Tomi Sawyer, Southborough, MA (US); Qiaolin Deng, Edison, NJ (US); Antonello Pessi, D'Europa (IT); Elisabetta Bianchi, Pomezia (IT); Federica Orvieto, Pomezia (IT)

(72) Inventors: Anandan Palani, Bridgewater, NJ (US); Ravi Nargund, East Brunswick, NJ (US); Paul E. Carrington, South San Francisco, CA (US); Tomi Sawyer, Southborough, MA (US); Qiaolin Deng, Edison, NJ (US); Antonello Pessi, D'Europa (IT); Elisabetta Bianchi, Pomezia (IT); Federica Orvieto, Pomezia (IT)

(73) Assignee: Merck Sharp & Dohme Corp., Rahway, NJ (US)

( * ) Notice: Subject to any disclaimer, the term of this patent is extended or adjusted under 35 U.S.C. 154(b) by 124 days.

(21) Appl. No.: 15/759,911

(22) PCT Filed: Oct. 21, 2016

(86) PCT No.: PCT/US2016/058008
§ 371 (c)(1),
(2) Date: Mar. 14, 2018

(87) PCT Pub. No.: WO2017/074798
PCT Pub. Date: May 4, 2017

(65) Prior Publication Data
US 2019/0338008 A1 Nov. 7, 2019

Related U.S. Application Data

(60) Provisional application No. 62/246,652, filed on Oct. 27, 2015.

(51) Int. Cl.
| | | |
|---|---|---|
| *A61K 38/00* | (2006.01) | |
| *A61K 38/28* | (2006.01) | |
| *A61P 3/04* | (2006.01) | |
| *A61P 7/12* | (2006.01) | |
| *A61P 3/10* | (2006.01) | |
| *C07K 14/435* | (2006.01) | |
| *C07K 14/605* | (2006.01) | |

(52) U.S. Cl.
CPC .......... *C07K 14/605* (2013.01); *A61K 38/28* (2013.01); *A61P 3/04* (2018.01); *A61K 38/00* (2013.01)

(58) Field of Classification Search
None
See application file for complete search history.

(56) References Cited

U.S. PATENT DOCUMENTS

| | | |
|---|---|---|
| 6,852,690 B1 | 2/2005 | Nauck et al. |
| 2012/0165503 A1 | 6/2012 | Carrington et al. |
| 2013/0090286 A1 | 4/2013 | Bianchi et al. |

FOREIGN PATENT DOCUMENTS

| | | |
|---|---|---|
| AU | 2013200675 | 3/2015 |
| WO | WO2003022304 | 3/2003 |
| WO | WO2004062685 | 7/2004 |
| WO | WO2006134340 | 12/2006 |
| WO | WO2008101017 | 8/2008 |
| WO | WO2009155258 | 12/2009 |
| WO | 2010071807 A1 | 6/2010 |
| WO | WO2010096052 | 8/2010 |
| WO | WO2011075393 | 6/2011 |
| WO | WO2012177443 | 12/2012 |
| WO | WO2012177444 | 12/2012 |
| WO | 2014158900 A1 | 10/2014 |
| WO | 2016065090 A1 | 4/2016 |

OTHER PUBLICATIONS

Lantus prescribing information, accessed Feb. 11, 2020 at URL: accessdata.fda.gov/drugsatfda_docs/label/2009/021081s034lbl.pdf; Jun. 2009, pp. 1-24 (Year: 2009).*
Cornier et al., "The Metabolic Syndrome", Endo. Rev. 29:777-822 (2008) (Year: 2008).*
Metabolic disease, Encyclopedia Britannica, accessed Feb. 12, 2020 at URL: britannica.com/science/metabolic-disease; pp. 1-17 (2019) (Year: 2019).*
Baggio et al., Oxyntomodulin and Glucagon-Like Peptide-1 Differentially, Gastroenterol., 2004, pp. 546-558, 127.
Choudhri et al., Differential hypothalamic neuronal activation following peripheral injection of GLP-1 and oxyntomodulin in mice detected by manganese-enhanced magnetic resonance imaging, Biochem. Biophys. Res. Commun., 2006, pp. 298-306, 350.
Cohen et al., Oxyntomodulin Suppresses Appetite and Reduces Food intake in Humans, J. Clin. Endocrinol. Metab., 2003, pp. 4696-4701, 88.

(Continued)

*Primary Examiner* — Julie Ha
*Assistant Examiner* — Kristina M Hellman
(74) *Attorney, Agent, or Firm* — Baerbel R. Brown; Catherine D. Fitch

(57) ABSTRACT

Long-acting co-agonists of the glucagon and GLP-1 receptors are described.

17 Claims, 6 Drawing Sheets
Specification includes a Sequence Listing.

(56) References Cited

OTHER PUBLICATIONS

Dakin et al., Oxyntomodulin ameliorates glucose intolerance in mice fed a high-fat diet, Am. J. Physiol. Endocrinol. Metab., 2008, pp. E142-E147, 294.

Dakin et al., Oxyntomodulin Inhibits Food Intake in the Rat, Endocrinology, 2001, pp. 4244-4250, 142.

Dakin et al., Peripheral Oxyntomodulin Reduces Food Intake and Body Weight Gain in Rats, Endocrinology, 2004, pp. 2687-2695, 145.

Dakin et al., Repeated ICV administration of oxyntomodulin causes a greater reduction in body weight gain than in pair-fed rats, Am. J. Physiol. Endocrinol. Metab., 2002, pp. E1173-E1177, 283.

Day, Jonathan W., A New Glucagon and GLP 1 co agonist eliminates obesity in rodents, Nature Chemical Biology, 2009, No. 10 pp. 749-757, 5.

Drucker et al., Biologic actions and therapeutic potential of the proglucagon-derived peptides, J. Nat. Clin. Pract. Endocrinol. Metab., 2005, pp. 22-31, 1.

Habegger et al., The metabolic actions of glucagon revisited, Nat. Rev. Endocrinol., 2010, pp. 689-697, 6.

Holst, Gut hormones as pharmaceuticals From enteroglucagon to GLP-1 and GLP-2, Regul. Pept., 2000, pp. 45-51, 93.

Jarrouse et al., A Pure Enteroglucagon, Oxyntomodulin (Glucagon 37), Stimulates Insulin Release in Perfused Rat Pancreas, Endocrinol., 1984, pp. 102-105, 115.

Jiang et al., Glucagon and regulation of glucose metabolism, Am. J. Physiol. Endocrinol. Metab., 2003, pp. E671-E678, 284.

Jorgensen et al., Oxyntomodulin Differentially Affects Glucagon-Like Peptide-1 Receptor Beta-Arrestin Recruitment and Signaling through G alpha s, J. Pharma. Exp. Therapeut., 2007, pp. 148-154, 322.

Lykkegaard et al., Regulatory Role of Glucose and Melanocortin 4 Receptor in AMP-Activated Protein Kinase Activity in the Hypothalamus: Association with Feeding Behavior, ADA Scientific Sessions, Abstract No. 1506 P, 2003, Abstract No. 1506P, Abstract No. 1506P.

Pocai et al., Glucagon-Like Peptide 1/Glucagon Receptor Dual Agonism Reverses Obesity in Mice, Diabetes, 2009, pp. 2258-2266, 58.

Salter, Metabolic Effects of Glucagon in the Wistar Rat, Am. J. Clin. Nutr., 1960, pp. 535-539, 8.

Schjoldager et al., Oxyntomodulin: a potential hormone from the distal gut. Pharmacokinetics and effects on gastric acid and insulin secretion in man, Eur. J. Clin. Invest., 1988, pp. 499-503, 18.

Sowden et al., Oxyntomodulin increases intrinsic heart rate in mice independent of the glucagon-like peptide-1 receptor, Am. J. Physiol. Regul. Integr. Comp. Physiol., 2007, pp. R962-R970, 292.

Wynne et al., Subcutaneous Oxyntomodulin Reduces Body Weight in Overweight and Obese Subjects, Diabetes, 2005, pp. 2390-2395, 54.

Zhu et al., The Role of Dipeptidyl Peptidase IV in the Cleavage of Glucagon Family Peptides, J. Biol. Chem., 2002, pp. 22418-22423, 278.

Lau, Jesper et al., Discovery of the Once-Weekly Glucagon-Like Peptide-1 (GLP-1) Analogue Semaglutide, Journal of Medicinal Chemistry, 2015, 7370-7380, 58(18).

\* cited by examiner

SEQUENCE LISTING

```
<160> NUMBER OF SEQ ID NOS: 80

<210> SEQ ID NO 1
<211> LENGTH: 31
<212> TYPE: PRT
<213> ORGANISM: Artificial Sequence
<220> FEATURE:
<223> OTHER INFORMATION: Peptide TP340
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is  alpha- alpha-aminoisobutyric acid
      (aib)
<220> FEATURE:
<221> NAME/KEY: MISC_FEATURE
<222> LOCATION: (21)..(21)
<223> OTHER INFORMATION: Lys conjugated to PEG2PEG2-gammaGlu-C16-OH
<220> FEATURE:
<221> NAME/KEY: MISC_FEATURE
<222> LOCATION: (31)..(31)
<223> OTHER INFORMATION: Xaa is gammaGlu
<220> FEATURE:
<221> NAME/KEY: MISC_FEATURE
<222> LOCATION: (31)..(31)
<223> OTHER INFORMATION: C-terminal amide

<400> SEQUENCE: 1

His Xaa Gln Gly Thr Phe Thr Ser Asp Tyr Ser Lys Tyr Leu Asp Xaa
1               5                   10                  15

Arg Ala Ala Gln Lys Phe Val Gln Trp Leu Leu Ala Thr Lys Xaa
            20                  25                  30

<210> SEQ ID NO 2
<211> LENGTH: 29
<212> TYPE: PRT
<213> ORGANISM: Artificial sequence
<220> FEATURE:
<223> OTHER INFORMATION: Peptide TP342
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide
```

```
<400> SEQUENCE: 2

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Leu Asp Thr
            20                  25

<210> SEQ ID NO 3
<211> LENGTH: 29
<212> TYPE: PRT
<213> ORGANISM: Artificial sequence
<220> FEATURE:
<223> OTHER INFORMATION: Peptide TP344
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (21)..(21)
<223> OTHER INFORMATION: Lys conjugated to PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 3

His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Leu Asp Thr
            20                  25

<210> SEQ ID NO 4
<211> LENGTH: 29
<212> TYPE: PRT
<213> ORGANISM: Artificial sequence
<220> FEATURE:
<223> OTHER INFORMATION: Peptide TP369
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (10)..(10)
<223> OTHER INFORMATION: Lys conjugated to PEG2PEG2-gammaGlu-C18-OH
<220> FEATURE:
<221> NAME/KEY: MISC_FEATURE
<222> LOCATION: (16)..(16)
<223> OTHER INFORMATION: Xaa is  alpha-alpha-aminoisobutyric acid (aib)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 4

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Xaa Asp Thr
            20                  25

<210> SEQ ID NO 5
<211> LENGTH: 29
<212> TYPE: PRT
<213> ORGANISM: Artificial sequence
<220> FEATURE:
```

```
<223> OTHER INFORMATION: Peptide TP370
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (12)..(12)
<223> OTHER INFORMATION: Lys conjugated to PEG2PEG2-gammaGlu-C18-OH
<220> FEATURE:
<221> NAME/KEY: MISC_FEATURE
<222> LOCATION: (16)..(16)
<223> OTHER INFORMATION: Xaa is  alpha-alpha-aminoisobutyric acid (aib)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 5

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Xaa Asp Thr
            20                  25

<210> SEQ ID NO 6
<211> LENGTH: 29
<212> TYPE: PRT
<213> ORGANISM: Artificial sequence
<220> FEATURE:
<223> OTHER INFORMATION: Peptide TP371
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Lys conjugated to PEG2PEG2-gammaGlu-C18-OH
<220> FEATURE:
<221> NAME/KEY: MISC_FEATURE
<222> LOCATION: (29)..(29)
<223> OTHER INFORMATION: C-terminal amide

<400> SEQUENCE: 6

His Xaa Gln Gly Thr Phe Thr Ser Asp Lys Ser Lys Tyr Leu Asp Ala
1               5                   10                  15

Arg Ala Ala Gln Asp Phe Val Gln Trp Leu Leu Asp Thr
            20                  25

<210> SEQ ID NO 7
<211> LENGTH: 29
<212> TYPE: PRT
<213> ORGANISM: Artificial sequence
<220> FEATURE:
<223> OTHER INFORMATION: Peptide TP372
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (12)..(12)
<223> OTHER INFORMATION: Lys conjugated to PEG2PEG2
      PEG2PEG2-gammaGlu-C18-OH
<220> FEATURE:
<221> NAME/KEY: MISC_FEATURE
<222> LOCATION: (29)..(29)
<223> OTHER INFORMATION: C-terminal amide
```

-continued

<400> SEQUENCE: 7

His Xaa Gln Gly Thr Phe Thr Ser Asp Tyr Ser Lys Tyr Leu Asp Ala
1               5                   10                  15

Arg Ala Ala Gln Asp Phe Val Gln Trp Leu Leu Asp Thr
            20                  25

<210> SEQ ID NO 8
<211> LENGTH: 29
<212> TYPE: PRT
<213> ORGANISM: Artificial sequence
<220> FEATURE:
<223> OTHER INFORMATION: Peptide TP378
<220> FEATURE:
<221> NAME/KEY: MISC_FEATURE
<222> LOCATION: (2)..(2)
<223> OTHER INFORMATION: Peptide TP378
<220> FEATURE:
<221> NAME/KEY: MISC_FEATURE
<222> LOCATION: (2)..(2)
<223> OTHER INFORMATION: Peptide TP378
<220> FEATURE:
<221> NAME/KEY: MISC_FEATURE
<222> LOCATION: (10)..(10)
<223> OTHER INFORMATION: Xaa is p-aminomethyl-L-phenylalanine (pAF)
<220> FEATURE:
<221> NAME/KEY: MISC_FEATURE
<222> LOCATION: (10)..(10)
<223> OTHER INFORMATION: pAF conjugated to  PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 8

His Xaa Gln Gly Thr Phe Thr Ser Asp Xaa Ser Lys Tyr Leu Asp Glu
1               5                   10                  15

Arg Ala Ala Gln Asp Phe Val Gln Trp Leu Leu Lys Thr
            20                  25

<210> SEQ ID NO 9
<211> LENGTH: 29
<212> TYPE: PRT
<213> ORGANISM: Artificial sequence
<220> FEATURE:
<223> OTHER INFORMATION: Peptide TP379
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Lys conjugated to  gammaGlu-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 9

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Lys Thr
            20                  25

<210> SEQ ID NO 10
<211> LENGTH: 29
<212> TYPE: PRT
<213> ORGANISM: Artificial sequence
<220> FEATURE:
<223> OTHER INFORMATION: Peptide TP380

```
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (10)..(10)
<223> OTHER INFORMATION: Xaa is p-aminomethyl-L-phenylalanine (pAF)
<220> FEATURE:
<221> NAME/KEY: MISC_FEATURE
<222> LOCATION: (10)..(10)
<223> OTHER INFORMATION: pAF conjugated to  PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 10

His Xaa Gln Gly Thr Phe Thr Ser Asp Xaa Ser Lys Tyr Leu Asp Glu
1               5                   10                  15

Arg Ala Ala Gln Asp Phe Val Gln Trp Leu Leu Lys Thr
            20                  25

<210> SEQ ID NO 11
<211> LENGTH: 31
<212> TYPE: PRT
<213> ORGANISM: Artificial sequence
<220> FEATURE:
<223> OTHER INFORMATION: Peptide TP382
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (10)..(10)
<223> OTHER INFORMATION: Xaa is p-aminomethyl-L-phenylalanine (pAF)
<220> FEATURE:
<221> NAME/KEY: MISC_FEATURE
<222> LOCATION: (10)..(10)
<223> OTHER INFORMATION: pAF conjugated to
      PEG2PEG2 PEG2PEG2-gammaGlu-C16-OH
<220> FEATURE:
<221> NAME/KEY: MISC_FEATURE
<222> LOCATION: (16)..(16)
<223> OTHER INFORMATION: Xaa is  alpha-alpha-aminoisobutyric acid (aib)
<220> FEATURE:
<221> NAME/KEY: MISC_FEATURE
<222> LOCATION: (31)..(31)
<223> OTHER INFORMATION: Xaa is gammaGlu
<220> FEATURE:
<221> NAME/KEY: MISC_FEATURE
<222> LOCATION: (31)..(31)
<223> OTHER INFORMATION: C-terminal amide

<400> SEQUENCE: 11

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Leu Ala Thr Lys Xaa
            20                  25                  30

<210> SEQ ID NO 12
<211> LENGTH: 29
<212> TYPE: PRT
<213> ORGANISM: Artificial sequence
<220> FEATURE:
<223> OTHER INFORMATION: Peptide TP383
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
```

```
<222> LOCATION: (10)..(10)
<223> OTHER INFORMATION: Xaa is p-aminomethyl-L-phenylalanine (pAF)
<220> FEATURE:
<221> NAME/KEY: MISC_FEATURE
<222> LOCATION: (10)..(10)
<223> OTHER INFORMATION: pAF conjugated to  PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 12

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Xaa Asp Thr
            20                  25

<210> SEQ ID NO 13
<211> LENGTH: 29
<212> TYPE: PRT
<213> ORGANISM: Artificial sequence
<220> FEATURE:
<223> OTHER INFORMATION: Peptide TP384
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (10)..(10)
<223> OTHER INFORMATION: Xaa is p-aminomethyl-L-phenylalanine (pAF)
<220> FEATURE:
<221> NAME/KEY: MISC_FEATURE
<222> LOCATION: (10)..(10)
<223> OTHER INFORMATION: pAF conjugated to  PEG2PEG2-gammaGlu-C16
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 13

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Xaa Asp Thr
            20                  25

<210> SEQ ID NO 14
<211> LENGTH: 29
<212> TYPE: PRT
<213> ORGANISM: Artificial sequence
<220> FEATURE:
<223> OTHER INFORMATION: Peptide TP403
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
```

```
<221> NAME/KEY: MISC_FEATURE
<222> LOCATION: (29)..(29)
<223> OTHER INFORMATION: C-terminal amide

<400> SEQUENCE: 14

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Asp Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: Peptide TP404
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (21)..(21)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 15

His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Xaa Asp Thr
            20                  25

<210> SEQ ID NO 16
<211> LENGTH: 29
<212> TYPE: PRT
<213> ORGANISM: Artificial sequence
<220> FEATURE:
<223> OTHER INFORMATION: Peptide TP406
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (21)..(21)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 16

His Xaa Gln Gly Thr Phe Thr Ser Asp Tyr Ser Lys Tyr Leu Asp Glu
1               5                   10                  15

Arg Ala Ala Gln Lys Phe Val Gln Trp Leu Xaa Asp Thr
            20                  25

<210> SEQ ID NO 17
<211> LENGTH: 29
```

```
<212> TYPE: PRT
<213> ORGANISM: Artificial sequence
<220> FEATURE:
<223> OTHER INFORMATION: Peptide TP407
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 17

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Leu Asp Thr
            20                  25

<210> SEQ ID NO 18
<211> LENGTH: 29
<212> TYPE: PRT
<213> ORGANISM: Artificial sequence
<220> FEATURE:
<223> OTHER INFORMATION: Peptide TP408
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Lys conjugated to PEG2PEG2-gammaGlu-C16-OH
<220> FEATURE:
<221> NAME/KEY: MISC_FEATURE
<222> LOCATION: (31)..(31)
<223> OTHER INFORMATION: C-terminal amide

<400> SEQUENCE: 18

His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Leu Asp Thr
            20                  25

<210> SEQ ID NO 19
<211> LENGTH: 29
<212> TYPE: PRT
<213> ORGANISM: Artificial sequence
<220> FEATURE:
<223> OTHER INFORMATION: Peptide TP409
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 19
```

```
His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Asp Thr
            20                  25

<210> SEQ ID NO 20
<211> LENGTH: 29
<212> TYPE: PRT
<213> ORGANISM: Artificial sequnece
<220> FEATURE:
<223> OTHER INFORMATION: Peptide TP410
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 20

His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Xaa Asp Thr
            20                  25

<210> SEQ ID NO 21
<211> LENGTH: 29
<212> TYPE: PRT
<213> ORGANISM: Artificial sequence
<220> FEATURE:
<223> OTHER INFORMATION: Peptide TP413
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (21)..(21)
<223> OTHER INFORMATION: Lys conjugated to
      PEG2PEG2 PEG2PEG2-gammaGlu-C18-OH
<220> FEATURE:
<221> NAME/KEY: MISC_FEATURE
<222> LOCATION: (29)..(29)
<223> OTHER INFORMATION: C-terminal amide

<400> SEQUENCE: 21

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Asp Thr
            20                  25

<210> SEQ ID NO 22
<211> LENGTH: 29
<212> TYPE: PRT
<213> ORGANISM: Artificial sequence
<220> FEATURE:
<223> OTHER INFORMATION: Peptide TP416
<220> FEATURE:
<221> NAME/KEY: MISC_FEATURE
<222> LOCATION: (2)..(2)
<223> OTHER INFORMATION: Xaa is D-Serine
<220> FEATURE:
```

```
<221> NAME/KEY: MISC_FEATURE
<222> LOCATION: (20)..(20)
<223> OTHER INFORMATION: Xaa is p-aminomethyl-L-phenylalanine (pAF)
<220> FEATURE:
<221> NAME/KEY: MISC_FEATURE
<222> LOCATION: (20)..(20)
<223> OTHER INFORMATION: pAF conjugated to   PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 22

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Leu Asp Thr
            20                  25

<210> SEQ ID NO 23
<211> LENGTH: 29
<212> TYPE: PRT
<213> ORGANISM: Artificial sequence
<220> FEATURE:
<223> OTHER INFORMATION: Peptide TP417
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (21)..(21)
<223> OTHER INFORMATION: Xaa is p-aminomethyl-L-phenylalanine (pAF)
<220> FEATURE:
<221> NAME/KEY: MISC_FEATURE
<222> LOCATION: (21)..(21)
<223> OTHER INFORMATION: pAF conjugated to   PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 23

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Asp Thr
            20                  25

<210> SEQ ID NO 24
<211> LENGTH: 29
<212> TYPE: PRT
<213> ORGANISM: Artificial sequence
<220> FEATURE:
<223> OTHER INFORMATION: Peptide TP418
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (12)..(12)
<223> OTHER INFORMATION: Xaa is p-aminomethyl-L-phenylalanine (pAF)
<220> FEATURE:
<221> NAME/KEY: MISC_FEATURE
<222> LOCATION: (12)..(12)
<223> OTHER INFORMATION: pAF conjugated to   PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide
```

<400> SEQUENCE: 24

His Xaa Gln Gly Thr Phe Thr Ser Asp Tyr Ser Xaa Tyr Leu Asp Glu
1               5                   10                  15

Arg Ala Ala Gln Asp Phe Val Gln Trp Leu Xaa Asp Thr
            20                  25

<210> SEQ ID NO 25
<211> LENGTH: 29
<212> TYPE: PRT
<213> ORGANISM: Artificial sequence
<220> FEATURE:
<223> OTHER INFORMATION: Peptide TP419
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
<220> FEATURE:
<221> NAME/KEY: MISC_FEATURE
<222> LOCATION: (12)..(12)
<223> OTHER INFORMATION: Xaa is p-aminomethyl-L-phenylalanine (pAF)
<220> FEATURE:
<221> NAME/KEY: MISC_FEATURE
<222> LOCATION: (12)..(12)
<223> OTHER INFORMATION: pAF conjugated to PEG2PEG2-gammaGlu-C16-OH
<220> FEATURE:
<221> NAME/KEY: MISC_FEATURE
<222> LOCATION: (16)..(16)
<223> OTHER INFORMATION: Xaa is alpha-alpha-aminoisobutyric acid (aib)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 25

His Xaa Gln Gly Thr Phe Thr Ser Asp Tyr Ser Xaa Tyr Leu Asp Xaa
1               5                   10                  15

Arg Ala Ala Gln Asp Phe Val Gln Trp Leu Xaa Asp Thr
            20                  25

<210> SEQ ID NO 26
<211> LENGTH: 29
<212> TYPE: PRT
<213> ORGANISM: Artificial sequence
<220> FEATURE:
<223> OTHER INFORMATION: Peptide TP422
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
<220> FEATURE:
<221> NAME/KEY: MISC_FEATURE
<222> LOCATION: (20)..(20)
<223> OTHER INFORMATION: Xaa is p-aminomethyl-L-phenylalanine (pAF)
<220> FEATURE:
<221> NAME/KEY: MISC_FEATURE
<222> LOCATION: (20)..(20)
<223> OTHER INFORMATION: pAF conjugated to PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 26

His Xaa Gln Gly Thr Phe Thr Ser Asp Tyr Ser Lys Tyr Leu Asp Glu
1               5                   10                  15

Arg Ala Ala Xaa Asp Phe Val Gln Trp Leu Leu Lys Thr

```
                20                  25

<210> SEQ ID NO 27
<211> LENGTH: 29
<212> TYPE: PRT
<213> ORGANISM: Artificial sequence
<220> FEATURE:
<223> OTHER INFORMATION: Peptide TP423
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Xaa is p-aminomethyl-L-phenylalanine (pAF)
<220> FEATURE:
<221> NAME/KEY: MISC_FEATURE
<222> LOCATION: (21)..(21)
<223> OTHER INFORMATION: pAF conjugated to  PEG2PEG2-gammaGlu-C16-OH
<220> FEATURE:
<221> NAME/KEY: MISC_FEATURE
<222> LOCATION: (29)..(29)
<223> OTHER INFORMATION: C-terminal amide

<400> SEQUENCE: 27

His Xaa Gln Gly Thr Phe Thr Ser Asp Tyr Ser Lys Tyr Leu Asp Glu
1               5                   10                  15

Arg Ala Ala Gln Xaa Phe Val Gln Trp Leu Leu Lys Thr
                20                  25

<210> SEQ ID NO 28
<211> LENGTH: 29
<212> TYPE: PRT
<213> ORGANISM: Artificial sequence
<220> FEATURE:
<223> OTHER INFORMATION: Peptide TP424
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (10)..(10)
<223> OTHER INFORMATION: Xaa is p-aminomethyl-L-phenylalanine (pAF)
<220> FEATURE:
<221> NAME/KEY: MISC_FEATURE
<222> LOCATION: (10)..(10)
<223> OTHER INFORMATION: pAF conjugated to  PEG2PEG2-gammaGlu-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 28

His Xaa Gln Gly Thr Phe Thr Ser Asp Xaa Ser Lys Tyr Leu Asp Ala
1               5                   10                  15

Arg Ala Ala Gln Asp Phe Val Gln Trp Leu Xaa Asp Thr
                20                  25

<210> SEQ ID NO 29
<211> LENGTH: 29
<212> TYPE: PRT
<213> ORGANISM: Artificial sequence
<220> FEATURE:
<223> OTHER INFORMATION: Peptide TP440
<220> FEATURE:
<221> NAME/KEY: MISC_FEATURE
```

```
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 29

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Asp Thr
            20                  25

<210> SEQ ID NO 30
<211> LENGTH: 29
<212> TYPE: PRT
<213> ORGANISM: Artificial sequence
<220> FEATURE:
<223> OTHER INFORMATION: Peptide TP441
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Lys conjugated to PEG2PEG2-gammaGlu-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 30

His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Xaa Asp Thr
            20                  25

<210> SEQ ID NO 31
<211> LENGTH: 29
<212> TYPE: PRT
<213> ORGANISM: Artificial sequence
<220> FEATURE:
<223> OTHER INFORMATION: Peptide TPP442
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Xaa is p-aminomethyl-L-phenylalanine (pAF)
<220> FEATURE:
<221> NAME/KEY: MISC_FEATURE
<222> LOCATION: (20)..(20)
<223> OTHER INFORMATION: pAF conjugated to  PEG2PEG2-gammaGlu-C18-OH
<220> FEATURE:
<221> NAME/KEY: MISC_FEATURE
<222> LOCATION: (29)..(29)
<223> OTHER INFORMATION: C-terminal amide
```

```
<400> SEQUENCE: 31

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Leu Asp Thr
            20                  25

<210> SEQ ID NO 32
<211> LENGTH: 29
<212> TYPE: PRT
<213> ORGANISM: Artificial sequence
<220> FEATURE:
<223> OTHER INFORMATION: Peptide TPP443
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Xaa is p-aminomethyl-L-phenylalanine (pAF)
<220> FEATURE:
<221> NAME/KEY: MISC_FEATURE
<222> LOCATION: (21)..(21)
<223> OTHER INFORMATION: pAF conjugated to  PEG2PEG2-gammaGlu-C18-OH
<220> FEATURE:
<221> NAME/KEY: MISC_FEATURE
<222> LOCATION: (29)..(29)
<223> OTHER INFORMATION: C-terminal amide

<400> SEQUENCE: 32

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Asp Thr
            20                  25

<210> SEQ ID NO 33
<211> LENGTH: 29
<212> TYPE: PRT
<213> ORGANISM: Artificial sequence
<220> FEATURE:
<223> OTHER INFORMATION: Peptide TPP458
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid (aMD)
<220> FEATURE:
<221> NAME/KEY: MISC_FEATURE
<222> LOCATION: (29)..(29)
<223> OTHER INFORMATION: C-terminal amide

<400> SEQUENCE: 33

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Xaa Thr
            20                  25

<210> SEQ ID NO 34
<211> LENGTH: 29
```

```
<212> TYPE: PRT
<213> ORGANISM: Artificial sequence
<220> FEATURE:
<223> OTHER INFORMATION: Peptide TPP461
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (12)..(12)
<223> OTHER INFORMATION: Xaa is 2-aminocyclopentane carboxylic acid
<220> FEATURE:
<221> NAME/KEY: MISC_FEATURE
<222> LOCATION: (16)..(16)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C18-OH
<220> FEATURE:
<221> NAME/KEY: MISC_FEATURE
<222> LOCATION: (24)..(24)
<223> OTHER INFORMATION: Xaa is 2-aminocyclopentane carboxylic acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 34

His Xaa Gln Gly Thr Phe Thr Ser Asp Tyr Ser Xaa Tyr Leu Asp Xaa
1               5                   10                  15

Arg Ala Ala Lys Asp Phe Val Xaa Trp Leu Xaa Asp Thr
            20                  25

<210> SEQ ID NO 35
<211> LENGTH: 29
<212> TYPE: PRT
<213> ORGANISM: Artificial sequence
<220> FEATURE:
<223> OTHER INFORMATION: Peptide TPP467
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2
     PEG2PEG2-gammaGlu-C18-OH
<220> FEATURE:
<221> NAME/KEY: MISC_FEATURE
<222> LOCATION: (21)..(21)
<223> OTHER INFORMATION: Xaa is alpha-Methyl-L-Aspartic acid (aMD)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 35

His Xaa Gln Gly Thr Phe Thr Ser Asp Tyr Ser Lys Tyr Leu Asp Ala
1               5                   10                  15

Arg Ala Ala Lys Xaa Phe Val Gln Trp Leu Xaa Asp Thr
            20                  25
```

```
<210> SEQ ID NO 36
<211> LENGTH: 29
<212> TYPE: PRT
<213> ORGANISM: Artificial sequence
<220> FEATURE:
<223> OTHER INFORMATION: Peptide TPP470
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (12)..(12)
<223> OTHER INFORMATION: Xaa is 2-aminocyclopentane carboxylic acid
<220> FEATURE:
<221> NAME/KEY: MISC_FEATURE
<222> LOCATION: (16)..(16)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (24)..(24)
<223> OTHER INFORMATION: Xaa is 2-aminocyclopentane carboxylic acid
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 36

His Xaa Gln Gly Thr Phe Thr Ser Asp Tyr Ser Xaa Tyr Leu Asp Xaa
1               5                   10                  15

Arg Ala Ala Lys Asp Phe Val Xaa Trp Leu Xaa Asp Thr
            20                  25

<210> SEQ ID NO 37
<211> LENGTH: 29
<212> TYPE: PRT
<213> ORGANISM: Artificial sequence
<220> FEATURE:
<223> OTHER INFORMATION: Peptide TPP472
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (9)..(9)
<223> OTHER INFORMATION: Xaa is alpha-Methyl-L-Aspartic acid (aMD)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 37

His Xaa Gln Gly Thr Phe Thr Ser Xaa Tyr Ser Lys Tyr Leu Asp Ala
1               5                   10                  15

Arg Ala Ala Lys Asp Phe Val Gln Trp Leu Xaa Asp Thr
            20                  25
```

```
<210> SEQ ID NO 38
<211> LENGTH: 29
<212> TYPE: PRT
<213> ORGANISM: Artificial sequence
<220> FEATURE:
<223> OTHER INFORMATION: Peptide TPP473
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (14)..(14)
<223> OTHER INFORMATION: Xaa is alpha-Methyl-L-Leucine (aML)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 38

His Xaa Gln Gly Thr Phe Thr Ser Asp Tyr Ser Lys Tyr Xaa Asp Ala
1               5                   10                  15

Arg Ala Ala Lys Asp Phe Val Gln Trp Leu Xaa Asp Thr
            20                  25

<210> SEQ ID NO 39
<211> LENGTH: 29
<212> TYPE: PRT
<213> ORGANISM: Artificial sequence
<220> FEATURE:
<223> OTHER INFORMATION: Peptide TPP474
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (22)..(22)
<223> OTHER INFORMATION: Xaa is alpha-Methyl-L-phenylalanine (aMF)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 39

His Xaa Gln Gly Thr Phe Thr Ser Asp Tyr Ser Lys Tyr Leu Asp Ala
1               5                   10                  15

Arg Ala Ala Lys Asp Xaa Val Gln Trp Leu Xaa Asp Thr
            20                  25

<210> SEQ ID NO 40
<211> LENGTH: 29
<212> TYPE: PRT
<213> ORGANISM: Artificial sequence
<220> FEATURE:
<223> OTHER INFORMATION: Peptide TPP475
```

```
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (26)..(26)
<223> OTHER INFORMATION: Xaa is alpha-Methyl-L-Leucine (aML)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 40

His Xaa Gln Gly Thr Phe Thr Ser Asp Tyr Ser Lys Tyr Leu Asp Ala
1               5                   10                  15

Arg Ala Ala Lys Asp Phe Val Gln Trp Xaa Xaa Asp Thr
            20                  25

<210> SEQ ID NO 41
<211> LENGTH: 29
<212> TYPE: PRT
<213> ORGANISM: Artificial sequence
<220> FEATURE:
<223> OTHER INFORMATION: Peptide TPP476
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C16-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is alpha-Methyl-L-Aspartic acid (aMD)
<220> FEATURE:
<221> NAME/KEY: MISC_FEATURE
<222> LOCATION: (29)..(29)
<223> OTHER INFORMATION: C-terminal amide

<400> SEQUENCE: 41

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Xaa Thr
            20                  25

<210> SEQ ID NO 42
<211> LENGTH: 29
<212> TYPE: PRT
<213> ORGANISM: Artificial sequence
<220> FEATURE:
<223> OTHER INFORMATION: Peptide TP477
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
```

```
<223> OTHER INFORMATION: Lys conjugated to PEG2PEG2-gammaGlu-C16-OH
<220> FEATURE:
<221> NAME/KEY: MISC_FEATURE
<222> LOCATION: (21)..(21)
<223> OTHER INFORMATION: Xaa is alpha-Methyl-L-Aspartic acid (aMD)
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 42

His Xaa Gln Gly Thr Phe Thr Ser Asp Tyr Ser Lys Tyr Leu Asp Ala
1               5                  10                  15

Arg Ala Ala Lys Xaa Phe Val Gln Trp Leu Xaa Asp Thr
            20                  25

<210> SEQ ID NO 43
<211> LENGTH: 29
<212> TYPE: PRT
<213> ORGANISM: Artificial sequence
<220> FEATURE:
<223> OTHER INFORMATION: Peptide TP491
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C20-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 43

His Xaa Gln Gly Thr Phe Thr Ser Asp Tyr Ser Lys Tyr Leu Asp Ala
1               5                  10                  15

Arg Ala Ala Lys Asp Phe Val Gln Trp Leu Xaa Asp Thr
            20                  25

<210> SEQ ID NO 44
<211> LENGTH: 29
<212> TYPE: PRT
<213> ORGANISM: Artificial sequence
<220> FEATURE:
<223> OTHER INFORMATION: Peptide TP492
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Lys conjugated to PEG2PEG2-gammaGlu-C20-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 44
```

```
His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Xaa Asp Thr
            20                  25

<210> SEQ ID NO 45
<211> LENGTH: 29
<212> TYPE: PRT
<213> ORGANISM: Artificial sequence
<220> FEATURE:
<223> OTHER INFORMATION: Peptide TP493
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C19-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 45

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Asp Thr
            20                  25

<210> SEQ ID NO 46
<211> LENGTH: 29
<212> TYPE: PRT
<213> ORGANISM: Artificial sequence
<220> FEATURE:
<223> OTHER INFORMATION: Peptide TP494
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Lys conjugated to PEG2PEG2-gammaGlu-C19-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 46

His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Xaa Asp Thr
            20                  25

<210> SEQ ID NO 47
<211> LENGTH: 29
<212> TYPE: PRT
<213> ORGANISM: Artificial sequence
<220> FEATURE:
<223> OTHER INFORMATION: Peptide TP495
<220> FEATURE:
```

```
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to
      PEG2PEG2PEG2PEG2-gammaGlu-C17-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 47

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Asp Thr
            20                  25

<210> SEQ ID NO 48
<211> LENGTH: 29
<212> TYPE: PRT
<213> ORGANISM: Artificial sequence
<220> FEATURE:
<223> OTHER INFORMATION: Peptide TP496
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (21)..(21)
<223> OTHER INFORMATION: Lys conjugated to PEG2PEG2-gammaGlu-C17-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 48

His Xaa Gln Gly Thr Phe Thr Ser Asp Tyr Ser Lys Tyr Leu Asp Ala
1               5                   10                  15

Arg Ala Ala Gln Lys Phe Val Gln Trp Leu Xaa Asp Thr
            20                  25

<210> SEQ ID NO 49
<211> LENGTH: 29
<212> TYPE: PRT
<213> ORGANISM: Artificial sequence
<220> FEATURE:
<223> OTHER INFORMATION: Peptide TP560
<220> FEATURE:
<221> NAME/KEY: MISC_FEATURE
<222> LOCATION: (2)..(2)
<223> OTHER INFORMATION: Xaa is  alpha-alpha-aminoisobutyric acid (aib)
<220> FEATURE:
<221> NAME/KEY: MISC_FEATURE
<222> LOCATION: (20)..(20)
<223> OTHER INFORMATION: Lys conjugated to PEG2PEG2-gammaGlu-C14-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
```

<223> OTHER INFORMATION: C-terminal amide

<400> SEQUENCE: 49

His Xaa Gln Gly Thr Phe Thr Ser Asp Tyr Ser Lys Tyr Leu Asp Ala
1               5                   10                  15

Arg Ala Ala Lys Asp Phe Val Gln Trp Leu Xaa Asp Thr
            20                  25

<210> SEQ ID NO 50
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: for each co-agonist peptide, only one of Xaa10,
      Xaa12, Xaa20, or Xaa21 is conjugated to a fatty diacid
<220> FEATURE:
<221> NAME/KEY: MISC_FEATURE
<222> LOCATION: (1)..(30)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is aminoisobutyric acid (aib) or D-Ser or
      alpha-Methyl-L-Serine (alpha-MS)
<220> FEATURE:
<221> NAME/KEY: MISC_FEATURE
<222> LOCATION: (9)..(9)
<223> OTHER INFORMATION: Xaa is Asp or alpha-Methyl-L-Aspartic acid
      (alpha-MD)
<220> FEATURE:
<221> NAME/KEY: MISC_FEATURE
<222> LOCATION: (10)..(10)
<223> OTHER INFORMATION: Xaa is Lys conjugated to a fatty diacid or
      p-aminomethyl-L-phenylalanine (pAF) conjugated to a fatty diacid
      or Tyr
<220> FEATURE:
<221> NAME/KEY: MISC_FEATURE
<222> LOCATION: (12)..(12)
<223> OTHER INFORMATION: Xaa is Lys conjugated to a fatty diacid, pAF
      conjugated to a fatty diacid, Lys, or 2-aminocyclopentane
      carboxylic acid or (1S,2S)-Fmoc-2-aminocyclopentane carboxylic
      acid
<220> FEATURE:
<221> NAME/KEY: MISC_FEATURE
<222> LOCATION: (14)..(14)
<223> OTHER INFORMATION: Xaa is Leu or alpha-Leu (alpha-ML)
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (20)..(20)
<223> OTHER INFORMATION: Xaa is Lys is conjugated to a fatty diacid,
      pAF conjugated to a fatty diacid, or Gln
<220> FEATURE:
<221> NAME/KEY: MISC_FEATURE
<222> LOCATION: (21)..(21)
<223> OTHER INFORMATION: Xaa is Lys conjugated to a fatty diacid or pAF
      conjugated to a fatty diacid, Asp, or alpha-MD
<220> FEATURE:
<221> NAME/KEY: MISC_FEATURE
<222> LOCATION: (22)..(22)
<223> OTHER INFORMATION: Xaa is Phe or alpha-Methyl-L-phenylalanine
      (alpha-MF)
<220> FEATURE:
<221> NAME/KEY: MISC_FEATURE
<222> LOCATION: (24)..(24)
<223> OTHER INFORMATION: Xaa is Gln or 2-aminocyclopentane carboxylic
      acid or (1S,2S)-Fmoc-2-aminocyclopentane carboxylic acid or Lys
      conjugated to a fatty diacid or pAF conjugated to a fatty diacid
<220> FEATURE:

```
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa  is Asp, or alpha-MD, or
      alpha-Methyl-L-Tryptophan (alpha-MW), Lys, or Ala, or Lys
      conjugated to a fatty diacid, or pAF conjugated to a fatty diacid
<220> FEATURE:
<221> NAME/KEY: MISC_FEATURE
<222> LOCATION: (30)..(30)
<223> OTHER INFORMATION: Xaa  is absent or Lys linked at the C-terminus
      to gamma-Glu when Xaa27 is Leu and Xaa28 is Ala

<400> SEQUENCE: 50

His Xaa Gln Gly Thr Phe Thr Ser Xaa Xaa Ser Xaa Tyr Xaa Asp Xaa
1               5                   10                  15

Arg Ala Ala Xaa Xaa Xaa Val Xaa Trp Leu Xaa Xaa Thr Xaa
            20                  25                  30

<210> SEQ ID NO 51
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
      or D-Ser
<220> FEATURE:
<221> NAME/KEY: MISC_FEATURE
<222> LOCATION: (10)..(10)
<223> OTHER INFORMATION: Xaa  is Lys conjugated to a C16 or C18 or C20
      fatty diacid or p-aminomethyl-L-phenylalanine (pAF) conjugated to
      a C16 or C18 or C20 fatty diacid
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa is absent or Lys conjugated to gamma-Glu
      when Xaa27 is Leu and Xaa28 is Ala

<400> SEQUENCE: 51

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Xaa Xaa Thr Xaa
            20                  25                  30

<210> SEQ ID NO 52
<211> LENGTH: 29
<212> TYPE: PRT
<213> ORGANISM: Artificial sequence
<220> FEATURE:
<223> OTHER INFORMATION: Co-agonist
<220> FEATURE:
```

```
<221> NAME/KEY: MISC_FEATURE
<222> LOCATION: (1)..(29)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
      or D-Ser
<220> FEATURE:
<221> NAME/KEY: MISC_FEATURE
<222> LOCATION: (12)..(12)
<223> OTHER INFORMATION: Xaa is Lys conjugated to a C16 or C18 fatty
      diacid or p-aminomethyl-L-phenylalanine (pAF) conjugated to a C16
      or C18 or C20 fatty diacid
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (27)..(27)
<223> OTHER INFORMATION: Xaa is L-Met sulphone or Leucine

<400> SEQUENCE: 52

His Xaa Gln Gly Thr Phe Thr Ser Asp Tyr Ser Xaa Tyr Leu Asp Xaa
1               5                   10                  15

Arg Ala Ala Gln Asp Phe Val Gln Trp Leu Xaa Asp Thr
            20                  25

<210> SEQ ID NO 53
<211> LENGTH: 29
<212> TYPE: PRT
<213> ORGANISM: Artificial sequence
<220> FEATURE:
<223> OTHER INFORMATION: Co-qgonist
<220> FEATURE:
<221> NAME/KEY: MISC_FEATURE
<222> LOCATION: (1)..(29)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
      or D-Ser
<220> FEATURE:
<221> NAME/KEY: MISC_FEATURE
<222> LOCATION: (9)..(9)
<223> OTHER INFORMATION: Xaa is Asp or alpha-MD
<220> FEATURE:
<221> NAME/KEY: MISC_FEATURE
<222> LOCATION: (12)..(12)
<223> OTHER INFORMATION: Xaa is Lys or 2-aminocyclopentane carboxylic
      acid or (1S,2S)-Fmoc-2-aminocyclopentane carboxylic acid
<220> FEATURE:
<221> NAME/KEY: MISC_FEATURE
<222> LOCATION: (14)..(14)
<223> OTHER INFORMATION: Xaa is Leu or alpha-Methyl-L-Aspartic acid
      (alpha-MD)
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (20)..(20)
<223> OTHER INFORMATION: Xaa is Lys conjugated to a C16, C17, C18, C19,
      or C20 fatty diacid or p-aminomethyl-L-phenylalanine (pAF)
      conjugated to a C16, C17, C18, C19, or C20 fatty diacid
<220> FEATURE:
<221> NAME/KEY: MISC_FEATURE
<222> LOCATION: (21)..(21)
<223> OTHER INFORMATION: Xaa is Asp or alpha-MD
<220> FEATURE:
<221> NAME/KEY: MISC_FEATURE
<222> LOCATION: (22)..(22)
<223> OTHER INFORMATION: Xaa is Phe or alpha-Methyl-L-phenylalanine
```

```
              (alpha-MF)
<220> FEATURE:
<221> NAME/KEY: MISC_FEATURE
<222> LOCATION: (24)..(24)
<223> OTHER INFORMATION: Xaa  Gln  or 2-aminocyclopentane carboxylic
      acid  or (1S,2S)-Fmoc-2-aminocyclopentane carboxylic acid
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or alpha-MD

<400> SEQUENCE: 53

His Xaa Gln Gly Thr Phe Thr Ser Xaa Tyr Ser Xaa Tyr Xaa Asp Xaa
1               5                   10                  15

Arg Ala Ala Xaa Xaa Xaa Val Xaa Trp Xaa Xaa Xaa Thr
            20                  25

<210> SEQ ID NO 54
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa  is alpha-alpha-aminoisobutyric acid (aib)
      or D-Ser
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (21)..(21)
<223> OTHER INFORMATION: Xaa is Lys conjugated to a C16, C17, C18, C19,
      or C20 fatty diacid or p-aminomethyl-L-phenylalanine (pAF)
      conjugated to a C16, C17, C18, C19, or C20 fatty diacid
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa  is absent or Lys conjugated to gamma-Glu
      when Xaa27 is Leu and Xaa28 is Ala

<400> SEQUENCE: 54

His Xaa Gln Gly Thr Phe Thr Ser Asp Tyr Ser Lys Tyr Leu Asp Xaa
1               5                   10                  15

Arg Ala Ala Gln Xaa Phe Val Gln Trp Leu Xaa Xaa Thr Xaa
            20                  25                  30

<210> SEQ ID NO 55
<211> LENGTH: 30
<212> TYPE: PRT
<213> ORGANISM: Artificial sequence
<220> FEATURE:
<223> OTHER INFORMATION: Co-agonist
<220> FEATURE:
```

```
<221> NAME/KEY: MISC_FEATURE
<222> LOCATION: (1)..(30)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
      or D-Ser
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (24)..(24)
<223> OTHER INFORMATION: Xaa is Lys or pAF conjugated to a C16, C17,
      C18, C19, or C20 fatty diacid
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Asp, Lys, or Ala
<220> FEATURE:
<221> NAME/KEY: MISC_FEATURE
<222> LOCATION: (30)..(30)
<223> OTHER INFORMATION: Xaa is absent or Lys conjugated to gamma-Glu
      when Xaa27 is Leu and Xaa28 is Ala

<400> SEQUENCE: 55

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Xaa Thr Xaa
            20                  25                  30

<210> SEQ ID NO 56
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: with the proviso that for each co-agonist
      peptide, only one of Xaa10, Xaa12, Xaa20, Xaa21, or Xaa24 is
      conjugated to a fatty diacid
<220> FEATURE:
<221> NAME/KEY: MISC_FEATURE
<222> LOCATION: (1)..(30)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
      or D-Ser
<220> FEATURE:
<221> NAME/KEY: MISC_FEATURE
<222> LOCATION: (9)..(9)
<223> OTHER INFORMATION: Xaa is Asp or alpha-Methyl-L-Aspartic acid
      (alpha-MD)
<220> FEATURE:
<221> NAME/KEY: MISC_FEATURE
<222> LOCATION: (10)..(10)
<223> OTHER INFORMATION: Xaa is Lys conjugated to a fatty diacid or Tyr
<220> FEATURE:
<221> NAME/KEY: MISC_FEATURE
<222> LOCATION: (12)..(12)
<223> OTHER INFORMATION: Xaa is Lys conjugated to a fatty diacid, or
      2-aminocyclopentane carboxylic acid or
      (1S,2S)-Fmoc-2-aminocyclopentane carboxylic acid
<220> FEATURE:
<221> NAME/KEY: MISC_FEATURE
<222> LOCATION: (14)..(14)
```

```
<223> OTHER INFORMATION: Xaa is Leu or alpha-MD
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (20)..(20)
<223> OTHER INFORMATION: Xaa is Lys is conjugated to a fatty diacid,
      Asp, or alpha-MD
<220> FEATURE:
<221> NAME/KEY: MISC_FEATURE
<222> LOCATION: (21)..(21)
<223> OTHER INFORMATION: Xaa is Lys conjugated to a fatty diacid, Asp,
      or alpha-MD
<220> FEATURE:
<221> NAME/KEY: MISC_FEATURE
<222> LOCATION: (22)..(22)
<223> OTHER INFORMATION: Xaa is Phe or alpha-Methyl-L-phenylalanine
      (alpha-MF)
<220> FEATURE:
<221> NAME/KEY: MISC_FEATURE
<222> LOCATION: (24)..(24)
<223> OTHER INFORMATION: Xaa is Gln or 2-aminocyclopentane carboxylic
      acid or (1S,2S)-Fmoc-2-aminocyclopentane carboxylic acid or Lys
      conjugated to a fatty diacid
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Asp, Lys, or Ala
<220> FEATURE:
<221> NAME/KEY: MISC_FEATURE
<222> LOCATION: (30)..(30)
<223> OTHER INFORMATION: Xaa is absent or Lys conjugated to gamma-Glu
      when Xaa27 is Leu and Xaa28 is Ala

<400> SEQUENCE: 56

His Xaa Gln Gly Thr Phe Thr Ser Xaa Xaa Ser Xaa Tyr Xaa Asp Xaa
1               5                   10                  15

Arg Ala Ala Xaa Xaa Xaa Val Xaa Trp Leu Xaa Xaa Thr Xaa
            20                  25                  30

<210> SEQ ID NO 57
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is alpha-alpha-aminoisobutyric acid (aib)
      or D-Ser
<220> FEATURE:
<221> NAME/KEY: MISC_FEATURE
<222> LOCATION: (10)..(10)
<223> OTHER INFORMATION: Xaa is Lys conjugated to a C16 or C18 or C20
      fatty diacid
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
```

```
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa  is absent or Lys conjugated to gamma-Glu
      when Xaa27 is Leu and Xaa28 is Ala

<400> SEQUENCE: 57

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Xaa Xaa Thr Xaa
            20                  25                  30

<210> SEQ ID NO 58
<211> LENGTH: 29
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(29)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (12)..(12)
<223> OTHER INFORMATION: Xaa  is Lys conjugated to a C16 or C18 or C20
      fatty diacid
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (27)..(27)
<223> OTHER INFORMATION: Xaa  is L-Met sulphone or Leucine

<400> SEQUENCE: 58

His Xaa Gln Gly Thr Phe Thr Ser Asp Tyr Ser Xaa Tyr Leu Asp Xaa
1               5                   10                  15

Arg Ala Ala Gln Asp Phe Val Gln Trp Leu Xaa Asp Thr
            20                  25

<210> SEQ ID NO 59
<211> LENGTH: 29
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(29)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (9)..(9)
<223> OTHER INFORMATION: Xaa  is Asp or alpha-MD
<220> FEATURE:
<221> NAME/KEY: MISC_FEATURE
<222> LOCATION: (12)..(12)
<223> OTHER INFORMATION: Xaa is Lys  or 2-aminocyclopentane carboxylic
      acid  or (1S,2S)-Fmoc-2-aminocyclopentane carboxylic acid
```

```
<220> FEATURE:
<221> NAME/KEY: MISC_FEATURE
<222> LOCATION: (14)..(14)
<223> OTHER INFORMATION: Xaa  is Leu or alpha-Methyl-L-Aspartic acid
      (alpha-MD)
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (20)..(20)
<223> OTHER INFORMATION: Xaa  is Lys conjugated to a C16, C17, C18, C19,
      or C20 fatty diacid
<220> FEATURE:
<221> NAME/KEY: MISC_FEATURE
<222> LOCATION: (21)..(21)
<223> OTHER INFORMATION: Xaa  is Asp or alpha-MD
<220> FEATURE:
<221> NAME/KEY: MISC_FEATURE
<222> LOCATION: (22)..(22)
<223> OTHER INFORMATION: Xaa  is Phe or alpha-Methyl-L-phenylalanine
      (alpha-MF);
<220> FEATURE:
<221> NAME/KEY: MISC_FEATURE
<222> LOCATION: (24)..(24)
<223> OTHER INFORMATION: Xaa  Gln  or 2-aminocyclopentane carboxylic
      acid  or (1S,2S)-Fmoc-2-aminocyclopentane carboxylic acid
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or alpha-MD

<400> SEQUENCE: 59

His Xaa Gln Gly Thr Phe Thr Ser Xaa Tyr Ser Xaa Tyr Xaa Asp Xaa
1               5                   10                  15

Arg Ala Ala Xaa Xaa Xaa Val Xaa Trp Xaa Xaa Xaa Thr
            20                  25

<210> SEQ ID NO 60
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (21)..(21)
<223> OTHER INFORMATION: Xaa  is Lys conjugated to a C16, C17, C18, C19,
      or C20 fatty diacid
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
```

```
<221> NAME/KEY: MISC_FEATURE
<222> LOCATION: (30)..(30)
<223> OTHER INFORMATION: Xaa  is absent or Lys conjugated to gamma-Glu
      when Xaa27 is Leu and Xaa28 is Ala

<400> SEQUENCE: 60

His Xaa Gln Gly Thr Phe Thr Ser Asp Tyr Ser Lys Tyr Leu Asp Xaa
1               5                   10                  15

Arg Ala Ala Gln Xaa Phe Val Gln Trp Leu Xaa Xaa Thr Xaa
            20                  25                  30

<210> SEQ ID NO 61
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (24)..(24)
<223> OTHER INFORMATION: Xaa  is Lys conjugated to a C16, C17, C18, C19,
      or C20 fatty diacid
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa  is absent or Lys conjugated to gamma-Glu
      when Xaa27 is Leu and Xaa28 is Ala

<400> SEQUENCE: 61

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Xaa Thr Xaa
            20                  25                  30

<210> SEQ ID NO 62
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: with the proviso that for each co-agonist
      peptide, only one of Xaa10, Xaa12, Xaa20,  Xaa21, or Xaa24 is
      conjugated to a fatty diacid
<220> FEATURE:
<221> NAME/KEY: MISC_FEATURE
<222> LOCATION: (1)..(30)
<223> OTHER INFORMATION: C-terminus amino acid  of peptide is amidated
<220> FEATURE:
<221> NAME/KEY: MISC_FEATURE
```

```
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (9)..(9)
<223> OTHER INFORMATION: Xaa  is Asp or alpha-Methyl-L-Aspartic acid
      (alpha-MD)
<220> FEATURE:
<221> NAME/KEY: MISC_FEATURE
<222> LOCATION: (10)..(10)
<223> OTHER INFORMATION: Xaa  is pAF conjugated to a fatty diacid or Tyr
<220> FEATURE:
<221> NAME/KEY: MISC_FEATURE
<222> LOCATION: (12)..(12)
<223> OTHER INFORMATION: Xaa  is pAF conjugated to a fatty diacid,  or
      2-aminocyclopentane carboxylic acid  or
      (1S,2S)-Fmoc-2-aminocyclopentane carboxylic acid
<220> FEATURE:
<221> NAME/KEY: MISC_FEATURE
<222> LOCATION: (14)..(14)
<223> OTHER INFORMATION: Xaa  is Leu or alpha-MD; X16 is aib, Ala, or
      Glu
<220> FEATURE:
<221> NAME/KEY: MISC_FEATURE
<222> LOCATION: (20)..(20)
<223> OTHER INFORMATION: Xaa  is pAF is conjugated to a fatty diacid,
      Asp, or alpha-MD
<220> FEATURE:
<221> NAME/KEY: MISC_FEATURE
<222> LOCATION: (21)..(21)
<223> OTHER INFORMATION: Xaa  is pAF conjugated to a fatty diacid, Asp,
      or alpha-MD
<220> FEATURE:
<221> NAME/KEY: MISC_FEATURE
<222> LOCATION: (22)..(22)
<223> OTHER INFORMATION: Xaa  is Phe or alpha-Methyl-L-phenylalanine
      (alpha-MF)
<220> FEATURE:
<221> NAME/KEY: MISC_FEATURE
<222> LOCATION: (24)..(24)
<223> OTHER INFORMATION: Xaa  is Gln  or 2-aminocyclopentane carboxylic
      acid  or (1S,2S)-Fmoc-2-aminocyclopentane carboxylic acid or pAF
      conjugated to a fatty diacid
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa  is absent or pAF conjugated to gamma-Glu
      when Xaa27 is Leu and Xaa28 is Ala

<400> SEQUENCE: 62

His Xaa Gln Gly Thr Phe Thr Ser Xaa Xaa Ser Xaa Tyr Xaa Asp Xaa
1               5                   10                  15

Arg Ala Ala Xaa Xaa Xaa Val Xaa Trp Leu Xaa Xaa Thr Xaa
            20                  25                  30

<210> SEQ ID NO 63
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid  of peptide is amidated
<220> FEATURE:
<221> NAME/KEY: MISC_FEATURE
```

```
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (10)..(10)
<223> OTHER INFORMATION: Xaa  is pAF conjugated to a C16 or C18 or C20
      fatty diacid
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa  is absent or Lys conjugated to gamma-Glu
      when Xaa27 is Leu and Xaa28 is Ala

<400> SEQUENCE: 63

His Xaa Gln Gly Thr Phe Thr Ser Asp Xaa Ser Lys Tyr Leu Asp Xaa
1               5                   10                  15

Arg Ala Ala Gln Asp Phe Val Gln Trp Leu Xaa Xaa Thr Xaa
            20                  25                  30

<210> SEQ ID NO 64
<211> LENGTH: 29
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(29)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (12)..(12)
<223> OTHER INFORMATION: Xaa  is pAF conjugated to a C16 or C18 or C20
      fatty diacid
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (27)..(27)
<223> OTHER INFORMATION: Xaa  is L-Met sulphone or Leucine

<400> SEQUENCE: 64

His Xaa Gln Gly Thr Phe Thr Ser Asp Tyr Ser Xaa Tyr Leu Asp Xaa
1               5                   10                  15

Arg Ala Ala Gln Asp Phe Val Gln Trp Leu Xaa Asp Thr
            20                  25

<210> SEQ ID NO 65
<211> LENGTH: 29
<212> TYPE: PRT
<213> ORGANISM: Artificial sequence
<220> FEATURE:
<223> OTHER INFORMATION: Co-agonist
```

```
<220> FEATURE:
<221> NAME/KEY: MISC_FEATURE
<222> LOCATION: (1)..(29)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is alpha-aminoisobutyric acid (aib) or
      D-Ser
<220> FEATURE:
<221> NAME/KEY: MISC_FEATURE
<222> LOCATION: (9)..(9)
<223> OTHER INFORMATION: Xaa is Asp or alpha-MD
<220> FEATURE:
<221> NAME/KEY: MISC_FEATURE
<222> LOCATION: (12)..(12)
<223> OTHER INFORMATION: Xaa is Lys or 2-aminocyclopentane carboxylic
      acid or (1S,2S)-Fmoc-2-aminocyclopentane carboxylic acid
<220> FEATURE:
<221> NAME/KEY: MISC_FEATURE
<222> LOCATION: (14)..(14)
<223> OTHER INFORMATION: Xaa is Leu or alpha-Methyl-L-Aspartic acid
      (alpha-MD)
<220> FEATURE:
<221> NAME/KEY: MISC_FEATURE
<222> LOCATION: (16)..(16)
<223> OTHER INFORMATION: Xaa is aib, Ala, or Glu
<220> FEATURE:
<221> NAME/KEY: MISC_FEATURE
<222> LOCATION: (20)..(20)
<223> OTHER INFORMATION: Xaa is pAF conjugated to a C16, C17, C18, C19,
      or C20 fatty diacid
<220> FEATURE:
<221> NAME/KEY: MISC_FEATURE
<222> LOCATION: (21)..(21)
<223> OTHER INFORMATION: Xaa is Asp or alpha-MD
<220> FEATURE:
<221> NAME/KEY: MISC_FEATURE
<222> LOCATION: (22)..(22)
<223> OTHER INFORMATION: Xaa is Phe or alpha-Methyl-L-phenylalanine
      (alpha-MF)
<220> FEATURE:
<221> NAME/KEY: MISC_FEATURE
<222> LOCATION: (24)..(24)
<223> OTHER INFORMATION: Xaa Gln or 2-aminocyclopentane carboxylic
      acid or (1S,2S)-Fmoc-2-aminocyclopentane carboxylic acid
<220> FEATURE:
<221> NAME/KEY: MISC_FEATURE
<222> LOCATION: (27)..(27)
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Asp, Lys, or alpha-MD

<400> SEQUENCE: 65

His Xaa Gln Gly Thr Phe Thr Ser Xaa Tyr Ser Xaa Tyr Xaa Asp Xaa
1               5                   10                  15

Arg Ala Ala Xaa Xaa Xaa Val Xaa Trp Xaa Xaa Xaa Thr
            20                  25

<210> SEQ ID NO 66
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid of peptide is amidated
<220> FEATURE:
<221> NAME/KEY: MISC_FEATURE
<222> LOCATION: (2)..(2)
<223> OTHER INFORMATION: Xaa is alpha-aminoisobutyric acid (aib) or
      D-Ser
```

```
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (21)..(21)
<223> OTHER INFORMATION: Xaa  is pAF conjugated to a C16, C17, C18, C19,
      or C20 fatty diacid
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa  is absent or Lys conjugated to gamma-Glu
      when Xaa27 is Leu and Xaa28 is Ala

<400> SEQUENCE: 66

His Xaa Gln Gly Thr Phe Thr Ser Asp Tyr Ser Lys Tyr Leu Asp Xaa
1               5                   10                  15

Arg Ala Ala Gln Xaa Phe Val Gln Trp Leu Xaa Xaa Thr Xaa
            20                  25                  30

<210> SEQ ID NO 67
<211> LENGTH: 30
<212> TYPE: PRT
<213> ORGANISM: Artificial sequence
<220> FEATURE:
<223> OTHER INFORMATION: Co-agonist
<220> FEATURE:
<221> NAME/KEY: MISC_FEATURE
<222> LOCATION: (1)..(30)
<223> OTHER INFORMATION: C-terminus amino acid  of peptide is amidated
<220> FEATURE:
<221> NAME/KEY: MISC_FEATURE
<222> LOCATION: (2)..(2)
<223> OTHER INFORMATION: Xaa  is alpha-aminoisobutyric acid (aib) or
      D-Ser
<220> FEATURE:
<221> NAME/KEY: MISC_FEATURE
<222> LOCATION: (16)..(16)
<223> OTHER INFORMATION: Xaa  is aib, Ala, or Glu
<220> FEATURE:
<221> NAME/KEY: MISC_FEATURE
<222> LOCATION: (24)..(24)
<223> OTHER INFORMATION: Xaa is pAF conjugated to a C16, C17, C18, C19,
      or C20 fatty diacid
<220> FEATURE:
<221> NAME/KEY: MISC_FEATURE
<222> LOCATION: (27)..(27)
<223> OTHER INFORMATION: Xaa  is L-Met sulphone or Leucine
<220> FEATURE:
<221> NAME/KEY: MISC_FEATURE
<222> LOCATION: (28)..(28)
<223> OTHER INFORMATION: Xaa  is Asp, Lys, or Ala
<220> FEATURE:
<221> NAME/KEY: MISC_FEATURE
<222> LOCATION: (30)..(30)
<223> OTHER INFORMATION: Xaa  is absent or Lys conjugated to gamma-Glu
      when Xaa27 is Leu and Xaa28 is Ala

<400> SEQUENCE: 67

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Xaa Thr Xaa
            20                  25                  30
```

-continued

```
<210> SEQ ID NO 68
<211> LENGTH: 29
<212> TYPE: PRT
<213> ORGANISM: Artificial sequence
<220> FEATURE:
<223> OTHER INFORMATION: TP575
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (16)..(16)
<223> OTHER INFORMATION: Xaa is  alpha-aminoisobutyric acid (aib)
<220> FEATURE:
<221> NAME/KEY: MISC_FEATURE
<222> LOCATION: (24)..(24)
<223> OTHER INFORMATION: Xaa is Lys conjugated to
      PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 68

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Xaa Asp Thr
            20                  25

<210> SEQ ID NO 69
<211> LENGTH: 29
<212> TYPE: PRT
<213> ORGANISM: Artificial sequence
<220> FEATURE:
<223> OTHER INFORMATION: TP564
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (16)..(16)
<223> OTHER INFORMATION: Xaa is  alpha-aminoisobutyric acid (aib)
<220> FEATURE:
<221> NAME/KEY: MISC_FEATURE
<222> LOCATION: (20)..(20)
<223> OTHER INFORMATION: Xaa is Lys conjugated to
      PEG2PEG2-gammaE-C20-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 69

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Xaa Asp Thr
            20                  25

<210> SEQ ID NO 70
<211> LENGTH: 29
<212> TYPE: PRT
<213> ORGANISM: Artificial sequence
<220> FEATURE:
```

<223> OTHER INFORMATION: TP598
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (20)..(20)
<223> OTHER INFORMATION: Xaa is Lys conjugated to
      PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 70

His Xaa Gln Gly Thr Phe Thr Ser Asp Tyr Ser Lys Tyr Leu Asp Ala
1               5                   10                  15

Lys Ala Ala Xaa Asp Phe Val Gln Trp Leu Xaa Asp Thr
            20                  25

<210> SEQ ID NO 71
<211> LENGTH: 29
<212> TYPE: PRT
<213> ORGANISM: Artificial sequence
<220> FEATURE:
<223> OTHER INFORMATION: TP608
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (21)..(21)
<223> OTHER INFORMATION: Xaa is Lys conjugated to
      PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is  alpha-Methyl-L-Aspartic acid
<220> FEATURE:
<221> NAME/KEY: MISC_FEATURE
<222> LOCATION: (29)..(29)
<223> OTHER INFORMATION: C-terminal amide

<400> SEQUENCE: 71

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Xaa Thr
            20                  25

<210> SEQ ID NO 72
<211> LENGTH: 29
<212> TYPE: PRT
<213> ORGANISM: Artificial sequence
<220> FEATURE:
<223> OTHER INFORMATION: TP655
<220> FEATURE:
<221> NAME/KEY: MISC_FEATURE
<222> LOCATION: (2)..(2)
<223> OTHER INFORMATION: Xaa is  alpha-Methyl-L-Aspartic acid
<220> FEATURE:
<221> NAME/KEY: MISC_FEATURE
<222> LOCATION: (21)..(21)
<223> OTHER INFORMATION: Xaa is Lys conjugated to

```
            PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 72

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Xaa Asp Thr
            20                  25

<210> SEQ ID NO 73
<211> LENGTH: 29
<212> TYPE: PRT
<213> ORGANISM: Artificial sequence
<220> FEATURE:
<223> OTHER INFORMATION: TP654
<220> FEATURE:
<221> NAME/KEY: MISC_FEATURE
<222> LOCATION: (2)..(2)
<223> OTHER INFORMATION: Xaa is  alpha-Methyl-L-Aspartic acid
<220> FEATURE:
<221> NAME/KEY: MISC_FEATURE
<222> LOCATION: (20)..(20)
<223> OTHER INFORMATION: 20 Xaa is Lys conjugated to
      PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 73

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Asp Thr
            20                  25

<210> SEQ ID NO 74
<211> LENGTH: 29
<212> TYPE: PRT
<213> ORGANISM: Artificial sequence
<220> FEATURE:
<223> OTHER INFORMATION: TP628
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (20)..(20)
<223> OTHER INFORMATION: Xaa is Lys conjugated to
      PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is  alpha-Methyl-L-Aspartic acid
<220> FEATURE:
<221> NAME/KEY: MISC_FEATURE
<222> LOCATION: (29)..(29)
<223> OTHER INFORMATION: C-terminal amide
```

<400> SEQUENCE: 74

His Xaa Gln Gly Thr Phe Thr Ser Asp Tyr Ser Lys Tyr Leu Asp Ala
1               5                   10                  15

Arg Ala Ala Xaa Asp Phe Val Gln Trp Leu Xaa Xaa Thr
            20                  25

<210> SEQ ID NO 75
<211> LENGTH: 29
<212> TYPE: PRT
<213> ORGANISM: Artificial sequence
<220> FEATURE:
<223> OTHER INFORMATION: TP609
<220> FEATURE:
<221> NAME/KEY: MISC_FEATURE
<222> LOCATION: (2)..(2)
<223> OTHER INFORMATION: Xaa is alpha-aminoisobutyric acid (aib)
<220> FEATURE:
<221> NAME/KEY: MISC_FEATURE
<222> LOCATION: (21)..(21)
<223> OTHER INFORMATION: Xaa is p-aminomethyl-L-phenylalanine conjugated
      to PEG2PEG2-gammaE-C18-OH
<220> FEATURE:
<221> NAME/KEY: MISC_FEATURE
<222> LOCATION: (28)..(28)
<223> OTHER INFORMATION: Xaa is alpha-Methyl-L-Aspartic acid
<220> FEATURE:
<221> NAME/KEY: MISC_FEATURE
<222> LOCATION: (29)..(29)
<223> OTHER INFORMATION: C-terminal amide

<400> SEQUENCE: 75

His Xaa Gln Gly Thr Phe Thr Ser Asp Tyr Ser Lys Tyr Leu Asp Ala
1               5                   10                  15

Arg Ala Ala Gln Xaa Phe Val Gln Trp Leu Leu Xaa Thr
            20                  25

<210> SEQ ID NO 76
<211> LENGTH: 29
<212> TYPE: PRT
<213> ORGANISM: Artificial sequence
<220> FEATURE:
<223> OTHER INFORMATION: TP597
<220> FEATURE:
<221> NAME/KEY: MISC_FEATURE
<222> LOCATION: (2)..(2)
<223> OTHER INFORMATION: Xaa is alpha-aminoisobutyric acid (aib)
<220> FEATURE:
<221> NAME/KEY: MISC_FEATURE
<222> LOCATION: (20)..(20)
<223> OTHER INFORMATION: Xaa is Lys conjugated to
      PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 76

His Xaa Gln Gly Thr Phe Thr Ser Asp Tyr Ser Lys Leu Leu Asp Ala
1               5                   10                  15

Arg Ala Ala Xaa Asp Phe Val Gln Trp Leu Xaa Asp Thr
            20                  25

<210> SEQ ID NO 77
<211> LENGTH: 29
<212> TYPE: PRT

<213> ORGANISM: Artificial sequence
<220> FEATURE:
<223> OTHER INFORMATION: TP604
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (27)..(27)
<223> OTHER INFORMATION: Xaa is  L-methionine sulphone
<220> FEATURE:
<221> NAME/KEY: MISC_FEATURE
<222> LOCATION: (28)..(28)
<223> OTHER INFORMATION: Xaa is p-aminomethyl-L-phenylalanine conjugated
      to PEG2PEG2-gammaE-C18-OH
<220> FEATURE:
<221> NAME/KEY: MISC_FEATURE
<222> LOCATION: (29)..(29)
<223> OTHER INFORMATION: C-terminal amide

<400> SEQUENCE: 77

His Xaa Gln Gly Thr Phe Thr Ser Asp Tyr Ser Lys Tyr Leu Asp Ala
1               5                   10                  15

Arg Ala Ala Gln Asp Phe Val Gln Trp Leu Xaa Xaa Thr
            20                  25

<210> SEQ ID NO 78
<211> LENGTH: 29
<212> TYPE: PRT
<213> ORGANISM: Artificial sequence
<220> FEATURE:
<223> OTHER INFORMATION: TP630
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (20)..(20)
<223> OTHER INFORMATION: Xaa is Lys conjugated to
      PEG2PEG2-gammaE-C18-OH
<220> FEATURE:
<221> NAME/KEY: MISC_FEATURE
<222> LOCATION: (25)..(25)
<223> OTHER INFORMATION: Xaa is  alpha-Methyl-L-Tryptophan
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (29)..(29)
<223> OTHER INFORMATION: C-terminal amide

<400> SEQUENCE: 78

His Xaa Gln Gly Thr Phe Thr Ser Asp Tyr Ser Lys Tyr Leu Asp Ala
1               5                   10                  15

Arg Ala Ala Xaa Asp Phe Val Gln Xaa Leu Xaa Asp Thr
            20                  25

<210> SEQ ID NO 79
<211> LENGTH: 31
<212> TYPE: PRT
<213> ORGANISM: Artificial sequence
<220> FEATURE:
<223> OTHER INFORMATION: TP640
<220> FEATURE:
<221> NAME/KEY: MISC_FEATURE
<222> LOCATION: (2)..(2)
<223> OTHER INFORMATION: Xaa is  alpha-aminoisobutyric acid (aib)
<220> FEATURE:
<221> NAME/KEY: MISC_FEATURE
<222> LOCATION: (20)..(20)
<223> OTHER INFORMATION: Xaa is Lys conjugated to
      PEG2PEG2-gammaE-C18-OH
<220> FEATURE:
<221> NAME/KEY: MISC_FEATURE
<222> LOCATION: (27)..(27)
<223> OTHER INFORMATION: Xaa is L-methionine sulphone
<220> FEATURE:
<221> NAME/KEY: MISC_FEATURE
<222> LOCATION: (28)..(28)
<223> OTHER INFORMATION: Xaa is  alpha-Methyl-L-Aspartic acid
<220> FEATURE:
<221> NAME/KEY: MISC_FEATURE
<222> LOCATION: (29)..(29)
<223> OTHER INFORMATION: C-terminal amide

<400> SEQUENCE: 79

His Xaa Gln Gly Thr Phe Thr Ser Asp Tyr Ser Lys Leu Leu Asp Ala
1               5                   10                  15

Arg Ala Ala Xaa Asp Phe Val Gln Trp Leu Xaa Xaa Thr Asn His
                20                  25                  30

<210> SEQ ID NO 80
<211> LENGTH: 29
<212> TYPE: PRT
<213> ORGANISM: Artificial sequence
<220> FEATURE:
<223> OTHER INFORMATION: Co-agonist peptide
<220> FEATURE:
<221> NAME/KEY: MISC_FEATURE
<222> LOCATION: (1)..(29)
<223> OTHER INFORMATION: C-terminus of peptide is amidated
<220> FEATURE:
<221> NAME/KEY: MISC_FEATURE
<222> LOCATION: (1)..(29)
<223> OTHER INFORMATION: For each peptide, only one of X20, X21, or X28
      is conjugated to the C16, C17, C18, C19, or C20 fatty diacid
<220> FEATURE:
<221> NAME/KEY: MISC_FEATURE
<222> LOCATION: (1)..(29)
<223> OTHER INFORMATION: For each peptide, only one of X20, X21, ,X24,
      or X28 is conjugated to the C16, C17, C18, C19, or C20 fatty
      diacid
<220> FEATURE:
<221> NAME/KEY: MISC_FEATURE
<222> LOCATION: (2)..(2)
<223> OTHER INFORMATION: Xaa is aminoisobutyric acid (aib) or
      alpha-Methyl-L-Serine (alpha-MS)
<220> FEATURE:
<221> NAME/KEY: MISC_FEATURE
<222> LOCATION: (16)..(16)
<223> OTHER INFORMATION: Xaa is aminoisobutyric acid (aib)
<220> FEATURE:
<221> NAME/KEY: MISC_FEATURE
<222> LOCATION: (20)..(20)
<223> OTHER INFORMATION: Xaa is Gln or Lys conjugated to a C16, C17,
      C18, C19, or C20 fatty diacid
<220> FEATURE:
<221> NAME/KEY: MISC_FEATURE
<222> LOCATION: (21)..(21)
<223> OTHER INFORMATION: Xaa is Asp or Lys conjugated to a C16, C17,
      C18, C19, or C20 fatty diacid or p-aminomethyl-L-phenylalanine
      (pAF) conjugated to a C16, C17, C18, C19, or C20 fatty diacid
<220> FEATURE:
<221> NAME/KEY: MISC_FEATURE
<222> LOCATION: (24)..(24)
<223> OTHER INFORMATION: Xaa is Gln or Lys conjugated to a C16, C17,
      C18, C19, or C20 fatty diacid
<220> FEATURE:
<221> NAME/KEY: MISC_FEATURE
<222> LOCATION: (25)..(25)
<223> OTHER INFORMATION: Xaa is Trp or alpha-Methyl-L-Tryptophan
      (alpha-MW)
<220> FEATURE:
<221> NAME/KEY: MISC_FEATURE
<222> LOCATION: (27)..(27)

```
<223> OTHER INFORMATION: Xaa is L-Met sulphone or Leucine
<220> FEATURE:
<221> NAME/KEY: MISC_FEATURE
<222> LOCATION: (28)..(28)
<223> OTHER INFORMATION: Xaa is Asp or alpha-Methyl-L-Aspartic acid
      (alpha-MD) or p-aminomethyl-L-phenylalanine (pAF) conjugated to a
      C16, C17, C18, C19, or C20 fatty diacid

<400> SEQUENCE: 80

His Xaa Gln Gly Thr Phe Thr Ser Asp Tyr Ser Lys Tyr Leu Asp Xaa
1               5                   10                  15

Arg Ala Ala Xaa Xaa Phe Val Xaa Xaa Leu Xaa Xaa Thr
            20                  25
```

LONG-ACTING CO-AGONISTS OF THE GLUCAGON AND GLP-1 RECEPTORS

CROSS-REFERENCE TO RELATED APPLICATIONS

This application is a U.S. National Phase application under 35 U.S.C. § 371 of PCT Application PCT/US16/58008, filed Oct. 21, 2016, which claims priority from and the benefit of US Provisional Application U.S. Ser. No. 62/246,652; filed Oct. 27, 2015.

REFERENCE TO SEQUENCE LISTING SUBMITTED ELECTRONICALLY

The sequence listing of the present application is submitted electronically via EFS-Web as an ASCII formatted sequence listing with a file name "24198USPCT-SEQLIST-20JUN2018.TXT,"creation date of Sep. 20, 2018, and a size of 71.8 KB. This sequence listing submitted EFS-Web is part of the specification and is herein incorporated by reference in its entirety.

BACKGROUND OF THE INVENTION

(1) Field of the Invention

The present invention is related to long-acting co-agonist peptides of the glucagon and GLP-1 receptors.

(2) Description of Related Art

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1 (7-36) amide or GLP-1 (7-37) acid are biologically potent forms of GLP-1, that demonstrate essentially equivalent activity at the GLP-1 receptor.

During hypoglycemia, when blood glucose levels drop below normal, glucagon signals the liver to break down glycogen and release glucose, causing blood glucose levels to rise toward a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

GLP-1 has different biological activities compared to glucagon. Its actions include stimulation of insulin synthesis and secretion, inhibition of glucagon secretion, and inhibition of food intake. GLP-1 has been shown to reduce hyperglycemia in diabetics. Exendin-4, a peptide from lizard venom that shares about 50% amino acid identity with GLP-1, activates the GLP-1 receptor and likewise has been shown to reduce hyperglycemia in diabetics. There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

Glucagon is a peptide hormone structurally related to GLP-1 that is well recognized for its acute ability to increase blood glucose through stimulation of glycogenolysis and gluconeogenesis (Jiang & Zhang, Am. J. Physio.1 Endocrinol. Metab. 284: E671-E678 (2003)). Of lesser appreciation are the chronic effects of glucagon pharmacology characterized by increases in thermogenesis, satiety, lipolysis, fatty acid oxidation, and ketogenesis (Habegger et al., Nat. Rev. Endocrinol. 6: 689-697 (2010)). Repeated administration of glucagon was first reported decades ago to yield improvements in rodent metabolism, accompanied with lower body weight (Salter, Am. J. Clin. Nutr. 8: 535-539 (1960)). Nonetheless, the inherent risk of hyperglycemia, especially in insulinresistant states such T2DM, has complicated the translation of these observations to human study.

The hormone oxyntomodulin (OXM, glucagon-37) is a posttranslational product of preproglucagon processing in the intestine and central nervous system (CNS) and is secreted from L-cells in the gut in response to food intake. Discovered in 1983, OXM has been implicated in the regulation of food intake and energy expenditure (Jarrouse et al., Endocrinol. 115: 102-105 (1984); Schjoldager et al., Eur. J. Clin. Invest., 18: 499-503 (1988)). Central or peripheral administration of OXM in rats causes a decrease in short term food intake with minimal effects on gastric emptying (Dakin et al. Endocrinology, 142: 4244-4250 (2001), Dakin et al. Endocrinology, 145: 2687-2695 (2004)). Repeated intracerebroventricular administration of OXM in rats results in elevated core temperatures and reduced weight gain compared to pair-fed animals, suggesting effects on both caloric intake and energy expenditure (Dakin et al. Am. J. Physiol. Endocrinol. Metab., 283: E1173-E1177 (2002)).

In related studies, peripheral administration of OXM dose-dependently inhibited both fast-induced and dark phase food intake, but unlike GLP-1, had no effect on gastric emptying. OXM also reduced levels of fasting ghrelin and increased c-fos immunoreactivity, in the arcuate nucleus (ARC). Repeated seven-day IP administration of OXM caused a reduction in the rate of body weight gain and adiposity in rats (See Dakin et al. Endocrinology, 145: 2687-2695 (2004)).

Studies of OXM action in mice have demonstrated that although OXM can activate both the glucagon (GCG) and the GLP-1 receptors, the anorectic actions of OXM require only the GLP-1 receptor, as icy OXM inhibits food intake in glucagon receptor knockout mice. However, the anorectic effects of OXM are completely absent in GLP-1 receptor knockout mice. Furthermore, exendin-4, but not OXM, regulates energy expenditure in mice. Hence, OXM appears to be a weak agonist at the GLP-1 receptor, when used in pharmacological concentrations (See Baggio et al., Gastroenterol. 127: 546-58 (2004)). OXM was also found to ameliorate glucose intolerance in mice fed a high fat diet (Dakin et al., Am. J. Physiol. Endocrinol. Metab. 294: E142-E147 (2008) and increase the intrinsic heart rate in mice independent of the GLP-1 receptor (Sowden et al., Am. J. Physiol. Regul. Integr. Comp. Physiol. 292: R962-R970 (2007). OXM has also been shown to differentially affect GLP-1 receptor beta-arrestin recruitment and signaling through Galpha (Jorgensen et al., J. Pharma. Exp. Therapeut. 322: 148-154 (2007)) and to differentially affect hypothalamic neuronal activation following peripheral injection of OXM (Choudhri et al., Biochem. Biophys. Res. Commun. 350: 298-306 (2006)).

In humans, a single 90 minute intravenous infusion of OXM in normal weight healthy subjects reduced hunger scores and food intake at a buffet meal by about 19%. Cumulative twelve-hour caloric intake was reduced by about 11% with no reports of nausea or changes in food palatability (Cohen et al., J. Clin. Endocrinol. Metab., 88: 4696-4701 (2003); Lykkegaard et al., ADA Scientific Sessions, Abstract #1506-P (2003)). More recently, pre-prandial injections of OXM over a four-week period in obese healthy volunteers (BMI about 33) led to a significant reduction of caloric intake on the first day of treatment (about 25%) that was maintained over the course of the study (35% reduction after four weeks) (Wynne et al., Diabetes 54: 2390-2395 (2005)). Robust weight loss was observed at the end of the study in treated subjects (1.9%, placebo-corrected). Plasma levels of OXM were similar to that observed in the infusion study (peak concentration about 950 pM). The absence of any tachyphylaxis and a low incidence of mild and transient nausea (about 3%) despite the relatively high doses necessitated by the poor in vivo stability of OXM (plasma t1/2<12 minutes) renders this hormone one of the few obesity targets with both human validation and an attractive tolerability profile.

OXM has a very short half-life and is rapidly inactivated by the cell surface dipeptidyl peptidase IV (DPP-IV) (Zhu et al., J. Biol. Chem. 278: 22418-22423 (2002). However, DPP-IV inhibitors are weight-neutral in the clinic, suggesting that supraphysiological levels of OXM (900-1000 pM) may be required to achieve weight loss in humans. OXM peptide analogs for inducing weight loss in humans have been the object of Published International Application Nos. WO03/022304, WO2004/062685, WO2006/134340, and WO2010/096052.

Recently, two independent and simultaneous papers reported the use of relatively balanced GLP-1 receptor/GCG receptor co-agonists as being of enhanced efficacy and safety relative to pure GLP1R agonists in the treatment of rodent obesity, with simultaneous improvement in glycemic control (Day et al., Nat. Chem. Biol. 5: 749-757 (2009); Pocai eta al., Diabetes 58: 2258-2266 (2009)). Of related significance is work with oxyntomodulin (OXM), an endogenous precursor to glucagon, which is secreted postprandially by L-cells of the jejuno-ileum together with GLP-1 (Hoist, Regul. Pept. 93: 45-51 (2000); Drucker, Nat. Clin. Pract. Endocrinol. Metab. 1: 22-31 (2005).

Glucagon peptide analogs and derivatives modified to have various degrees of activity at the GLP-1 receptor and GCG receptor have been disclosed in Published International Application Nos. WO2008/1010017, WO2009/155258, WO2011/075393, WO2012/177444, and WO2012/177443. Some of the disclosed glucagon peptide analogs were reported therein to have activity at both the GLP-1 receptor and GCG receptor; however, there remains a need for co-agonist peptides that have activity or potency at the GLP-1 receptor and GCG receptor.

BRIEF SUMMARY OF THE INVENTION

The present invention provides peptides or co-agonist peptides of the glucagon (GCG) receptor and the glucagon-like protein 1 (GLP-1) receptor that have a long-acting profile comprising a prolonged blood serum half-life. The peptides or co-agonist peptides may have a blood serum half-life of at least one day, two days, three days, four days, five days, six days, or seven days. The co-agonist peptides further comprise modifications that control the relative activity at the GLP-1 receptor verses the glucagon receptor.

Thus, yet another aspect of the invention provides peptides or co-agonist peptides that have higher activity at the glucagon receptor versus the GLP-1 receptor, peptides or co-agonist peptides that have approximately equivalent activity at both receptors, and peptides or co-agonist peptides that have higher activity at the GLP-1 receptor versus the glucagon receptor. The latter category of peptides or co-agonist peptides may be engineered to exhibit little or no activity at the glucagon receptor, and yet retain ability to activate the GLP-1 receptor with the same or better potency than native GLP-1. Any of these analogs may also include modifications that confer enhanced biophysical stability and/or aqueous solubility. The peptides or co-agonist peptides herein are useful for the treatment of metabolic diseases or disorders, such as but not limited to, diabetes (e.g., type 1 diabetes, Type 2 diabetes, or gestational diabetes), non-alcoholic fatty liver disease (NAFLD), non-alcoholic steatohepatitis (NASH), and/or obesity.

Thus, the present invention provides a peptide or co-agonist peptide comprising the formula (SEQ ID NO: 50)
$HX^2QGTFTSX^9X^{10}SX^{12}YX^{14}DX^{16}RAAX^{20}X^{21}X^{22}VX^{24}WLX^{27}X^{28}TX^{30}-NH_2$ Wherein $X^2$ is aminoisobutyric acid (aib) or D-Ser or alpha-Methyl-L-Serine (alpha-MS); $X^9$ is Asp or alpha-Methyl-L-Aspartic acid (alpha-MD); $X^{10}$ is Lys conjugated to a fatty diacid or p-aminomethyl-L-phenylalanine (pAF) conjugated to a fatty diacid or Tyr; $X^{12}$ is Lys conjugated to a fatty diacid, pAF conjugated to a fatty diacid, Lys, or βc; $X^{14}$ is Leu or alpha-L-Leucine (alpha-ML); $X^{16}$ is aib, Ala, or Glu; $X^{20}$ is Lys is conjugated to a fatty diacid, pAF conjugated to a fatty diacid, or Gln; $X^{21}$ is Lys conjugated to a fatty diacid or pAF conjugated to a fatty diacid, Asp, or alpha-MD; $X^{22}$ is Phe or alpha-Methyl-L-phenylalanine (alpha-MF); $X^{24}$ is Gln or βc or Lys conjugated to a fatty diacid or pAF conjugated to a fatty diacid; $X^{27}$ is L-Met sulphone or Leucine; $X^{28}$ is Asp, or alpha-MD, or alpha-Methyl-L-Tryptophan (alpha-MW), Lys, or Ala, or Lys conjugated to a fatty diacid, or pAF conjugated to a fatty diacid; and $X^{30}$ is Lys linked at the C-terminus to gamma-Glu when $X^{27}$ is Leu and $X^{28}$ is Ala;
with the proviso that for each co-agonist peptide, only one of $X^{10}$, $X^{12}$, $X^{20}$, $X^{21}$, $X^{24}$, or $X^{28}$ is conjugated to a fatty diacid.

In particular aspects, the fatty diacid comprises a C14, C15, C16, C17, C18, C19, or C20 fatty diacid. In a further aspect, the fatty diacid comprises a C14 fatty acid.

In particular aspects, the peptide or co-agonist peptide comprises the fatty diacid conjugated to the Lys or pAF via a gamma-Glu, gamma-Glu linker.

In particular aspects, the peptide or co-agonist peptide comprises the fatty diacid conjugated to the Lys or pAF via a $PEG_2PEG_2$-gamma-Glu linker wherein $PEG_2$ is κ-amino-3,6-dioxaoctanoic acid.

In particular aspects, the peptide or co-agonist peptide comprises at $X^{10}$ the pAF conjugated to a fatty diacid or a Lys conjugated to a fatty diacid.

In particular aspects, the peptide or co-agonist peptide comprises at $X^{12}$ the pAF conjugated to a fatty diacid or a Lys conjugated to a fatty diacid.

In particular aspects, the peptide or co-agonist peptide comprises at $X^{20}$ the pAF conjugated to a fatty diacid or a Lys conjugated to a fatty diacid.

In particular aspects, the peptide or co-agonist peptide comprises at $X^{21}$ the pAF conjugated to a fatty diacid or a Lys conjugated to a fatty diacid.

In particular aspects, the peptide or co-agonist peptide comprises at $X^{24}$ the pAF conjugated to a fatty diacid or a Lys conjugated to a fatty diacid.

In a further embodiment, the present invention provides a peptide or co-agonist peptide analog selected from TP340, TP342, TP344, TP369, TP370, TP371, TP372, TP378, TP379, TP380, TP382, TP383, TP384, TP403, TP404, TP406, TP407, TP408, TP409, TP410, TP413, TP416, TP417, TP418, TP419, TP422, TP423, TP424, TP440, TP441, TP442, TP443, TP458, TP461, TP467, TP470, TP472, TP473, TP474, TP475, TP476, TP477, TP491, TP492, TP493, TP494, TP495, TP496, TP560, TP575, TP564, TP598, TP608, TP655, TP654, TP628, TP609, TP597, TP604, TP630, and TP640.

The present invention further provides a composition comprising one or more of any one of the aforementioned peptides or co-agonist peptides and a pharmaceutically acceptable carrier and/or pharmaceutically acceptable salt.

The present invention further provides a method for treating a patient for a metabolic disease or disorder comprising administering the patient an effective amount of any one or more of the aforementioned peptides or co-agonist peptides to treat the metabolic disease or disorder in the patient.

The present invention further provides method for treating a patient for a metabolic disease or disorder comprising administering the patient an effective amount of a composition comprising any one or more of the peptides or co-agonist peptides to treat the metabolic disease or disorder in the patient.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned peptides or co-agonist peptides for manufacture of a medicament for the treatment of a metabolic disease or disorder.

The present invention further provides for the use of any one of the aforementioned peptides or co-agonist peptides or compositions for manufacture of a medicament for the treatment of a metabolic disease or disorder.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the medicament is for treatment of more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

Further provided is method for treating a metabolic disease or disorder in a patient or individual comprising: administering to the patient or individual an effective amount of any one of the aforementioned compositions comprising a peptide or co-agonist peptide agonist and administering to the patient or individual an effective amount of a composition comprising an insulin or insulin analog to treat the metabolic disease or disorder in the patient or individual.

In particular aspects, the composition comprising the peptide or co-agonist peptide is administered at a time prior to the time the composition comprising the insulin or insulin analog is administered. In another aspect, the composition comprising the insulin or insulin analog is administered at a time prior to the time the composition comprising the co-agonist peptide is administered. In a further still aspect, the composition comprising the co-agonist peptide is administered at the same time as the composition comprising the insulin or insulin analog is administered.

In particular aspects, the insulin analog is insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned peptides or co-agonist peptides; an insulin or insulin analog; and, a pharmaceutically acceptable carrier. In particular aspects, the insulin analog is insulin detemir, insulin glargine (U100 or U300), insulin levemir, insulin glulisine, insulin degludec, or insulin lispro.

The present invention further provides for the use of a composition comprising any one of the aforementioned peptides or co-agonist peptides; an insulin or insulin analog; and, a pharmaceutically acceptable carrier for the treatment of a metabolic disease or disorder.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes. The present invention further provides for the use of a composition comprising any one of the aforementioned co-agonist peptides; an insulin or insulin analog; and, a pharmaceutically acceptable carrier for the manufacture of a medicament for the treatment of a metabolic disease or disorder. In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

In particular aspects, the insulin analog is insulin detemir, insulin glargine (U100 or U300), insulin levemir, insulin glulisine, insulin degludec, or insulin lispro.

Definitions

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a peptide or co-agonist peptide herein refers to a nontoxic but sufficient amount of the peptide to provide the desired effect. For example one desired effect would be the prevention or treatment of hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution, or reducing food intake. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route, e.g., subcutaneous, intramuscular, intraspinal, or intravenous.

As used herein, the term "peptide" encompasses a chain of three or more amino acids and typically less than 100 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein. "Non-coded" as used herein refers to an amino acid that is not an L-isomer of any of the following 20 amino acids: Ala, Cys, Asp, Glu, Phe, Gly, His, He, Lys, Leu, Met, Asn, Pro, Gin, Arg, Ser, Thr, Val, Trp, Tyr. "Coded" as used herein refers to an amino acid that is an L-isomer of any of the following 20 amino acids: Ala, Cys, Asp, Glu, Phe, Gly, His, He, Lys, Leu, Met, Asn, Pro, Gin, Arg, Ser, Thr, Val, Trp, Tyr. In some embodiments, the peptides and variant peptides described herein are about the same length as SEQ ID NO: 1 (which is 29 amino acids in length), e.g. 25-35 amino acids in length. Exemplary lengths include 29, 30, 31, 32, 33, 34, 35, 36, 37, 38, 39, 40, 41, 42, 43, 44, 45, 46, 47, 48, 49, or 50 amino acids in length. The term further includes peptides wherein one or more amino acids is conjugated to a second molecule via a linker.

Typically, polypeptides and proteins have a polymer length that is greater than that of "peptides."

Amino acid "modification" refers to an insertion, deletion or substitution of one amino acid with another. In some embodiments, the amino acid substitution or replacement is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues:
Ala, Ser, Thr, Pro, Gly;
II. Polar, negative-charged residues and their amides and esters:
Asp, Asn, Glu, Gin, cysteic acid and homocysteic acid;
III. Polar, positive-charged residues:
His, Arg, Lys; Ornithine (Orn)
IV. Large, aliphatic, nonpolar residues:
Met, Leu, He, Val, Cys, Norleucine (Nle), homocysteine
V. Large, aromatic residues:
Phe, Tyr, Trp, acetyl phenylalanine In some embodiments, the amino acid substitution is not a conservative amino acid substitution, e.g., is a non-conservative amino acid substitution.

As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an EC50 of 1 nM at a first receptor and an $EC_{50}$ of 100 nM at a second receptor has 100-fold selectivity for the first receptor relative to the second receptor.

As used herein, "glucagon potency" or "potency compared to native glucagon" of a molecule refers to the inverse ratio of the $EC_{50}$ of the molecule at the glucagon receptor divided by the $EC_{50}$ of native glucagon at glucagon receptor.

As used herein, "GLP-1 potency" or "potency compared to native GLP-1" of a molecule refers to the inverse ratio of the $EC_{50}$ of the molecule at GLP-1 receptor divided by the $EC_{50}$ of native GLP-1 at GLP-1 receptor.

DETAILED DESCRIPTION OF THE INVENTION

Figure 1A:
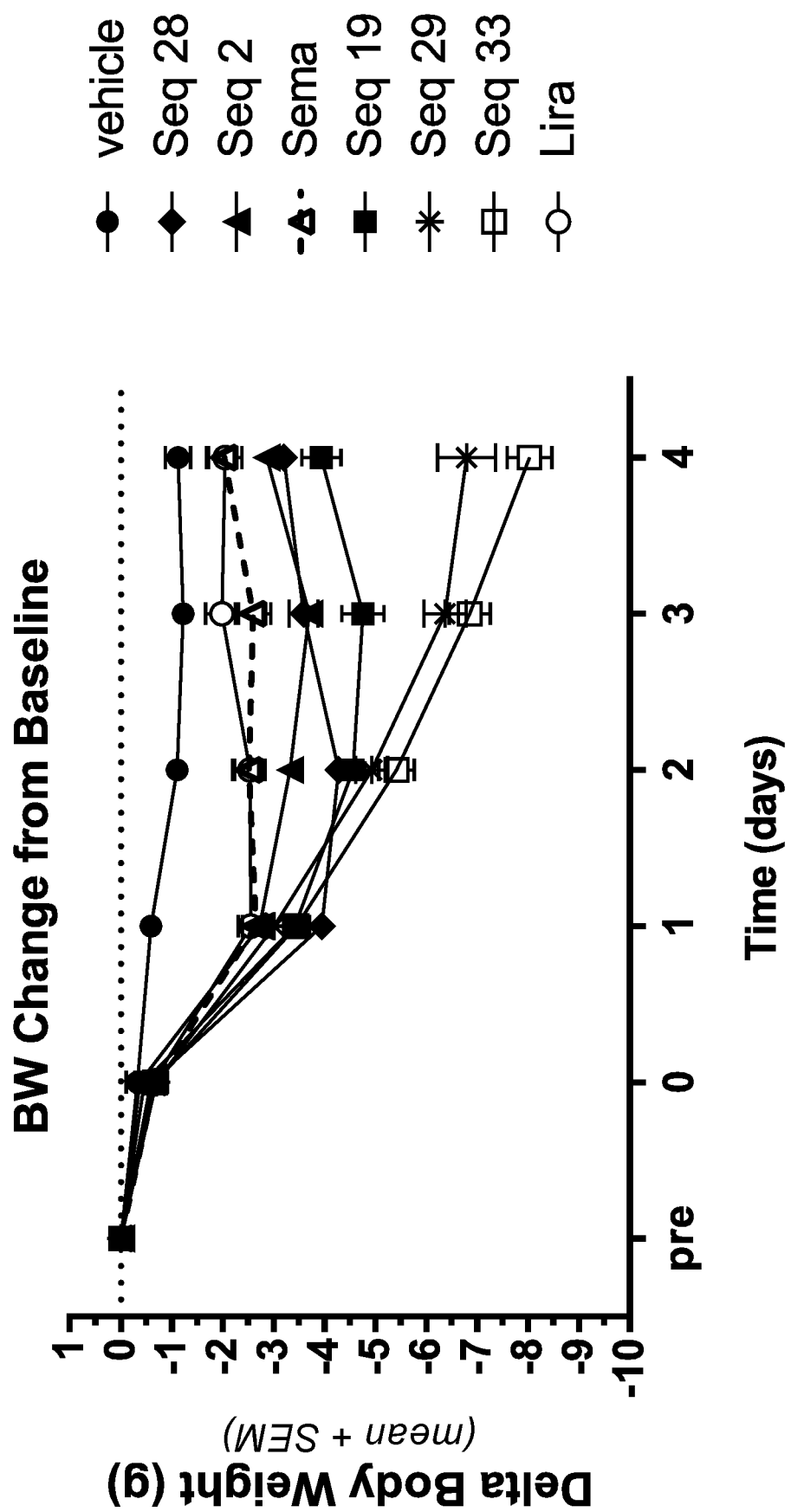
FIG. 1A shows the change in body weight over four days following a single dose of peptide Seq 2, Seq 19, Seq 28, Seq 29, or Seq 33 at day zero compared to liraglutide (lira) and semaglutide (sema). The figure shows that compared to liraglutide and semaglutide, the co-agonist peptides effected a more pronounced and sustained change in body weight over the four day period, in particular the co-agonist peptides Seq 29 and Seq 33.

The present invention provides peptides or peptide co-agonists of the glucagon (GCG) receptor and the glucagon-like protein 1 (GLP-1) receptor that have a long-acting profile comprising a prolonged blood serum half-life. The peptides or co-agonist peptides may have a blood serum half-life of at least one day, two days, three days, four days, five days, six days, or seven days. The peptides or co-agonist peptides further comprise modifications that control the relative activity at the GLP-1 receptor verses the glucagon receptor. Thus, yet another aspect of the invention provides peptides or co-agonist peptides that have higher activity at the glucagon receptor versus the GLP-1 receptor, co-agonist peptides that have approximately equivalent activity at both receptors, and peptides or co-agonist peptides that have higher activity at the GLP-1 receptor versus the glucagon receptor. The latter category of peptides or co-agonist peptides may be engineered to exhibit little or no activity at the glucagon receptor, and yet retain ability to activate the GLP-1 receptor with the same or better potency than native GLP-1. Any of these peptides or co-agonist peptides may also include modifications that confer enhanced biophysical stability and/or aqueous solubility. The peptides or co-agonist peptides herein are useful for the treatment of metabolic disorders, such as but not limited to, diabetes (e.g., type 1 diabetes, Type 2 diabetes, or gestational diabetes), non-alcoholic fatty liver disease (NAFLD), non-alcoholic steatohepatitis (NASH), and/or obesity.

Thus, the present invention provides a peptide or co-agonist peptide comprising of the formula (SEQ ID NO: 50)
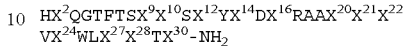

Wherein $X^2$ is aminoisobutyric acid (aib) or D-Ser or alpha-Methyl-L-Serine (alpha-MS); $X^9$ is Asp or alpha-Methyl-L-Aspartic acid (alpha-MD); $X^{10}$ is Lys conjugated to a fatty diacid or p-aminomethyl-L-phenylalanine (pAF) conjugated to a fatty diacid or Tyr; $X^{12}$ is Lys conjugated to a fatty diacid, pAF conjugated to a fatty diacid, Lys, or βc; $X^{14}$ is Leu or alpha-L-Leucine (alpha-ML); $X^{16}$ is aib, Ala, or Glu; $X^{20}$ is Lys conjugated to a fatty diacid, pAF conjugated to a fatty diacid, or Gln; $X^{21}$ is Lys conjugated to a fatty diacid or pAF conjugated to a fatty diacid, Asp, or alpha-MD; $X^{22}$ is Phe or alpha-Methyl-L-phenylalanine (alpha-MF); $X^{24}$ is Gln or βc or Lys conjugated to a fatty diacid or pAF conjugated to a fatty diacid; $X^{27}$ is L-Met sulphone or Leucine; $X^{28}$ is Asp, or alpha-MD, or alpha-Methyl-L-Tryptophan (alpha-MW), Lys, or Ala, or Lys conjugated to a fatty diacid, or pAF conjugated to a fatty diacid; and $X^{30}$ is Lys linked at the C-terminus to gamma-Glu when $X^{27}$ is Leu and $X^{28}$ is Ala;

with the proviso that for each co-agonist peptide, only one of $X^{10}$, $X^{12}$, $X^{20}$, $X^{21}$, $X^{24}$, or $X^{28}$ is conjugated to a fatty diacid.

In particular aspects, the fatty diacid comprises a C14, C15, C16, C17, C18, C19, or C20 fatty diacid. In a further aspect, the fatty diacid comprises a C14 fatty acid.

In particular aspects, the peptide or co-agonist peptide comprises the fatty diacid conjugated to the Lys or pAF via a gamma-Glu, gamma-Glu linker whereas in other aspects, the co-agonist peptide comprises the fatty diacid conjugated to the Lys or pAF via a $PEG_2PEG_2$-gamma-Glu linker wherein $PEG_2$ is 8-amino-3,6-dioxaoctanoic acid.

In particular aspects, the peptide or co-agonist peptide comprises at $X^{10}$ the pAF conjugated to a fatty diacid or a Lys conjugated to a fatty diacid. In particular aspects, the co-agonist peptide comprises at $X^{12}$ the pAF conjugated to a fatty diacid or a Lys conjugated to a fatty diacid. In particular aspects, the co-agonist peptide comprises at $X^{20}$ the pAF conjugated to a fatty diacid or a Lys conjugated to a fatty diacid. In particular aspects, the co-agonist peptide comprises at $X^{21}$ the pAF conjugated to a fatty diacid or a Lys conjugated to a fatty diacid. In particular aspects, the co-agonist peptide comprises at $X^{24}$ the pAF conjugated to a fatty diacid or a Lys conjugated to a fatty diacid.

In a further embodiment, the present invention provides a peptide or co-agonist peptide comprising the formula (SEQ ID NO: 51)
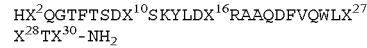

wherein $X^2$ is aminoisobutyric acid (aib) or D-Ser; $X^{10}$ is Lys conjugated to a C16 or C18 or C20 fatty diacid or p-aminomethyl-L-phenylalanine (pAF) conjugated to a C16 or C18 or C20 fatty diacid; $X^{16}$ is aib, Ala, or Glu; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises at $X^{10}$ the pAF conjugated to a C16 or C18 or C20 fatty diacid. In particular aspects, the peptide or co-agonist peptide comprises the fatty diacid conjugated to the Lys or pAF via a gamma-Glu, gamma-Glu linker. In particular aspects, the peptide or co-agonist peptide comprises the fatty diacid conjugated to the Lys or pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula

HX²QGTFTSDYSX¹²YLDX¹⁶RAAQDFVQWLX²⁷DT-NH₂ (SEQ ID NO: 52)

Wherein $X^2$ is aminoisobutyric acid (aib) or D-Ser; $X^{12}$ is Lys conjugated to a C16 or C18 fatty diacid or p-aminomethyl-L-phenylalanine (pAF) conjugated to a C16 or C18 or C20 fatty diacid; $X^{16}$ is aib, Ala, or Glu; and $X^{27}$ is L-Met sulphone or Leucine.

In particular aspects, the peptide or co-agonist peptide comprises at $X^{12}$ the Lys conjugated to a C16 or C18 or C20 fatty diacid. In particular aspects, the peptide or co-agonist peptide comprises at $X^{12}$ the pAF conjugated to a C16 or C18 or C20 fatty diacid. In particular aspects, the peptide or co-agonist peptide comprises the fatty diacid conjugated to the Lys or pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula

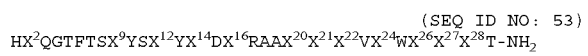
HX²QGTFTSX⁹YSX¹²YX¹⁴DX¹⁶RAAX²⁰X²¹X²²VX²⁴WX²⁶X²⁷X²⁸T-NH₂ (SEQ ID NO: 53)

wherein $X^2$ is aminoisobutyric acid (aib) or D-Ser; $X^9$ is Asp or alpha-MD; $X^{12}$ is Lys or (1S,2S)-Fmoc-2-aminocyclopentane carboxylic acid (βc); $X^{14}$ is Leu or alpha-Methyl-L-Aspartic acid (alpha-MD); $X^{16}$ is aib, Ala, or Glu; $X^{20}$ is Lys conjugated to a C16, C17, C18, C19, or C20 fatty diacid or p-aminomethyl-L-phenylalanine (pAF) conjugated to a C16, C17, C18, C19, or C20 fatty diacid; $X^{21}$ is Asp or alpha-MD; $X^{22}$ is Phe or alpha-Methyl-L-phenylalanine (alpha-MF); $X^{24}$ Gln or βc; $X^{27}$ is L-Met sulphone or Leucine; and $X^{28}$ is Asp, Lys, or alpha-MD.

In particular aspects, the peptide or co-agonist peptide comprises at $X^{20}$ the Lys conjugated to a C16 or C18 or C20 fatty diacid. In particular aspects, the peptide or co-agonist peptide comprises at $X^{20}$ the pAF conjugated to a C16 or C18 or C20 fatty diacid. In particular aspects, the peptide or co-agonist peptide comprises the fatty diacid conjugated to the Lys or pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula

HX²QGTFTSDYSKYLDX¹⁶RAAQX²¹FVQWLX²⁷X²⁸TX³⁰-NH₂ (SEQ ID NO: 54)

wherein $X^2$ is aminoisobutyric acid (aib) or D-Ser; $X^{16}$ is aib, Ala, or Glu; $X^{21}$ is Lys conjugated to a C16, C17, C18, C19, or C20 fatty diacid or p-aminomethyl-L-phenylalanine (pAF) conjugated to a C16, C17, C18, C19, or C20 fatty diacid; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises at $X^{21}$ the Lys conjugated to a C16 or C18 or C20 fatty diacid. In particular aspects, the peptide or co-agonist peptide comprises at $X^{21}$ the pAF conjugated to a C16 or C18 or C20 fatty diacid. In particular aspects, the peptide or co-agonist peptide comprises the fatty diacid conjugated to the Lys or pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula

HX²QGTFTSDYSKYLDX¹⁶RAAQDFVX²⁴WLX²⁷X²⁸TX³⁰-NH₂ (SEQ ID NO: 55)

wherein $X^2$ is aminoisobutyric acid (aib) or D-Ser; $X^{16}$ is aib, Ala, or Glu; $X^{24}$ is Lys or pAF conjugated to a C16, C17, C18, C19, or C20 fatty diacid; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises at $X^{24}$ the pAF or Lys conjugated to a C16 or C18 or C20 fatty diacid. In particular aspects, the peptide or co-agonist peptide comprises the fatty diacid conjugated to the Lys via a $PEG_2PEG_2$-gamma-Glu linker wherein $PEG_2$ is 8-amino-3,6-dioxaoctanoic acid.

The present invention further provides a peptide or co-agonist peptide comprising of the formula

HX²QGTFTSX⁹X¹⁰SX¹²YX¹⁴DX¹⁶RAAX²⁰X²¹X²²VX²⁴WLX²⁷X²⁸TX³⁰-NH₂ (SEQ ID NO: 56)

Wherein $X^2$ is aminoisobutyric acid (aib) or D-Ser; $X^9$ is Asp or alpha-Methyl-L-Aspartic acid (alpha-MD); $X^{10}$ is Lys conjugated to a fatty diacid; $X^{12}$ is Lys conjugated to a fatty diacid, or βc; $X^{14}$ is Leu or alpha-MD; $X^{16}$ is aib, Ala, or Glu; $X^{20}$ is Lys is conjugated to a fatty diacid, Asp, or alpha-MD; $X^{21}$ is Lys conjugated to a fatty diacid, Asp, or alpha-MD; $X^{22}$ is Phe or alpha-Methyl-L-phenylalanine (alpha-MF); $X^{24}$ is Gln or βc or Lys conjugated to a fatty diacid; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala; with the proviso that for each peptide or co-agonist peptide, only one of $X^{10}$, $X^{12}$, $X^{20}$, $X^{21}$, or $X^{24}$ is conjugated to a fatty diacid.

In particular aspects, the fatty diacid comprises a C14, C15, C16, C17, C18, C19, or C20 fatty diacid. In a further aspect, the fatty diacid comprises a C14 fatty acid.

In particular aspects, the peptide or co-agonist peptide comprises the fatty diacid conjugated to the Lys via a gamma-Glu, gamma-Glu linker whereas in other aspects, the peptide or co-agonist peptide comprises the fatty diacid conjugated to the Lys via a $PEG_2PEG_2$-gamma-Glu linker wherein $PEG_2$ is 8-amino-3,6-dioxaoctanoic acid.

In particular aspects, the peptide or co-agonist peptide comprises at $X^{10}$ a Lys conjugated to a fatty diacid. In particular aspects, the peptide or co-agonist peptide comprises at $X^{12}$ a Lys conjugated to a fatty diacid. In particular aspects, the peptide or co-agonist peptide comprises at $X^{20}$ a Lys conjugated to a fatty diacid. In particular aspects, the peptide or co-agonist peptide comprises at $X^{21}$ a Lys conjugated to a fatty diacid. In particular aspects, the peptide or co-agonist peptide comprises at $X^{24}$ a Lys conjugated to a fatty diacid.

In a further embodiment, the present invention provides a peptide or co-agonist peptide comprising the formula

(SEQ ID NO: 57)
HX²QGTFTSDX¹⁰SKYLDX¹⁶RAAQDFVQWLX²⁷X²⁸TX³⁰-NH₂ wherein $X^2$ is aminoisobutyric acid (aib) or D-Ser; $X^{10}$ is Lys conjugated to a C16 or C18 or C20 fatty diacid; $X^{16}$ is aib, Ala, or Glu; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises the fatty diacid conjugated to the Lys via a gamma-Glu, gamma-Glu linker. In particular aspects, the peptide or co-agonist peptide comprises the fatty diacid conjugated to the Lys via a PEG₂PEG₂-gamma-Glu linker wherein PEG₂ is 8-amino-3,6-dioxaoctanoic acid.

In a further embodiment, the present invention provides a peptide or co-agonist peptide comprising the formula

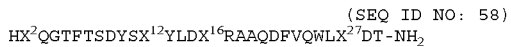
(SEQ ID NO: 58)
HX²QGTFTSDYSX¹²YLDX¹⁶RAAQDFVQWLX²⁷DT-NH₂

Wherein $X^2$ is aminoisobutyric acid (aib) or D-Ser; $X^{12}$ is Lys conjugated to a C16 or C18 or C20 fatty diacid; $X^{16}$ is aib, Ala, or Glu; and $X^{27}$ is L-Met sulphone or Leucine.

In particular aspects, the peptide or co-agonist peptide comprises at $X^{12}$ the Lys conjugated to a C16 or C18 or C20 fatty diacid. In particular aspects, the peptide or co-agonist peptide comprises the fatty diacid conjugated to the Lys via a PEG₂PEG₂-gamma-Glu linker wherein PEG₂ is 8-amino-3,6-dioxaoctanoic acid.

In a further embodiment, the present invention provides a peptide or co-agonist peptide comprising the formula

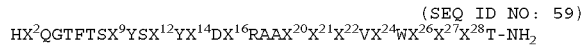
(SEQ ID NO: 59)
HX²QGTFTSX⁹YSX¹²YX¹⁴DX¹⁶RAAX²⁰X²¹X²²VX²⁴WX²⁶X²⁷X²⁸T-NH₂ wherein $X^2$ is aminoisobutyric acid (aib) or D-Ser; $X^9$ is Asp or alpha-MD; $X^{12}$ is Lys or (1S,2S)-Fmoc-2-aminocyclopentane carboxylic acid (βc); $X^{14}$ is Leu or alpha-Methyl-L-Aspartic acid (alpha-MD); $X^{16}$ is aib, Ala, or Glu; $X^{20}$ is Lys conjugated to a C16, C17, C18, C19, or C20 fatty diacid; $X^{21}$ is Asp or alpha-MD; $X^{22}$ is Phe or alpha-Methyl-L-phenylalanine (alpha-MF); $X^{24}$ Gln or βc; $X^{27}$ is L-Met sulphone or Leucine; and $X^{28}$ is Asp, Lys, or alpha-MD.

In particular aspects, the peptide or co-agonist peptide comprises at $X^{20}$ the Lys conjugated to a C16 or C18 or C20 fatty diacid. In particular aspects, the peptide or co-agonist peptide comprises the fatty diacid conjugated to the Lys via a PEG₂PEG₂-gamma-Glu linker wherein PEG₂ is 8-amino-3,6-dioxaoctanoic acid.

In a further embodiment, the present invention provides a peptide or co-agonist peptide comprising the formula

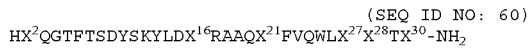
(SEQ ID NO: 60)
HX²QGTFTSDYSKYLDX¹⁶RAAQX²¹FVQWLX²⁷X²⁸TX³⁰-NH₂ wherein $X^2$ is aminoisobutyric acid (aib) or D-Ser; $X^{16}$ is aib, Ala, or Glu; $X^{21}$ is Lys conjugated to a C16, C17, C18, C19, or C20 fatty diacid; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises at $X^{21}$ the Lys conjugated to a C16 or C18 or C20 fatty diacid. In particular aspects, the peptide or co-agonist peptide comprises the fatty diacid conjugated to the Lys via a PEG₂PEG₂-gamma-Glu linker wherein PEG₂ is 8-amino-3,6-dioxaoctanoic acid.

In a further embodiment, the present invention provides a peptide or co-agonist peptide comprising the formula

(SEQ ID NO: 61)
HX²QGTFTSDYSKYLDX¹⁶RAAQDFVX²⁴WLX²⁷X²⁸TX³⁰-NH₂ wherein $X^2$ is aminoisobutyric acid (aib) or D-Ser; $X^{16}$ is aib, Ala, or Glu; $X^{24}$ is Lys conjugated to a C16, C17, C18, C19, or C20 fatty diacid; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises at $X^{24}$ the Lys conjugated to a C16 or C18 or C20 fatty diacid. In particular aspects, the peptide or co-agonist peptide comprises the fatty diacid conjugated to the Lys via a PEG₂PEG₂-gamma-Glu linker wherein PEG₂ is 8-amino-3,6-dioxaoctanoic acid.

The present invention further provides a peptide or co-agonist peptide comprising of the formula

(SEQ ID NO: 62)
HX²QGTFTSX⁹X¹⁰SX¹²YX¹⁴DX¹⁶RAAX²⁰X²¹X²²VX²⁴WLX²⁷X²⁸TX³⁰-NH₂

Wherein $X^2$ is aminoisobutyric acid (aib) or D-Ser; $X^9$ is Asp or alpha-Methyl-L-Aspartic acid (alpha-MD); $X^{10}$ is pAF conjugated to a fatty diacid; $X^{12}$ is pAF conjugated to a fatty diacid, or βc; $X^{14}$ is Leu or alpha-MD; $X^{16}$ is aib, Ala, or Glu; $X^{20}$ is pAF is conjugated to a fatty diacid, Asp, or alpha-MD; $X^{21}$ is pAF conjugated to a fatty diacid, Asp, or alpha-MD; $X^{22}$ is Phe or alpha-Methyl-L-phenylalanine (alpha-MF); $X^{24}$ is Gln or βc or pAF conjugated to a fatty diacid; $X^{27}$ is L-Met sulphone or Leucine; $X^{28}$ is Asp, Lys, or Ala; and $X^{30}$ is pAF conjugated to gamma-Glu when $X^{27}$ is Leu and $X^{28}$ is Ala; with the proviso that for each peptide or co-agonist peptide, only one of $X^{10}$, $X^{12}$, $X^{20}$, $X^{21}$, or $X^{24}$ is conjugated to a fatty diacid.

In particular aspects, the fatty diacid comprises a C14, C15, C16, C17, C18, C19, or C20 fatty diacid. In a further aspect, the fatty diacid comprises a C14 fatty acid.

In particular aspects, the peptide or co-agonist peptide comprises the fatty diacid conjugated to the pAF via a gamma-Glu, gamma-Glu linker whereas in other aspects, the peptide or co-agonist peptide comprises the fatty diacid conjugated to the pAF via a PEG₂PEG₂-gamma-Glu linker wherein PEG₂ is 8-amino-3,6-dioxaoctanoic acid.

In particular aspects, the peptide or co-agonist peptide comprises at $X^{10}$ a pAF conjugated to a fatty diacid. In particular aspects, the peptide or co-agonist peptide comprises at $X^{12}$ a pAF conjugated to a fatty diacid. In particular aspects, the peptide or co-agonist peptide comprises at $X^{20}$ a pAF conjugated to a fatty diacid. In particular aspects, the peptide or co-agonist peptide comprises at $X^{21}$ a pAF conjugated to a fatty diacid. In particular aspects, the peptide or co-agonist peptide comprises at $X^{24}$ a pAF conjugated to a fatty diacid.

In a further embodiment, the present invention provides a peptide or co-agonist peptide comprising the formula

(SEQ ID NO: 63)
HX²QGTFTSDX¹⁰SKYLDX¹⁶RAAQDFVQWLX²⁷X²⁸TX³⁰-NH₂ wherein $X^2$ is aminoisobutyric acid (aib) or D-Ser; $X^{10}$ is pAF conjugated to a C16 or C18 or C20 fatty diacid; $X^{16}$ is aib, Ala, or Glu; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises the fatty diacid conjugated to the pAF via a gamma-Glu, gamma-Glu linker. In particular aspects, the peptide or co-agonist peptide comprises the fatty diacid conjugated to the pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula (SEQ ID NO: 64)
HX²QGTFTSDYSX¹²YLDX¹⁶RAAQDFVQWLX²⁷DT-NH₂

Wherein $X^2$ is aminoisobutyric acid (aib) or D-Ser; $X^{12}$ is pAF conjugated to a C16 or C18 or C20 fatty diacid; $X^{16}$ is aib, Ala, or Glu; and $X^{27}$ is L-Met sulphone or Leucine.

In particular aspects, the peptide or co-agonist peptide comprises at $X^{12}$ the pAF conjugated to a C16 or C18 or C20 fatty diacid. In particular aspects, the peptide or co-agonist peptide comprises the fatty diacid conjugated to the pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula (SEQ ID NO: 65)
HX²QGTFTSX⁹YSX¹²YX¹⁴DX¹⁶RAAX²⁰X²¹X²²VX²⁴WX²⁶X²⁷X²⁸T-NH₂ wherein $X^2$ is aminoisobutyric acid (aib) or D-Ser; $X^9$ is Asp or alpha-MD; $X^{12}$ is Lys or (1S,2S)-Fmoc-2-aminocyclopentane carboxylic acid (βc); $X^{14}$ is Leu or alpha-Methyl-L-Aspartic acid (alpha-MD); $X^{16}$ is aib, Ala, or Glu; $X^{20}$ is pAF conjugated to a C16, C17, C18, C19, or C20 fatty diacid; $X^{21}$ is Asp or alpha-MD; $X^{22}$ is Phe or alpha-Methyl-L-phenylalanine (alpha-MF); $X^{24}$ Gln or βc; $X^{27}$ is L-Met sulphone or Leucine; and $X^{28}$ is Asp, Lys, or alpha-MD.

In particular aspects, the peptide or co-agonist peptide comprises at $X^{20}$ the pAF iconjugated to a C16 or C18 or C20 fatty diacid. In particular aspects, the peptide or co-agonist peptide comprises the fatty diacid conjugated to the pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula (SEQ ID NO: 66)
HX²QGTFTSDYSKYLDX¹⁶RAAQX²¹FVQWLX²⁷X²⁸TX³⁰-NH₂ wherein $X^2$ is aminoisobutyric acid (aib) or D-Ser; $X^{16}$ is aib, Ala, or Glu; $X^{21}$ is pAF conjugated to a C16, C17, C18, C19, or C20 fatty diacid; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises at $X^{21}$ the pAF conjugated to a C16 or C18 or C20 fatty diacid. In particular aspects, the peptide or co-agonist peptide comprises the fatty diacid conjugated to the pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula (SEQ ID NO: 67)
HX²QGTFTSDYSKYLDX¹⁶RAAQDFVX²⁴WLX²⁷X²⁸TX³⁰-NH₂ wherein $X^2$ is aminoisobutyric acid (aib) or D-Ser; $X^{16}$ is aib, Ala, or Glu; $X^{24}$ is pAF conjugated to a C16, C17, C18, C19, or C20 fatty diacid; $X^{27}$ is L-Met sulphone or Leucine; $X^{28}$ is Asp, Lys, or Ala; and $X^{30}$ is Lys conjugated to gamma-Glu when $X^{27}$ is Leu and $X^{28}$ is Ala.

In particular aspects, the peptide or co-agonist peptide comprises at $X^{24}$ the pAF conjugated to a C16 or C18 or C20 fatty diacid. In particular aspects, the peptide or co-agonist peptide comprises the fatty diacid conjugated to the pAF via a $PEG_2PEG_2$-gamma-Glu linker wherein $PEG_2$ is 8-amino-3,6-dioxaoctanoic acid.

In a further embodiment, the present invention provides a peptide or co-agonist peptide comprising the formula (SEQ ID NO: 80)
HX²QGTFTSDYSKYLDX¹⁶RAAX²⁰X²¹FVX²⁴X²⁵LX²⁷X²⁸T-NH₂ wherein $X^2$ is aminoisobutyric acid (aib) or alpha-Methyl-L-Serine (alpha-MS); $X^{16}$ is aib or Ala; $X^{20}$ is Gln or Lys conjugated to a C16, C17, C18, C19, or C20 fatty diacid; $X^{21}$ is Asp or Lys conjugated to a C16, C17, C18, C19, or C20 fatty diacid or p-aminomethyl-L-phenylalanine (pAF) conjugated to a C16, C17, C18, C19, or C20 fatty diacid; $X^{24}$ is Gln or Lys conjugated to a C16, C17, C18, C19, or C20 fatty diacid; $X^{25}$ is Trp or alpha-Methyl-L-Tryptophan (alpha-MW); $X^{27}$ is L-Met sulphone or Leucine; and $X^{28}$ is Asp or alpha-Methyl-L-Aspartic acid (alpha-MD) or p-aminomethyl-L-phenylalanine (pAF) conjugated to a C16, C17, C18, C19, or C20 fatty diacid, with the proviso that one of $X^{20}$, $X^{21}$, or $X^{28}$ is conjugated to the C16, C17, C18, C19, or C20 fatty diacid.

Exemplary peptides or co-agonist peptides of the present invention are shown in Table 1.

TABLE 1

| SEQ ID NO. | Name | Sequence |
|---|---|---|
| 1 | TP340 | HsQGTFTSDYSKYLDXRAAQK(PEG₂PEG₂-γE-C16-OH)FVQWLLATK-γE-NH₂ |
| 2 | TP342 | HsQGTFTSDYSKYLDARAAK(PEG₂PEG₂-γE-C16-OH)DFVQWLLDT-NH₂ |
| 3 | TP344 | HsQGTFTSDYSKYLDARAAQK(PEG₂PEG₂-γE-C16-OH)FVQWLLDT-NH₂ |
| 4 | TP369 | HXQGTF TSDK(PEG₂PEG₂-γE-C18-OH)SKYLDXRAAQDFVQWL2DT-NH₂ |
| 5 | TP370 | HXQGTF TSDYSK(PEG₂PEG₂-γE-C18-OH)YLDXRAAQDFVQWL2DT-NH₂ |
| 6 | TP371 | HsQGTF TSDK(PEG₂PEG₂-γE-C18-OH)SKYLDARAAQDFVQWLLDT-NH₂ |
| 7 | TP372 | HsQGTF TSDYSK(PEG₂PEG₂PEG₂PEG₂-γE-C18-OH)YLDARAAQDFVQWLLDT-NH₂ |
| 8 | TP378 | HXQGTFTSDpAF(PEG₂PEG₂-γE-C16-OH)SKYLDERAAQDFVQWLLKT-NH₂ |
| 9 | TP379 | HsQGTFTSDK(γEγE-C16-OH)SKYLDERAAQDFVQWLLKT-NH₂ |
| 10 | TP380 | HsQGTFTSDpAF(PEG₂PEG₂-γE-C16-OH)SKYLDERAAQDFVQWLLKT-NH₂ |
| 11 | TP382 | HXQGTFTSDpAF(PEG₂PEG₂PEG₂PEG₂-γE-C16-OH)SKYLDXRAAQDFVQWLLATK-γE-NH₂ |

TABLE 1-continued

| SEQ ID NO. | Name | Sequence |
|---|---|---|
| 12 | TP383 | HXQGTFTSDpAF(PEG$_2$PEG$_2$-γE-C16-OH)SKYLDARAAQDFVQWL2DT-NH$_2$ |
| 13 | TP384 | HXQGTFTSDpAF(PEG$_2$PEG$_2$-γE-C16)SKYLDARAAQDFVQWL2DT-NH$_2$ |
| 14 | TP403 | HsQGTFTSDYSKYLDARAAK(PEG$_2$PEG$_2$-γE-C16-OH)DFVQWL2DT-NH$_2$ |
| 15 | TP404 | HsQGTFTSDYSKYLDARAAQK(PEG$_2$PEG$_2$-γE-C16-OH)FVQWL2DT-NH$_2$ |
| 16 | TP406 | HsQGTFTSDYSKYLDERAAQK(PEG$_2$PEG$_2$-γE-C16-OH)FVQWL2DT-NH$_2$ |
| 17 | TP407 | HXQGTFTSDYSKYLDARAAK(PEG$_2$PEG$_2$-γE-C16-OH)DFVQWLLDT-NH$_2$ |
| 18 | TP408 | HXQGTFTSDYSKYLDARAAQK(PEG$_2$PEG$_2$-γE-C16-OH)FVQWLLDT-NH$_2$ |
| 19 | TP409 | HXQGTFTSDYSKYLDARAAQK(PEG$_2$PEG$_2$-γE-C16-OH)DFVQWL2DT-NH$_2$ |
| 20 | TP410 | HXQGTFTSDYSKYLDARAAQK(PEG$_2$PEG$_2$-γE-C16-OH)FVQWL2DT-NH$_2$ |
| 21 | TP413 | HsQGTFTSDYSKYLDARAAQK(PEG$_2$PEG$_2$PEG$_2$PEG$_2$-γE-C18OH)FVQWLLDT-NH$_2$ |
| 22 | TP416 | HsQGTFTSDYSKYLDARAApAF(PEG$_2$PEG$_2$-γE-C16-OH)DFVQWLLDT-NH$_2$ |
| 23 | TP417 | HsQGTFTSDYSKYLDARAAQpAF(PEG$_2$PEG$_2$-γE-C16-OH)FVQWLLDT-NH$_2$ |
| 24 | TP418 | HsQGTFTSDYSpAF(PEG$_2$PEG$_2$-γE-C16-OH)YLDERAAQDFVQWL2DT-NH$_2$ |
| 25 | TP419 | HXQGTFTSDYSpAF(PEG$_2$PEG$_2$-γE-C16-OH)YLDXRAAQDFVQWL2DT-NH$_2$ |
| 26 | TP422 | HXQGTFTSDYSKYLDERAApAF(PEG$_2$PEG$_2$-γE-C16-OH)DFVQWLLKT-NH$_2$ |
| 27 | TP423 | HXQGTFTSDYSKYLDERAAQpAF(PEG$_2$PEG$_2$-γE-C16-OH)FVQWLLKT-NH$_2$ |
| 28 | TP424 | HXQGTFTSDpAF(PEG$_2$PEG$_2$-γE-C18-OH)SKYLDARAAQDFVQWL2DT-NH$_2$ |
| 29 | TP440 | HXQGTFTSDYSKYLDARAAK(PEG$_2$PEG$_2$-γE-C18-OH)DFVQWL2DT-NH$_2$ |
| 30 | TP441 | HXQGTFTSDYSKYLDARAAQK(PEG$_2$PEG$_2$-γE-C18-OH)FVQWL2DT-NH$_2$ |
| 31 | TP442 | HXQGTFTSDYSKYLDARAApAF(PEG$_2$PEG$_2$-γE-C18-OH)DFVQWLLDT-NH$_2$ |
| 32 | TP443 | HXQGTFTSDYSKYLDARAAQpAF(PEG$_2$PEG$_2$-γE-C18-OH)FVQWLLDT-NH$_2$ |
| 33 | TP458 | HXQGTFTSDYSKYLDARAAK(PEG$_2$PEG$_2$-γE-C18-OH)DFVQWL2αMDT-NH$_2$ |
| 34 | TP461 | HXQGTFTSDYSβ$^c$YLDXRAAK(PEG$_2$PEG$_2$-γE-C18-OH)DFVβ$^c$WL2DT-NH$_2$ |
| 35 | TP467 | HXQGTFTSDYSKYLDARAAK(PEG$_2$PEG$_2$PEG$_2$PEG$_2$-γE-C18-OH)αMDFVQWL2DT-NH$_2$ |
| 36 | TP470 | HXQGTFTSDYSβ$^c$YLDXRAAK(PEG$_2$PEG$_2$-γE-C16-OH)DFVβ$^c$WL2DT-NH$_2$ |
| 37 | TP472 | HXQGTFTSαMDYSKYLDARAAK(PEG$_2$PEG$_2$-γE-C16-OH)DFVQWL2DT-NH$_2$ |
| 38 | TP473 | HXQGTFTSDYSKYαMLDARAAK(PEG$_2$PEG$_2$-γE-C16-OH)DFVQWL2DT-NH$_2$ |
| 39 | TP474 | HXQGTFTSDYSKYLDARAAK(PEG$_2$PEG$_2$-γE-C16-OH)DαMFVQWL2DT-NH$_2$ |
| 40 | TP475 | HXQGTFTSDYSKYLDARAAK(PEG$_2$PEG$_2$-γE-C16-OH)DFVQWαML2DT-NH$_2$ |
| 41 | TP476 | HXQGTFTSDYSKYLDARAAK(PEG$_2$PEG$_2$-γE-C16-OH)DFVQWL2αMDT-NH$_2$ |
| 42 | TP477 | HXQGTFTSDYSKYLDARAAK(PEG$_2$PEG$_2$-γE-C16-OH)αMDFVQWL2DT-NH$_2$ |
| 43 | TP491 | HXQGTFTSDYSKYLDARAAK(PEG$_2$PEG$_2$-γE-C20-OH)DFVQWL2DT-NH$_2$ |
| 44 | TP492 | HXQGTFTSDYSKYLDARAAQK( PEG$_2$PEG$_2$-γE-C20-OH)FVQWL2DT-NH$_2$ |
| 45 | TP493 | HXQGTFTSDYSKYLDARAAK(PEG$_2$PEG$_2$-γE-C19-OH)DFVQWL2DT-NH$_2$ |
| 46 | TP494 | HXQGTFTSDYSKYLDARAAQK(PEG$_2$PEG$_2$-γE-C19-OH)FVQWL2DT-NH$_2$ |
| 47 | TP495 | HXQGTFTSDYSKYLDARAAK(PEG$_2$PEG$_2$PEG$_2$PEG$_2$-γE-C17-OH)DFVQWL2DT-NH$_2$ |
| 48 | TP496 | HXQGTFTSDYSKYLDARAAQK(PEG$_2$PEG$_2$-γE-C17-OH)FVQWL2DT-NH$_2$ |
| 49 | TP560 | HXQGTFTSDYSKYLDARAAK(PEG$_2$PEG$_2$-γE-C14-OH)DFVQWL2DT-NH$_2$ |
| 68 | TP575 | HXQGTFTSDYSKYLDXRAAQDFVK(PEG$_2$PEG$_2$-γE-C18-OH)WL2DT-NH$_2$ |
| 69 | TP564 | HXQGTFTSKYDSKYLDXRAAK(PEG$_2$PEG$_2$γE-C20-OH)DFVQWL2DT-NH$_2$ |
| 70 | TP598 | HXQGTFTSDYSKYLDAKAAK(PEG$_2$PEG$_2$--γE-C18-OH)DFVQWL2DT-NH$_2$ |
| 71 | TP608 | HXQGTFTSDYSKYLDARAAQK(PEG$_5$-γE-C18-OH)FVQWL2αMDT-NH$_2$ |
| 72 | TP655 | HαMSQGTFTSDYSKYLDARAAQK(PEG$_2$PEG$_2$-γE-C18-OH)FVQWL2DT-NH$_2$ |
| 73 | TP654 | HαMSQGTFTSDYSKYLDARAAK(PEG$_2$PEG$_2$-γE-C18-OH)DFVQWL2DT-NH$_2$ |
| 74 | TP628 | HXQGTFTSDYSKYLDARAAK(PEG$_2$-γE-C18-OH)DFVOWL2αMDT-NH$_2$ |
| 75 | TP609 | HXQGTFTSDYSKYLDARAAQpAF(PEG$_2$PEG$_2$-γE-C18-OH)FVQWLLαMDT-NH$_2$ |
| 76 | TP597 | HXQGTFTSDYSKLLDARAAK(PEG$_2$PEG$_2$-γE-C18-OH)DFVQWL2DT-NH$_2$ |
| 77 | TP604 | HXQGTFTSDYSKYLDARAAQDFVOWL2pAF(PEG$_2$PEG$_2$-γE-C18-OH)T-NH$_2$ |
| 78 | TP630 | HXQGTFTSDYSKYLDARAAK(PEG$_2$PEG$_2$-γE-C16-OH)DFVQαMWL2DT-NH$_2$ |
| 79 | TP640 | HXQGTFTSDYSKLLDARAAK(PEG$_2$PEG$_2$-γE-C18-OH)DFVQWL2αMDT-NH$_2$ |

Table legend: X = alpha-aminoisobutyric acid; γE = γ-glutamic acid; 2 = L-methionine sulphone; αMD = alpha-Methyl-L-Aspartic acid; αML = alpha-Methyl-L-leucine; αMF = alpha-Methyl-L-phenylalanine; αMS = alpha-Methyl-L-serine s = D-serine; pAF = p-aminomethyl-L-phenylalanine; PEG$_2$ = 8-amino-3,6-dioxaoctanoic acid; C14-OH = —CO—(CH$_2$)$_{12}$—COOH; C16-OH = CO—(CH$_2$)$_{14}$—COOH; C18-OH = —CO—(CH$_2$)$_{16}$—COOH; C17-OH = —CO—(CH$_2$)$_{15}$—COOH; C19-OH = —CO—(CH$_2$)$_{17}$—COOH; C20-OH = —CO—(CH$_2$)$_{18}$—COOH; NH$_2$ = C-terminal amide; and βc = 2-aminocyclopentane carboxylic acid has the structure

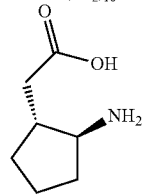

The peptide or co-agonist peptides of the present invention are conjugated to an α,ω-dicarboxylic acid comprising an aliphatic chain of 14 to 20 methylene groups (fatty diacid) wherein one end of the molecule is the proximal end and the other end is the distal end and wherein the proximal end and the distal end both have a carboxyl (COOH) group. The fatty diacid may be represented by the structure HO$_2$C(CH$_2$)$_n$CO$_2$H, wherein n is 11, 13, 14, 15, 16, or 17 to provide fatty diacids Tetradecanedioic acid, Hexadecanedioic acid, Heptadecanedioic acid, Octadecanedioic acid, Nonadecanedioic acid, and Eicosanedioic acid, respectively. The aforementioned fatty diacids have the following structures

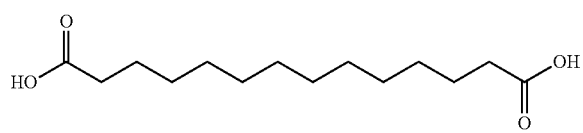

Tetradecanedioic acid

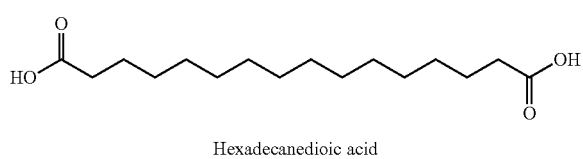

Hexadecanedioic acid

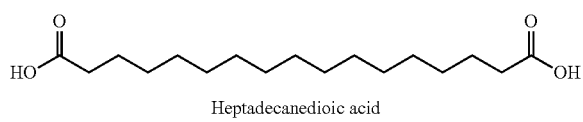

Heptadecanedioic acid

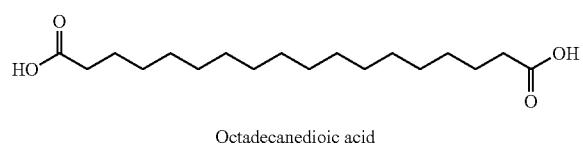

Octadecanedioic acid

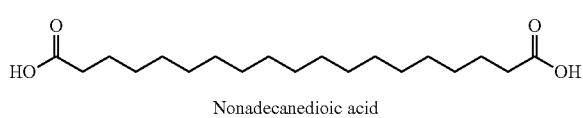

Nonadecanedioic acid

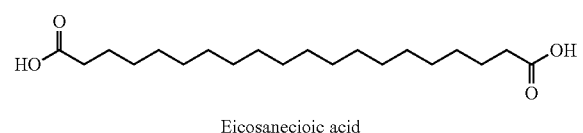

Eicosanecioic acid

As a component of the peptide or co-agonist peptide, the acid functionality at the proximal end of the fatty diacid is conjugated to the amino group of a linker in a C(O)—NH linkage and the acid functionality at the distal end of the fatty diacid is a free carboxyl group (COOH). The COOH group at the distal end helps confer a longer half-life to the peptide or co-agonist peptide by its ability to non-covalently bind to serum albumin, a known carrier for fatty acids in serum. The COOH group enhances duration of action as it provides a better non-covalent interaction with serum albumin than peptides that have been acylated using a fatty acid, which bind serum albumin less efficiently and form a less stable non-covalent interaction with the serum albumin. When the fatty diacid is conjugated to a linking moiety, it is subsequently referred to as a fatty acid component.

The linker may be $PEG_2$ (8-amino-3,6-dioxaoctanoic acid) linked to Gamma-Glutamic acid (gamma-Glu, γGlu, or γE), which has the structure

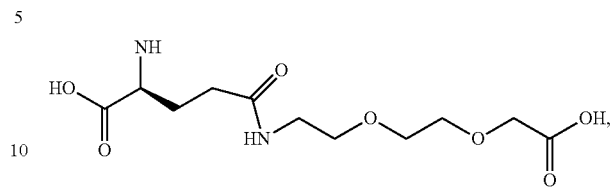

or the linker may be Gamma-Glutamic acid-gamma glutamic acid (gamma-Glu-gamma-Glu, or γGlu-γGlu, or γEγE), which has the structure

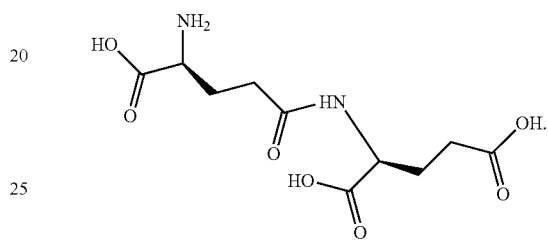

The structure of K($PEG_2PEG_2$γE-fatty acid) wherein the linker is $PEG_2PEG_2$γE and the fatty acid component comprises C14, C16, C17, C18, C19, or C20 is represented by

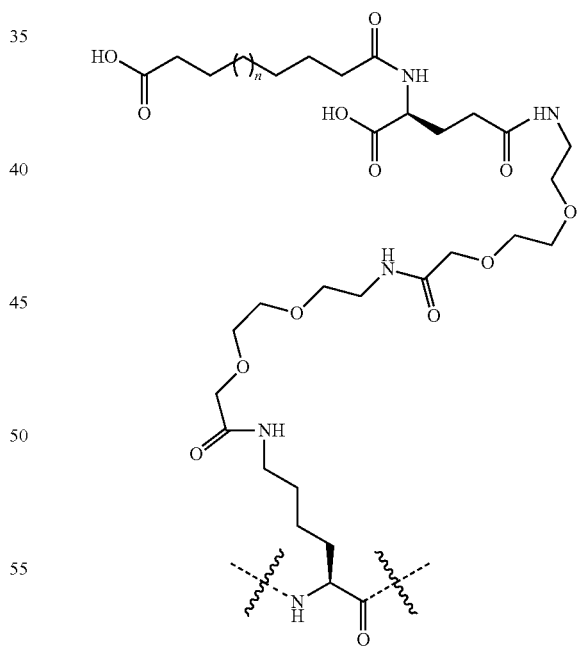

wherein n is 7, 9, 10, 11, 12, 13, or 14 respectively, and the wavy lines represent the bonds between adjacent amino acids in the peptide or co-agonist peptide sequence.

The structure of pAF($PEG_2PEG_2$γE-fatty acid) wherein the linker is $PEG_2PEG_2$γE and the fatty acid component comprises C14, C16, C17, C18, C19, or C20 is represented by

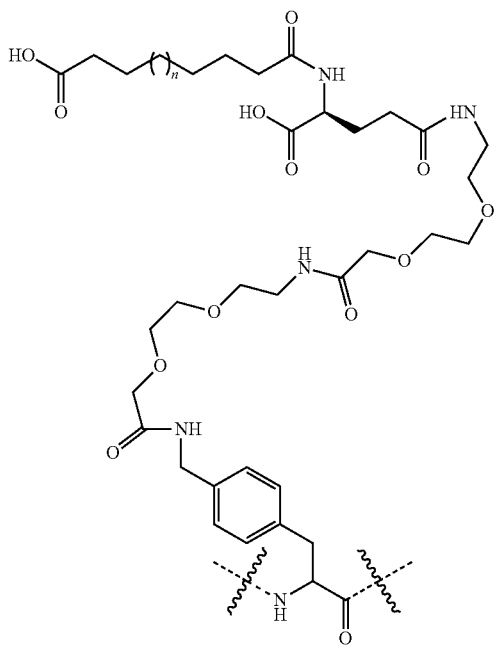

wherein n is 7, 9, 10, 11, 12, 13, or 14, respectively, and the wavy lines represent the bonds between adjacent amino acids in the peptide or co-agonist peptide sequence.

The structure of K(γEγE-fatty acid) wherein the linker is γEγE and the fatty acid component comprises C14, C16, C17, C18, C19, or C20 is represented by wherein n is 7, 9, 10, 11, 12, 13, or 14, respectively, and the wavy lines represent the bonds between adjacent amino acids in the peptide or co-agonist peptide sequence.

The structure of KγE at position 30 in the peptide or co-agonist peptide is represented by wherein the wavy lines represent the bonds between adjacent amino acids in the peptide or co-agonist peptide sequence.

The peptide or co-agonist peptides disclosed herein may have anywhere from at least about 1% (including at least about 1.5%, 2%, 5%, 7%, 10%, 20%, 30%, 40%, 50%, 60%, 75%, 100%, 125%, 150%, 175%) to about 200% or higher activity at the GLP-1 receptor relative to native GLP-1 and anywhere from 5 at least about 1% (including about 1.5%, 2%, 5%, 7%, 10%, 20%, 30%, 40%, 50%, 60%, 75%, 100%, 125%, 150%, 175%, 200%, 250%, 300%, 350%, 400%, 450%) to about 500% or higher activity at the glucagon receptor relative to native glucagon. In some embodiments, the peptide or co-agonist peptides described herein exhibit no more than about 100%, 1000%, 10,000%, 100,000%, or 1,000,000% of the activity of native glucagon at the glucagon receptor. In some embodiments, the peptide or co-agonist peptides described herein exhibit no more than about 100%, 1000%, 10,000%, 100,000%, or 1,000,000% of the activity of native GLP-1 at the GLP-1 receptor. In exemplary embodiments, a peptide or co-agonist peptide may exhibit at least 10% of the activity of native glucagon at the glucagon receptor and at least 50% of the activity of native GLP-1 at the GLP-1 receptor, or at least 40% of the activity of native glucagon at the glucagon receptor and at least 40% of the activity of native GLP-1 at the GLP-1 receptor, or at least 60% of the activity of native glucagon at the glucagon receptor and at least 60% of the activity of native GLP-1 at the GLP-1 receptor.

Selectivity of a glucagon peptide for the glucagon receptor versus the GLP-1 receptor can be described as the relative ratio of glucagon/GLP-1 activity (the peptide analog's activity at the glucagon receptor relative to native glucagon, divided by the peptide's activity at the GLP-1 receptor relative to native GLP-1). For example, a peptide or co-agonist peptide that exhibits 60% of the activity of native glucagon at the glucagon receptor and 60% of the activity of native GLP-1 at the GLP-1 receptor has a 1:1 ratio of glucagon/GLP-1 activity. Exemplary ratios of glucagon/GLP-1 activity include about 1:1, 1.5:1, 2:1, 3:1, 4:1, 5:1, 6:1, 7:1, 8:1, 9:1 or 10:1, or about 1:10, 1:9, 1:8, 1:7, 1:6, 1:5, 1:4, 1:3, 1:2, or 1:1.5. As an example, a glucagon/GLP-1 activity ratio of 10:1 indicates a 10-fold selectivity for the glucagon receptor versus the GLP-1 receptor. Similarly, a GLP-1/glucagon activity ratio of 10:1 indicates a 10-fold selectivity for the GLP-1 receptor versus the glucagon receptor.

Pharmaceutical Compositions

Further provided are pharmaceutical compositions comprising a therapeutically effective amount of one or more of the peptide or co-agonist peptides disclosed herein for the treatment of a metabolic disorder in an individual. Such disorders include, but are not limited to, obesity, metabolic syndrome or syndrome X, type II diabetes, complications of diabetes such as retinopathy, hypertension, dyslipidemias, cardiovascular disease, gallstones, osteoarthritis, and certain forms of cancers. The obesity-related disorders herein are associated with, caused by, or result from obesity.

"Obesity" is a condition in which there is an excess of body fat. The operational definition of obesity is based on the Body Mass Index (BMI), calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk for obesity" is an otherwise healthy subject with a BMI of 25 kg/m2 to less than 30 kg/m2 or a subject with at least one co-morbidity with a BMI of 25 kg/m2 to less than 27 kg/m2.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m2. In Asian countries, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, non-alcoholic fatty liver disease (NAFLD), non-alcoholic steatohepatitis (NASH), fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

U.S. Pat. No. 6,852,690, which is incorporated herein in its entirety, discloses methods for enhancing metabolism of nutrients comprising administering to a non-diabetic patient a formulation comprising a nutritively effective amount of one or more nutrients or any combination thereof and one or more insulinotropic peptides. The peptide or co-agonist peptides disclosed herein are insulinotropic and can be administered to patients with a disturbed glucose metabolism such as insulin resistance but no overt diabetes, as well as patients who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucorticoid excess such as cortisol treatment or Cushings disease, patients with activated counterregulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia. In particular, the administration to such a patient aims to provide a therapy to as rapidly as possible deliver the nutritional and caloric requirements to the patient while maintaining his plasma glucose below the so-called renal threshold of about 160 to 180 milligrams per deciliter of glucose in the blood. Although normal patients not having glucose levels just below the renal threshold can also be treated according to the invention as described above, patients with disturbed glucose metabolism such as hyperglycemic patients whose plasma glucose level is just above the renal threshold also find the therapy suitable for their condition. In particular, such patients who have a degree of hyperglycemia below the renal threshold at intermittent intervals can receive a combination treatment of nutrients plus insulinotropic peptides according to any of the following regimens. Normal patients not suffering from such hyperglycemia can also be treated using the peptide or co-agonist peptides disclosed herein.

The peptide or co-agonist peptides disclosed herein may be used in a pharmaceutical composition when combined with a pharmaceutically acceptable carrier. Such compositions comprise a therapeutically-effective amount of one or more of the peptide or co-agonist peptides disclosed herein and a pharmaceutically acceptable carrier. Such a composition may also be comprised of (in addition to the peptide or co-agonist peptides disclosed herein and a carrier) diluents, fillers, salts, buffers, stabilizers, solubilizers, and other materials well known in the art. Compositions comprising the peptide or co-agonist peptides disclosed herein can be administered, if desired, in the form of salts provided the salts are pharmaceutically acceptable. Salts may be prepared using standard procedures known to those skilled in the art of synthetic organic chemistry.

The term "individual" is meant to include humans and companion or domesticated animals such as dogs, cats, horses, and the like. Therefore, the compositions comprising a compound as disclosed herein are also useful for treating or preventing obesity and obesity-related disorders in cats and dogs. As such, the term "mammal" includes companion animals such as cats and dogs.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to the OXM analogs disclosed herein are meant to also include the pharmaceutically acceptable salts.

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration. The peptide or co-agonist peptides disclosed herein may be in multimers (for example, heterodimers or homodimers) or complexes with itself or other peptides. As a result, pharmaceutical compositions of the invention may comprise one or more peptide or co-agonist peptides disclosed herein in such multimeric or complexed form.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially, or simultaneously.

The pharmacological composition can comprise one or more peptide or co-agonist peptides disclosed herein; one or more peptide or co-agonist peptides disclosed herein and one or more other agents for treating a metabolic disorder; or the pharmacological composition comprising the one or more peptide or co-agonist peptides disclosed herein can be used concurrently with a pharmacological composition comprising an agent for treating a metabolic disorder. Such disorders include, but are not limited to, obesity, metabolic syndrome or syndrome X, type II diabetes, complications of diabetes, hypertension, dyslipidemias, cardiovascular disease, gallstones, osteoarthritis, and certain forms of cancers.

When the pharmacological composition comprises another agent for treating a metabolic disorder or the treatment includes a second pharmacological composition comprising an agent for treating a metabolic disorder, the agent includes, but are not limited to, cannabinoid (CB1) receptor antagonists, glucagon like peptide 1 (GLP-1) receptor agonists, glucagon receptor antagonists, lipase inhibitors, leptin, tetrahydrolipstatin, 2-4-dinitrophenol, acarbose, sibutramine, phentamine, fat absorption blockers, simvastatin, mevastatin, ezetimibe, atorvastatin, sitagliptin, metformin, orlistat, Qnexa, topiramate, naltrexone, bupriopion, hentermine, losartan, losartan with hydrochlorothiazide, and the like.

Examples of other active ingredients that may be administered separately or in the same pharmaceutical composition in combination with a peptide or co-agonist peptide as described herein include, but are not limited to:

(1) other dipeptidyl peptidase-IV (DPP-4) inhibitors (e.g., sitagliptin, alogliptin, linagliptin, vildagliptin, saxagliptin and omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARγ agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); (3) insulin or insulin analogs (e.g., insulin detemir, insulin glulisine, insulin degludec, insulin glargine (U100 or U300), insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., such as those disclosed in WO 98/04528, WO 99/01423, WO 00/39088, and WO 00/69810);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators;
(21) other agonists of the G-protein-coupled receptors: (i) GPR-109, (ii) GPR-119 (e.g., MBX2982 and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl) methoxy)phenyl)iso, 5-(4-((3-(2-methyl-6-(3-hydroxypropoxy)pyridine-3-yl)-2-methylphenyl)methoxy) phenyl)isothiazole-3-ol 1-oxide, and 5-[4-[[3-[4-(3-aminopropoxy)-2,6-dimethylphenyl]phenyl]methoxy] phenyl]isothiazole-3-ol 1-oxide);
(22) SSTR3 antagonists (e.g., such as those disclosed in WO 2009/001836);
(23) neuromedin U receptor agonists (e.g., such as those disclosed in WO 2009/042053, including, but not limited to, neuromedin S (NMS));
(24) SCD inhibitors;
(25) GPR-105 antagonists (e.g., such as those disclosed in WO 2009/000087);
(26) SGLT inhibitors (e.g., ASP1941, SGLT-3, empagliflozin, dapagliflozin, canagliflozin, BI-10773, PF-04971729, remogloflozin, TS-071, tofogliflozin, ipragliflozin, and LX-4211);
(27) inhibitors of acyl coenzyme A:diacylglycerol acyltransferase 1 and 2 (DGAT-1 and DGAT-2); (28) inhibitors of fatty acid synthase;
(29) inhibitors of acyl coenzyme A:monoacylglycerol acyltransferase 1 and 2 (MGAT-1 and MGAT-2);
(30) agonists of the TGR5 receptor (also known as GPBAR1, BG37, GPCR19, GPR131, and M-BAR);
(31) ileal bile acid transporter inhibitors;
(32) PACAP, PACAP mimetics, and PACAP receptor 3 agonists;
(33) PPAR agonists;
(34) protein tyrosine phosphatase-1B (PTP-1B) inhibitors;
(35) IL-1b antibodies, (e.g., XOMA052 and canakinumab);
(36) bromocriptine mesylate and rapid-release formulations thereof;
(37) FGF-21 and analogs and derivatives thereof; and (38) FGF21 mimetics such as agonist antibodies that binds the ß-Klotho and FCFR1c complex.

Of particular interest are metformin hydrochloride, pioglitazone, rosiglitazone, simvastatin, atorvastatin, or a sulfonylurea.

Antiobesity compounds that can be combined with compounds as disclosed herein include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see Chaki et al., "Recent advances in feeding suppressing agents: potential therapeutic strategy for the treatment of obesity," Expert Opin. Ther. Patents, 11: 1677-1692 (2001); Spanswick and Lee, "Emerging antiobesity drugs," Expert Opin. Emerging Drugs, 8: 217-237 (2003); Fernandez-Lopez, et al., "Pharmacological Approaches for the Treatment of Obesity," Drugs, 62: 915-944 (2002); and Gadde, et al., "Combination pharmaceutical therapies for obesity," Exp. Opin. Pharmacother., 10: 921-925 (2009).

In another aspect of the invention, a pharmaceutical composition is disclosed which comprises one or more of the following agents:
(a) a compound as disclosed herein;
(b) one or more compounds selected from the group consisting of:
(1) other dipeptidyl peptidase-IV (DPP-4) inhibitors;
(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARyM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;
(3) sulfonylurea and non-sulfonylurea insulin secretagogues, (e.g., tolbutamide, glyburide, glipizide, glimepiride, mitiglinide, and meglitinides, such as nateglinide and repaglinide);
(4) α-glucosidase inhibitors (e.g., acarbose, voglibose and miglitol);
(5) glucagon receptor antagonists;
(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA: cholesterol acyltransferase inhibitors (e.g., avasimibe);
(7) HDL-raising drugs, such as niacin or a salt thereof and extended-release versions thereof; MK-524A, which is a combination of niacin extended-release and the DP-1 antagonist MK-524; and nicotinic acid receptor agonists;
(8) antiobesity compounds;
(9) agents intended for use in inflammatory conditions, such as aspirin, non-steroidal anti-inflammatory drugs (NSAIDs), glucocorticoids, and selective cyclooxygenase-2 (COX-2) inhibitors;
(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);

(11) glucokinase activators (GKAs) (e.g., AZD6370);
(12) inhibitors of 11β-hydroxysteroid dehydrogenase type 1 (e.g., such as those disclosed in U.S. Pat. No. 6,730,690; WO 03/104207; and WO 04/058741);
(13) inhibitors of cholesteryl ester transfer protein (CETP), (e.g., torcetrapib and MK-0859);
(14) inhibitors of fructose 1,6-bisphosphatase (e.g., such as those disclosed in U.S. Pat. Nos. 6,054,587; 6,110,903; 6,284,748; 6,399,782; and 6,489,476);
(15) inhibitors of acetyl CoA carboxylase-1 or 2 (ACC1 or ACC2);
(16) AMP-activated Protein Kinase (AMPK) activators;
(17) agonists of the G-protein-coupled receptors: (i) GPR-109, (ii) GPR-119 (e.g., MBX2982, and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);
(18) SSTR3 antagonists (e.g., such as those disclosed in WO 2009/011836);
(19) neuromedin U receptor agonists (e.g., such as those disclosed in WO2009/042053, including, but not limited to, neuromedin S (NMS));
(20) inhibitors of stearoyl-coenzyme A delta-9 desaturase (SCD);
(21) GPR-105 antagonists (e.g., such as those disclosed in WO 2009/000087);
(22) inhibitors of glucose uptake, such as sodium-glucose transporter (SGLT) inhibitors and its various isoforms, such as SGLT-1; SGLT-2 (e.g., ASP1941, TS071, BI10773, tofogliflozin, LX4211, canagliflozin, dapagliflozin and remogliflozin; and SGLT-3);
(23) inhibitors of acyl coenzyme A:diacylglycerol acyltransferase 1 and 2 (DGAT-1 and DGAT-2);
(24) inhibitors of fatty acid synthase;
(25) inhibitors of acyl coenzyme A:monoacylglycerol acyltransferase 1 and 2 (MGAT-1 and MGAT-2);
(26) agonists of the TGR5 receptor (also known as GPBAR1, BG37, GPCR19, GPR131, and M-BAR);
(28) bromocriptine mesylate and rapid-release formulations thereof, and
(29) IL-1b antibodies (e.g., XOMA052, and canakinumab);
(30) FGF-21 or analog or derivative;
(31) FGF21 mimetics such as agonist antibodies that binds the ß-Klotho and FCFR1c complex; and
(c) a pharmaceutically acceptable carrier.

When a peptide or co-agonist peptide of the present invention is used contemporaneously with one or more other drugs, peptides, or proteins, a pharmaceutical composition containing such other drugs, peptides, or proteins in addition to the peptide or co-agonist peptide of the present invention may be provided. Accordingly, the pharmaceutical compositions of the present invention include those that also contain one or more other active ingredients, in addition to a co-agonist peptide of the present invention.

Methods of administrating the pharmacological compositions comprising the one or more peptides or co-agonist peptides disclosed herein to an individual include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Intraventricular injection may be facilitated by an intraventricular catheter attached to a reservoir (for example, an Ommaya reservoir). Pulmonary administration may also be employed by use of an inhaler or nebulizer, and formulation with an aerosolizing agent. It may also be desirable to administer the one or more peptides or co-agonist peptides disclosed herein locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the peptides or co-agonist peptides disclosed herein including, but not limited to, encapsulation in liposomes, microparticles, microcapsules; minicells; polymers; capsules; tablets; and the like. In one embodiment, the peptides or co-agonist peptides disclosed herein may be delivered in a vesicle, in particular a liposome. In a liposome, the peptides or co-agonist peptides disclosed herein are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the peptides or co-agonist peptides disclosed herein can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (for example, the brain), thus requiring only a fraction of the systemic dose. See, for example, Goodson, In: *Medical Applications of Controlled Release*, 1984. (CRC Press, Bocca Raton, Fla.).

The amount of the compositions comprising one or more of the peptides or co-agonist peptides disclosed herein which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the composition with which to treat each individual patient. Initially, the attending physician will administer low doses of the composition and observe the patient's response. Larger doses of the composition may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. However, suitable dosage ranges for intravenous administration of the compositions comprising the one or more peptides or co-agonist peptides disclosed herein are generally about 5-500 micrograms (µg) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions comprising the one or more peptides or co-agonist peptides disclosed herein of the present invention. Dosage will also vary according to the age, weight and response of the individual patient.

Further provided is a pharmaceutical pack or kit, comprising one or more containers filled with one or more of the ingredients of the pharmaceutical compositions and peptides or co-agonist peptides disclosed herein. Optionally associated with such container(s) may be a notice in the form prescribed by a governmental agency regulating the manufacture, use or sale of pharmaceuticals or biological products, which notice reflects approval by the agency of manufacture, use or sale for human administration.

The present invention further provides a method for treating a patient for a metabolic disease or disorder comprising administering the patient an effective amount of a composition comprising any one or more of the aforementioned peptides or co-agonist peptides to treat the metabolic disease or disorder in the patient.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides for the use of any one of the aforementioned peptides or co-agonist peptides for manufacture of a medicament for the treatment of a metabolic disease or disorder.

The present invention further provides for the use of any one of the aforementioned peptides or co-agonist peptides for manufacture of a medicament for the treatment of a metabolic disease or disorder.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the medicament is for treatment of more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

Further provided is method for treating a metabolic disease or disorder in a patient or individual comprising: administering to the patient or individual an effective amount of any one of the aforementioned compositions comprising a co-agonist peptide and administering to the patient or individual an effective amount of a composition comprising an insulin or insulin analog to treat the metabolic disease or disorder in the patient or individual.

In particular aspects, the composition comprising the co-agonist peptide is administered at a time prior to the time the composition comprising the insulin or insulin analog is administered. In another aspect, the composition comprising the insulin or insulin analog is administered at a time prior to the time the composition comprising the co-agonist peptide is administered. In a further still aspect, the composition comprising the co-agonist peptide is administered at the same time as the composition comprising the insulin or insulin analog is administered.

In particular aspects, the insulin analog is insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In particular aspects, the diabetes is Type I diabetes, Type II diabetes, or gestational diabetes. In particular aspects, the patient has more than one metabolic disease or disorder, for example, diabetes and NASH, NAFLD, or obesity; obesity and NASH or NAFLD; diabetes, NASH, and obesity; diabetes, NAFLD, and obesity; or diabetes and obesity.

The present invention further provides a composition comprising any one of the aforementioned peptides or co-agonist peptides; an insulin or insulin analog; and, a pharmaceutically acceptable carrier.

The present invention further provides for the use of a composition comprising any one of the aforementioned peptides or co-agonist peptides; an insulin or insulin analog; and, a pharmaceutically acceptable carrier for the treatment of a metabolic disease or disorder.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The present invention further provides for the use of a composition comprising any one of the aforementioned peptides or co-agonist peptides; an insulin or insulin analog; and, a pharmaceutically acceptable carrier for the manufacture of a medicament for the treatment of a metabolic disease or disorder.

In particular aspects, the insulin analog comprises insulin detemir, insulin glargine (U100 or U300), insulin levemir, insulin glulisine, insulin degludec, or insulin lispro.

In particular aspects, the metabolic disease or disorder is diabetes, non-alcoholic fatty liver disease (NAFLD), non-alcoholic steatohepatitis (NASH), or obesity. In further aspects, the diabetes is Type I diabetes, Type II diabetes, or gestational diabetes.

The following examples are intended to promote a further understanding of the present invention.

Example 1

Peptides in Table 1 were synthesized by solid phase synthesis using Fmoc/t-Bu chemistry on a peptide multisynthesizer Symphony (Protein Technologies Inc.) on a 150 µmol scale, using either a Rink-amide PEG-PS resin (Champion, Biosearch Technologies, loading 0.28 mmol/g) or a Rink-amide PS resin (ChemImpex loading 0.47 mmol/g).

All the amino acids were dissolved at a 0.3 M concentration in DMF. The amino acids were activated with equimolar amounts of HATU (O-(7-azabenzotriazol-1-yl)-N,N,N',N'-tetramethyluronium hexafluorophosphate) solution 0.3 M in DMF, and a 2-fold molar excess of DIEA (N,N-diisopropylethylamine), solution 2M in NMP. The acylation reactions were performed in general for 1 hour with a 5-fold excess of activated amino acid over the resin free amino groups with double 45 minutes acylation reactions performed from His' to Thr' and from $F^{22}$ to $V^{23}$.

The side chain protecting groups were: tert-butyl for Glu, Ser, D-Ser, Thr and Tyr; trityl for Asn, Gln and His; tert-butoxy-carbonyl for Lys, Trp; and, 2,2,4,6,7-pentamethyldihydrobenzofuran-5-sulfonyl for Arg; His was introduced as Boc-His(Trt)-OH at the end of the sequence assembly. Amino acid 2 (L-methionine-sulphone) was introduced by acylation of Fmoc-L-methionine-sulphone-COOH. The position used for linker-lipid derivatization, either lysine or pAF (p-aminomethyl-L-phenylalanine) were incorporated with a Dde [1-(4,4-dimethyl-2,6-dioxocyclohex-1-ylidene) ethyl] protecting group on the side chain amino group. The pAF [Fmoc-4-(Dde-aminomethyl)-phenylalanine] amino acid was synthesized as described below. For sequences ID: 33, 34, 35, 37, 38, 39, 40, 41, 42, incorporation of the alpha methyl amino acid and the corresponding following residue were performed by manual coupling with HOAt (Hydroxybenzoazatriazole) and DIC (N,N'-diisopropylcarbodiimide). For sequences ID 34 and 36, the Pc residue [(1S,2S)-Fmoc-2-aminocyclopentane carboxylic acid] was incorporated by manual coupling with HOAt and DIC.

At the end of the assembly, the Dde protecting group of either pAF(Dde) or Lys(Dde) was removed by treatment of 2% hydrazine in DMF. The side chains of Lys or pAF were derivatized with different linkers and fatty diacids by incorporation of Fmoc-Glu-OtBu (γ-glutamic acid), Fmoc-PEG2 [8-(9-Fluorenylmethyloxycarbonyl-amino)-3,6-dioxaoctanoic acid] and the lipid diacids (Tetradecanedioic acid; Hexadecanedioic acid; Eptadecanedioic acid; Octadecanedioic acid; Nonadecanedioic acid; Eicosanedioic acid) using HOAt and DIC as activators.

At the end of the synthesis, the dry peptide-resins were individually treated with 25 mL of the cleavage mixture, 88% TFA, 5% phenol, 2% triisopropylsilane and 5% water for 1.5 hours at room temperature. Each resin was filtered and then added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in H2O, 20% acetonitrile, and lyophilized. The crude peptides (140 mg in 3 ml of DMSO) were purified by reverse-phase HPLC using preparative Waters Deltapak C4 (40×200 mm, 15 μm, 300Å) and using as eluents (A) 0.1% TFA in water and (B) 0.1% TFA in acetonitrile.

Analytical HPLC was performed on a Acquity UPLC Waters Chromatograph with a BEH300 C4 Acquity Waters column 2.1×100 mm, 1.7 μm, at 45° C., using H2O, 0.1% TFA (A) and CH3CN, 0.1% TFA (B) as solvents. The peptides were characterized by electrospray mass spectrometry on an Acquity SQ Detector.

Synthesis of
Fmoc-4-(Dde-aminomethyl)-phenylalanine

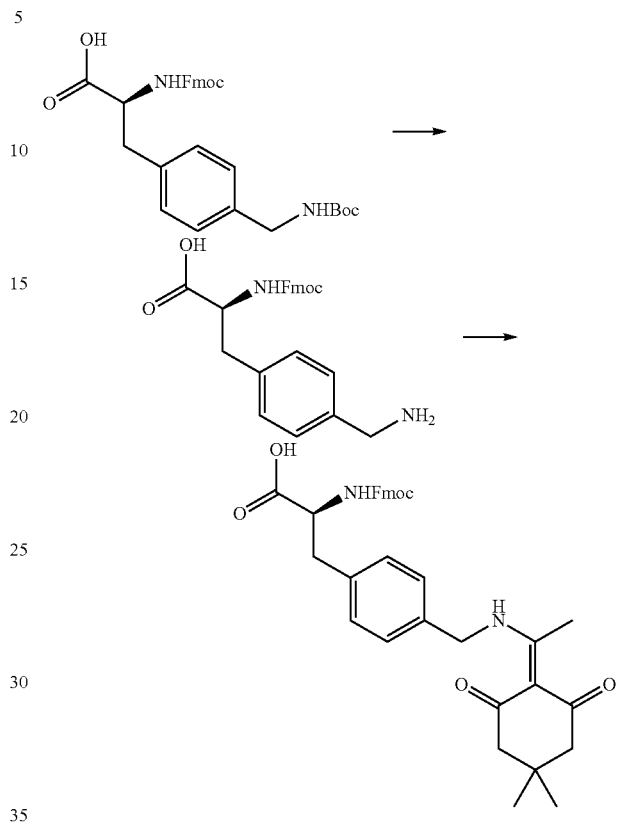

Fmoc-4-(Boc-aminomethyl)-phenylalanine was stirred in DCM/TFA 2/1 for 1 hour. The solvents were removed under reduced pressure and the residue was treated with diethyl ether to obtain a white solid. The crude material obtained was dissolved in EtOH (19 mM), DIPEA (5 eq) and Dimedone (1.1 eq) were added to the reaction mixture. After 3 hours at 60° C. the solution was acidified with TFA to pH 4. The solvents were removed under reduced pressure and the residue was treated with AcOEt and washed with HCl 1N. The organic phase was washed with brine and and dried over Na$_2$SO$_4$. The solvents were removed under reduced pressure and the final product was obtained as yellow oil which was further treated with Et2O to obtain a white solid.

The final compound was characterized on an Acquity UPLC Waters Chromatograph, with BEH300 C18 Acquity Waters 2.1×100 mm, 1.7 μm, at 45° C., using H$_2$O, 0.1% TFA (A) and CH$_3$CN, 0.1% TFA (B) as solvents and the following gradient: 10% to 10% B in 1 min, 10% B over 90% B in 4 min, flow 0.4 mL/min. The protected amino acid was characterized by electrospray mass spectrometry on a Acquity SQ Detector (Mw found: 581.5 Da; Mw expected: 580.67 Da)

Example 2

Activity of the peptides at the Glucagon receptor (GCGR) and GLP-1 receptor (GLP1R) was measured in a cAMP activity assay.

Peptides were dissolved in 100% DMSO and serially diluted to generate 10 point titrations. The peptide solutions were then transferred into 384-well assay plates (150 nL/well). Assay ready frozen cells expressing human GLP1R or human GCGR were suspended in growth media consisting of DMEM medium (GIBCO), 10% FBS (GIBCO), 1×NEAA(GIBCO), 1× P/S (GIBCO), 10 ug/ml Blasticidin (GIBCO) and 200 µg/mL Hygromycin (GIBCO). Cells were then diluted in assay buffer consisting of PBS (GIBCO), 7.5% BSA (Perkin Elmer), 100 µM RO 20-1724 (Sigma), with or without 20% human serum (MP Biomedical). The cell suspensions (15 µL) were then added to the assay plates containing the peptide solutions (30,000 cells/well for human GCGR; 10,000 cells/well for human GLP1R). The cells were incubated for 1 hour at room temperature in the dark. Production of cAMP was determined using HitHunter™ cAMPXS kits (DiscoverX) following manufacturer protocol. The plates were incubated for overnight at room temperature in the dark. Luminescence was measured using an EnVision Multilabel plate reader (Perkin Elmer). Native GLP-1 and Glucagon (Bachem) are used as control peptides. $EC_{50}$ values were calculated using uses a 4 parameter logistic fit based on the Levenberg-Marquardt algorithm. The results are shown in Table 2.

TABLE 2

| SEQ ID NO: | GCGR EC50 human | GLP1R EC50 human | hGCGR/hGLP1R (hTone) |
|---|---|---|---|
| 1 | 0.160 | 1.890 | 0.09 |
| 2 | 0.030 | 0.274 | 0.11 |
| 3 | 0.050 | 0.200 | 0.23 |
| 4 | 1.420 | 0.270 | 5.36 |
| 5 | 0.970 | 0.110 | 8.80 |
| 6 | 1.700 | 1.370 | 1.24 |
| 7 | 0.780 | 0.570 | 1.36 |
| 8 | 0.420 | 0.030 | 15.26 |
| 9 | 1.980 | 0.670 | 3.22 |
| 10 | 0.120 | 0.460 | 0.26 |
| 11 | 1.030 | 0.250 | 4.15 |
| 12 | 0.140 | 0.070 | 1.89 |
| 13 | 0.040 | 0.020 | 2.19 |
| 14 | 0.040 | 1.130 | 0.03 |
| 15 | 0.010 | 0.220 | 0.07 |
| 16 | 0.030 | 0.310 | 0.09 |
| 17 | 0.140 | 0.100 | 1.44 |
| 18 | 0.070 | 0.030 | 2.19 |
| 19 | 0.080 | 0.040 | 2.15 |
| 20 | 0.030 | 0.030 | 0.98 |
| 21 | 0.030 | 0.200 | 0.17 |
| 22 | 0.020 | 0.290 | 0.08 |
| 23 | 0.040 | 0.270 | 0.14 |
| 24 | 0.780 | 0.370 | 4.76 |
| 25 | 0.320 | 0.020 | 14.00 |
| 26 | 0.520 | 0.110 | 4.68 |
| 27 | 0.440 | 0.050 | 9.24 |
| 28 | 0.430 | 0.140 | 3.11 |
| 29 | 0.79 | 0.270 | 2.93 |
| 30 | 0.10 | 0.060 | 1.66 |
| 31 | 0.26 | 0.370 | 0.70 |
| 32 | 0.07 | 0.028 | 2.52 |
| 33 | 0.300 | 0.070 | 4.00 |
| 34 | 0.640 | 1.200 | 0.53 |
| 35 | 0.660 | 0.120 | 5.35 |
| 36 | 0.230 | 0.360 | 0.65 |
| 37 | 0.670 | 0.110 | 6.24 |
| 38 | 0.460 | 0.100 | 4.54 |
| 39 | 0.330 | 0.110 | 2.93 |
| 40 | 0.650 | 0.060 | 10.39 |
| 41 | 0.050 | 0.020 | 3.13 |
| 42 | 0.130 | 0.040 | 3.21 |
| 43 | 0.92 | 0.69 | 1.3 |
| 44 | 0.220 | 0.240 | 0.92 |
| 45 | 0.160 | 0.120 | 1.30 |
| 46 | 0.500 | 0.280 | 1.83 |
| 47 | 0.220 | 0.170 | 1.30 |
| 48 | 0.050 | 0.050 | 1.10 |
| 49 | 0.040 | 0.020 | 1.91 |

TABLE 2-continued

| SEQ ID NO: | GCGR EC50 human | GLP1R EC50 human | hGCGR/hGLP1R (hTone) |
|---|---|---|---|
| 68 | 0.595 | 0.866 | 0.7 |
| 69 | 1.25 | 1.22 | 1 |
| 70 | 1.1 | 0.5 | 2.3 |
| 71 | 0.13 | 0.17 | 1 |
| 72 | 0.25 | 0.31 | 0.8 |
| 73 | 0.91 | 0.44 | 2.1 |
| 74 | 0.86 | 1.39 | 0.6 |
| 75 | 0.36 | 0.42 | 0.9 |
| 76 | 0.74 | 0.61 | 1.2 |
| 77 | 1.09 | 0.47 | 2.3 |
| 78 | 0.89 | 0.29 | 3 |
| 79 | 0.69 | 0.84 | 0.8 |

Example 3

Diet induced obesity (DIO) mice have long been used as surrogates for humans in the study of the efficacy of anti-obesity compounds. The results obtained from such mice in the study of obesity compounds are translatable to humans (See for example, Nilsson et al. Acta Pharmacologia Sinica 33: 173-181 (2012), which is incorporated herein by reference in its entirety). Thus, DIO mice are useful surrogates for humans for the testing the efficacy of compounds intended to treat obesity.

In this example, the duration of action of several of the peptides or co-agonist peptides was evaluated in diet-induced obese (DIO) mice. The duration of action of the peptides were compared to the duration of action of Semaglutide (sema) and Liraglutide (lira). The peptides tested were SEQ ID NOs: 2, 19, 28, 29, and 33 (Seq 2, Seq 19, Seq 28, Seq 29, and Seq 33, respectively).

DIO mice were divided into groups of eight mice per group and the initial average body weight, food intake and basal glucose of each group were matched. Each group of mice was subcutaneously (sc) injected with a single dose of peptide or vehicle control. The administered doses varied between 3 and 300 nmol/kg. Body weight and food intake were measured daily for 4 days after the initial dosing. Blood glucose was measured 5 hours post dose, and then daily for 4 days. A separate set of mice were treated with same dose of each peptide. Serial blood was taken at 5 hours, 24 hours, 48 hours and 72 hours post sc injection to measure drug exposure.

FIG. 1A shows the change in body weight over four days following a single dose of peptide Seq 2, Seq 19, Seq 28, Seq 29, or Seq 33 at day zero compared to liraglutide (lira) and semaglutide (sema). The figure shows that compared to liraglutide and semaglutide, the peptides effected a more pronounced and sustained change in body weight over the four day period. As shown in the figure, the effect was particularly pronounced for peptides Seq 29 or Seq 33.

Figure 1B:
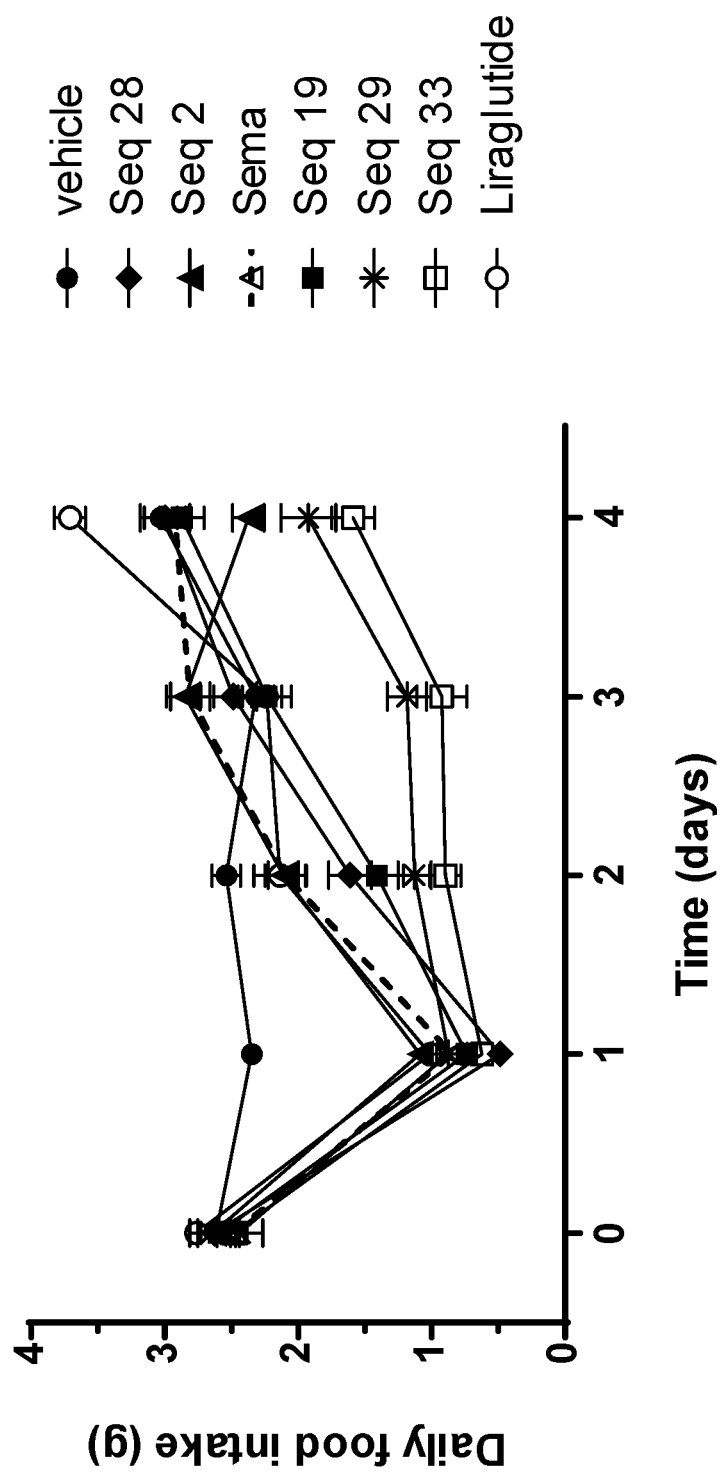
FIG. 1B shows the change in food intake over four days following a single dose of co-agonist peptide Seq 2, Seq 19, Seq 28, Seq 29, or Seq 33 at day zero compared to liraglutide (lira) and semaglutide (sema). The figure shows that the co-agonist peptides have a more sustained reduction in food intake over the four day period that liraglutide or semiglutide, in particular the co-agonist peptides Seq 29 and Seq 33.

FIG. 1B shows the change in food intake over four days following a single dose of peptide Seq 2, Seq 19, Seq 28, Seq 29, or Seq 33 at day zero compared to liraglutide (lira) and semaglutide (sema). The figure shows that the peptides provided a more sustained reduction in food intake over the four day period than liraglutide or semiglutide and the sustained reduction was particularly evident with peptides Seq 29 or Seq 33.

Figure 1C:
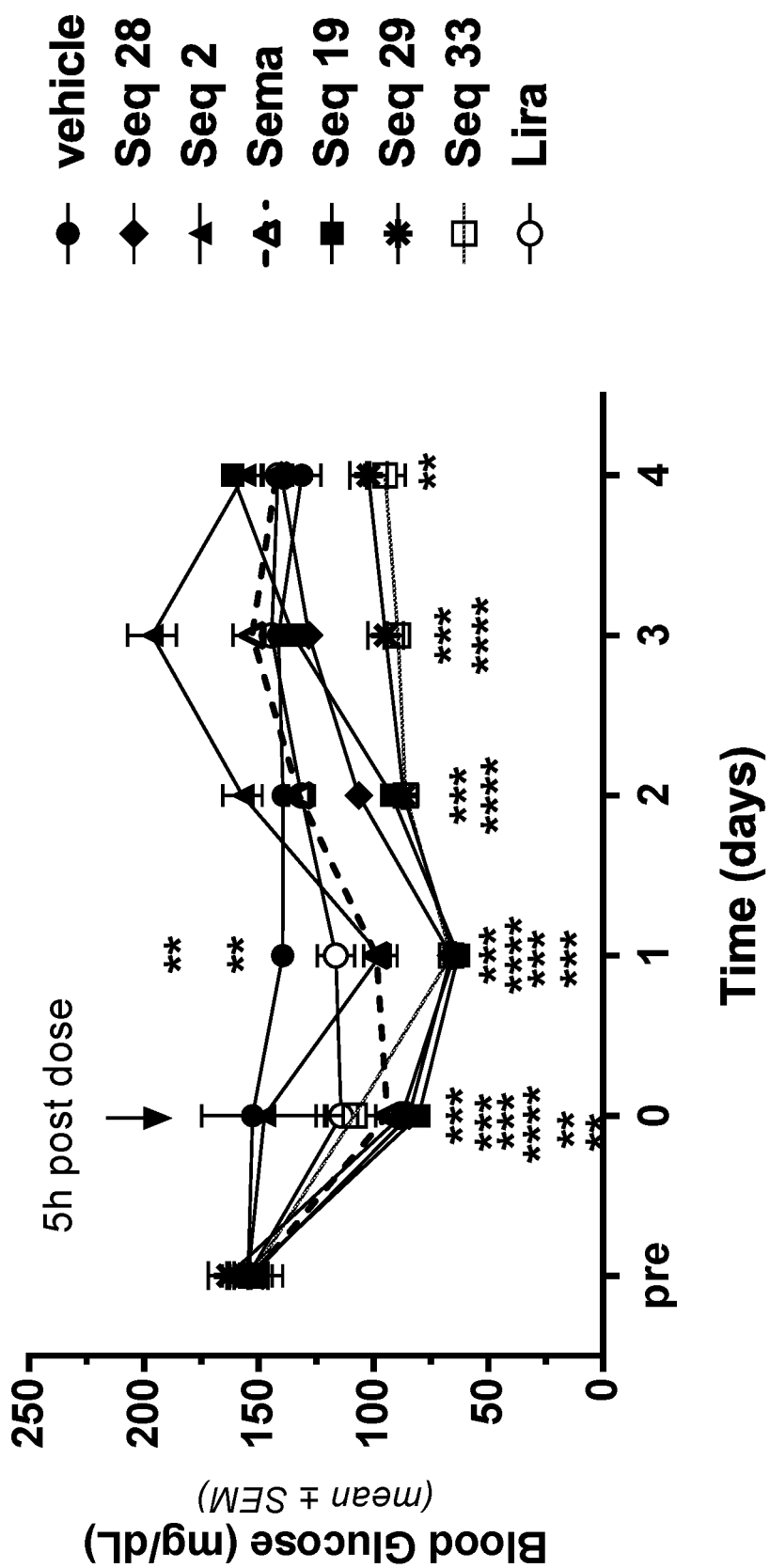
FIG. 1C shows the blood glucose lowering effect over four days following a single dose of co-agonist peptide Seq 2, Seq 19, Seq 28, Seq 29, or Seq 33 at day zero compared to liraglutide (lira) and semaglutide (sema).

FIG. 1C shows the blood glucose lowering effect over four days following a single dose of peptide Seq 2, Seq 19, Seq 28, Seq 29, or Seq 33 at day zero compared to liraglutide (lira) and semaglutide (sema). The figure show that peptides Seq 19, Seq 28, Seq 29, and Seq 33 effected a greater reduction in blood glucose over the four day period that either liraglutide or semiglutide. Peptides Seq29 and Seq 33 were particularly effective at effecting a greater reduction in blood glucose for a sustained period of time.

Figure 2:
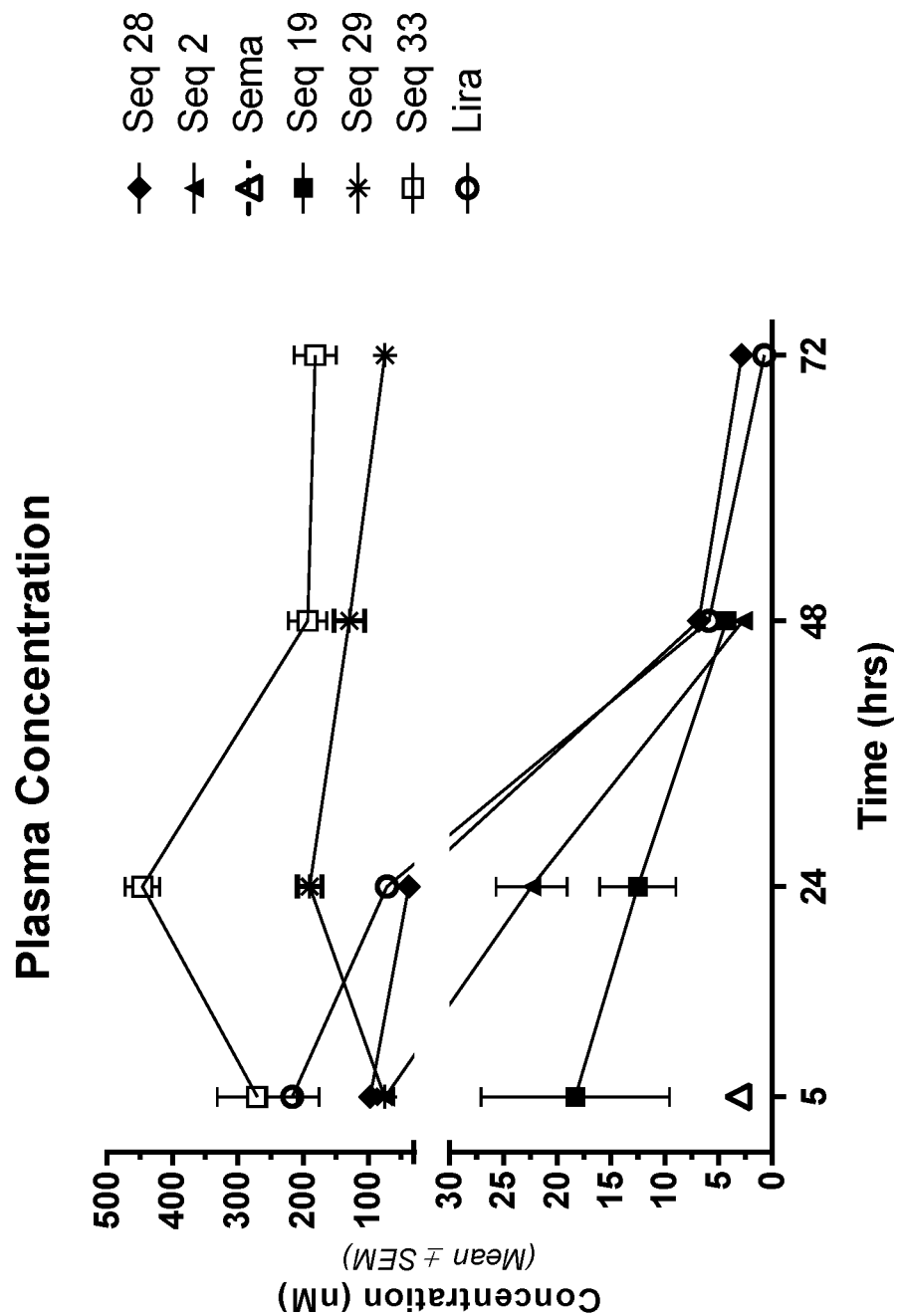
FIG. 2 shows the PK results for co-agonist peptides Seq 2, Seq 19, Seq 28, Seq 29, or Seq 33 at day zero compared to liraglutide (lira) and semaglutide (sema) over three days.

FIG. 2 shows the PK results for peptides Seq 2, Seq 19, Seq 28, Seq 29, or Seq 33 at day zero compared to liraglutide (lira) and semaglutide (sema) over three days. The figure shows that peptides Seq 19 and Seq 33 had a more prolonged PK over the three days compared to semiglutide and liraglutide.

Figure 3A:
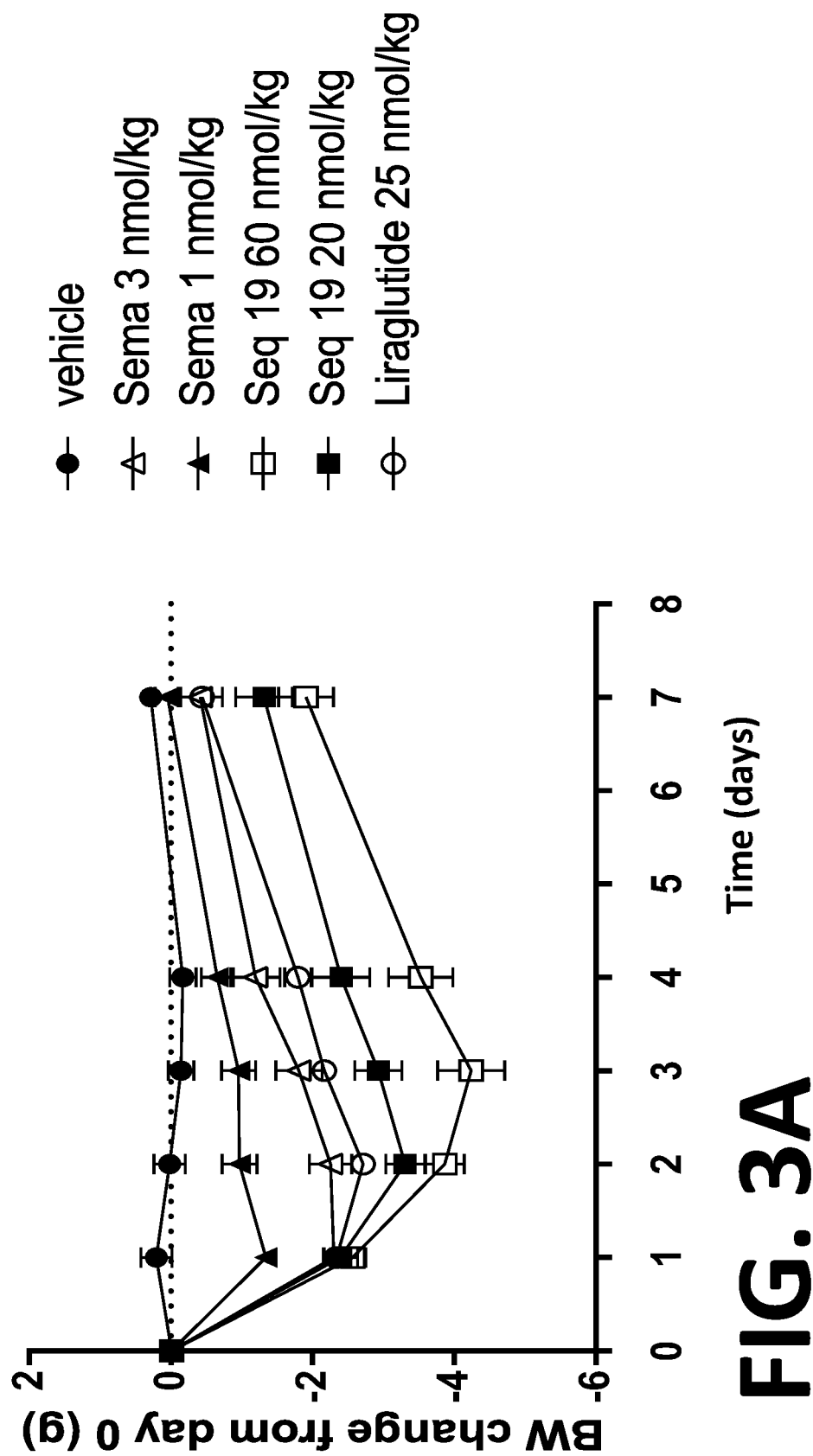
FIG. 3A shows the change in body weight over eight days following a single dose of co-agonist peptide Seq 19 at day zero compared to liraglutide (lira) and semaglutide (sema).

FIG. 3A shows the change in body weight over eight days following a single dose of peptide Seq 19 at 20 nmol/kg or 60 nmol/kg at day zero compared to liraglutide (lira) and semaglutide (sema). The figure shows that compared to liraglutide and semaglutide, peptide Seq 19 effected a more pronounced and sustained change in body weight over the eight day period.

Figure 3B:
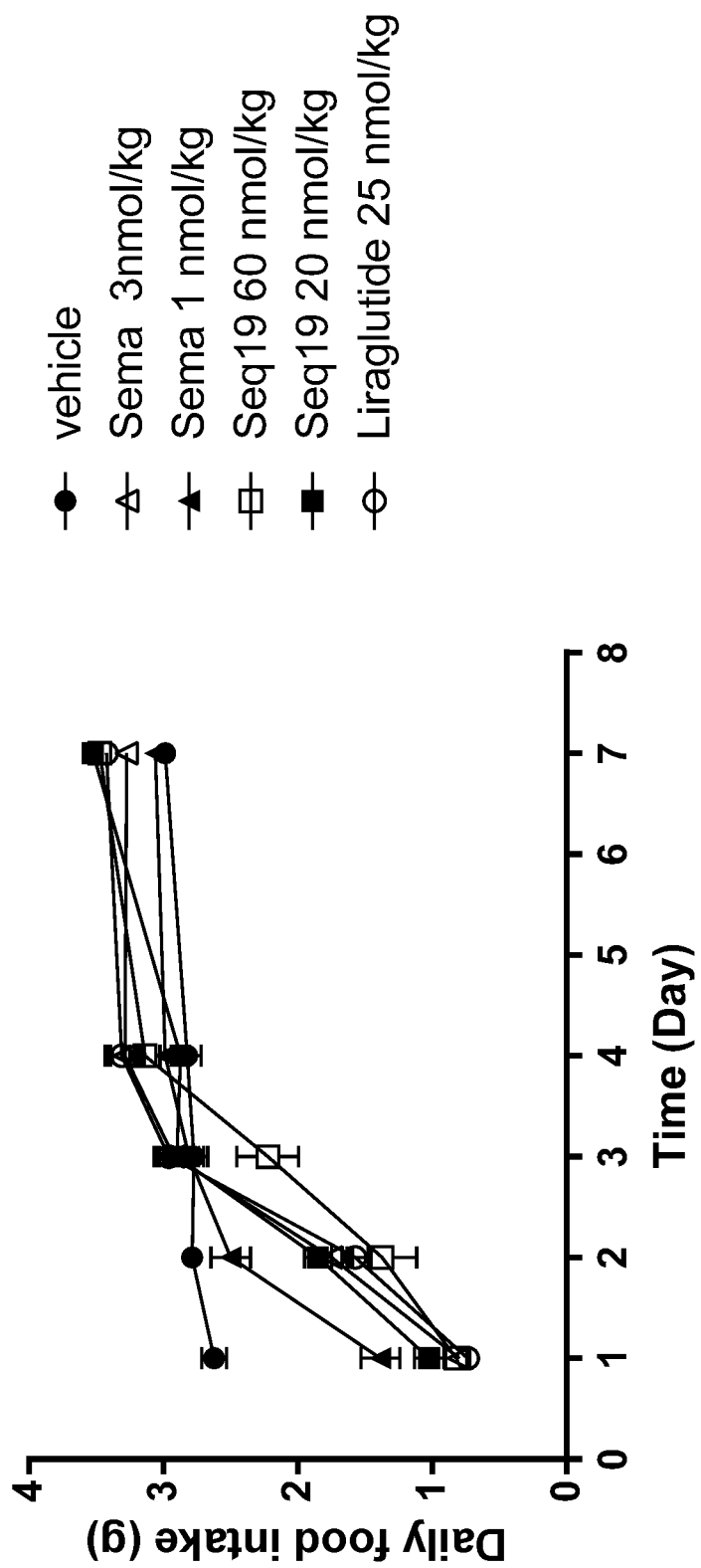
FIG. 3B shows the change in food intake over eight days following a single dose at day zero of co-agonist peptide Seq 19 compared to liraglutide (lira) and semaglutide (sema).

FIG. 3B shows the change in food intake over eight days following a single dose at day zero of peptide Seq 19 at 20 nmol/kg or 60 nmol/kg compared to liraglutide (lira) and semaglutide (sema). The figure shows that peptide Seq19 was comparable to liraglutide or semiglutide in reducing food intake over the eight day period.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A peptide comprising the formula $$HX^2QGTFTSX^9X^{10}SX^{12}YX^{14}DX^{16}RAAX^{20}X^{21}X^{22}VX^{24}WLX^{27}X^{28}TX^{30}-NH_2 \quad (SEQ\ ID\ NO:\ 50)$$

wherein $X^2$ is aminoisobutyric acid (aib), D-Ser or alpha-Methyl-L-Serine (alpha-MS);

$X^9$ is Asp or alpha-Methyl-L-Aspartic acid (alpha-MD);

$X^{10}$ is Lys conjugated to a fatty diacid, p-aminomethyl-L-phenylalanine (pAF) conjugated to a fatty diacid or Tyr-;

$X^{12}$ is Lys conjugated to a fatty diacid, pAF conjugated to a fatty diacid, Lys, or (1S,2S)-Fmoc-2-aminocyclopentane carboxylic acid (βc);

$X^{14}$ is Leu or alpha-L-Leucine (alpha-ML);

$X^{16}$ is aib, Ala, or Glu;

$X^{20}$ is Lys is conjugated to a fatty diacid, pAF conjugated to a fatty diacid or Gln;

$X^{21}$ is Lys conjugated to a fatty diacid, pAF conjugated to a fatty diacid, Asp, or alpha-MD;

$X^{22}$ is Phe or alpha-Methyl-L-phenylalanine (alpha-MF);

$X^{24}$ is Gln (1S,2S)-Fmoc-2-aminocyclopentane carboxylic acid (βc), Lys conjugated to a fatty diacid or pAF conjugated to a fatty diacid;

$X^{27}$ is L-Met sulphone or Leucine;

$X^{28}$ is Asp, alpha-MD, alpha-Methyl-L-Tryptophan (alpha-MW), Lys, Ala, Lys conjugated to a fatty diacid, or pAF conjugated to a fatty diacid; and $X^{30}$ is Lys linked at the C-terminus to gamma-Glu when $X^{27}$ is Leu and $X^{28}$ is Ala, or absent;

with the proviso that for each peptide, only one of $X^{10}$, $x^{12}$, $x^{20}$, $X^{21}$, $X^{24}$, or $X^{28}$ is conjugated to a fatty diacid.

2. The peptide of claim 1, wherein the fatty diacid comprises a C14, C15, C16, C17, C18, C19, or C20 fatty diacid.

3. The peptide of claim 1, wherein the peptide comprises the fatty diacid conjugated to the Lys or pAF via a gamma-Glu, gamma-Glu linker.

4. The peptide of claim 1, wherein the peptide comprises the fatty diacid conjugated to Lys or pAF via a $PEG_2PEG_2$-gamma-Glu linker wherein $PEG_2$ is 8-amino-3,6-dioxaoctanoic acid.

5. The peptide of claim 1, wherein the peptide comprises at $X^{10}$ the pAF conjugated to a fatty diacid or a Lys conjugated to a fatty diacid.

6. The peptide of claim 1, wherein the peptide comprises at $x^{12}$ the pAF conjugated to a fatty diacid or a Lys conjugated to a fatty diacid.

7. The peptide of claim 1, wherein the peptide comprises at $x^{20}$ the pAF conjugated to a fatty diacid or a Lys conjugated to a fatty diacid.

8. The peptide of claim 1, wherein the peptide comprises at $x^{21}$ the pAF conjugated to a fatty diacid or a Lys conjugated to a fatty diacid.

9. The peptide of claim 1, wherein the peptide comprises at $x^{24}$ the pAF conjugated to a fatty diacid or a Lys conjugated to a fatty diacid.

10. A composition comprising one or more peptides of claim 1, or pharmaceutically acceptable salt thereof, and a pharmaceutically acceptable carrier.

11. A composition comprising one or more peptides of claim 1, or pharmaceutically acceptable salt thereof, an insulin or insulin analog, and a pharmaceutically acceptable carrier.

12. The composition of claim 11, wherein the insulin analog comprises insulin detemir, insulin glargine, insulin glulisine, insulin degludec, or insulin lispro.

13. A method for treating a patient for a metabolic disease or disorder comprising administering to a patient in need thereof an effective amount of one or more of the peptides of claim 1 to treat the metabolic disease or disorder in the patient wherein, the metabolic disease or disorder comprises diabetes, nonalcoholic fatty liver disease (NAFLD), non-alcoholic steatohepatitis (NASH), or obesity.

14. The method of claim 13, wherein the diabetes comprises Type I diabetes, Type II diabetes, or gestational diabetes.

15. A method for treating a metabolic disease or disorder in a patient comprising administering to the patient in need thereof an effective amount of one or more of the peptides of claim 1 and administering to the patient in need thereof an effective amount of a composition comprising an insulin or insulin analog to treat the metabolic disease or disorder in the patient, wherein the metabolic disease or disorder comprises diabetes, nonalcoholic fatty liver disease (NAFLD), non-alcoholic steatohepatitis (NASH), or obesity.

16. The method of claim 15, wherein the insulin analog comprises insulin detemir, insulin glargine, insulin levemir, insulin glulisine, insulin degludec, or insulin lispro.

17. The method of claim 15, wherein the diabetes comprises Type I diabetes, Type II diabetes, or gestational diabetes.

* * * * *